US012357394B2

(12) United States Patent
Walen et al.

(10) Patent No.: US 12,357,394 B2
(45) Date of Patent: Jul. 15, 2025

(54) SURGICAL NAVIGATION SYSTEMS AND METHODS

(71) Applicant: Stryker Corporation, Kalamazoo, MI (US)

(72) Inventors: James G. Walen, Portage, MI (US); Zachary Bolthouse, Kalamazoo, MI (US); Zachary Kemp, Naples, FL (US); David Tallon, Shanagarry (IE)

(73) Assignee: Stryker Corporation, Portage, MI (US)

( * ) Notice: Subject to any disclaimer, the term of this patent is extended or adjusted under 35 U.S.C. 154(b) by 417 days.

(21) Appl. No.: 17/764,007

(22) PCT Filed: Sep. 28, 2020

(86) PCT No.: PCT/US2020/053092
§ 371 (c)(1),
(2) Date: Mar. 25, 2022

(87) PCT Pub. No.: WO2021/062373
PCT Pub. Date: Apr. 1, 2021

(65) Prior Publication Data
US 2022/0338938 A1    Oct. 27, 2022

Related U.S. Application Data

(60) Provisional application No. 62/906,413, filed on Sep. 26, 2019.

(51) Int. Cl.
*A61B 17/16*     (2006.01)
*A61B 34/00*     (2016.01)
(Continued)

(52) U.S. Cl.
CPC .......... *A61B 34/20* (2016.02); *A61B 17/1615* (2013.01); *A61B 17/1626* (2013.01);
(Continued)

(58) Field of Classification Search
CPC .. A61B 17/1626; A61B 17/1615; A61B 34/20
See application file for complete search history.

(56) References Cited

U.S. PATENT DOCUMENTS 5,747,953 A    5/1998  Philipp
8,898,043 B2   11/2014 Ashby et al.
(Continued)

FOREIGN PATENT DOCUMENTS

WO    2007002180 A2    1/2007
WO    2009158115 A1   12/2009
(Continued)

OTHER PUBLICATIONS

Partial International Search Report for Application No. PCT/US2020/053092 dated Jan. 13, 2021, 3 pages.
(Continued)

*Primary Examiner* — Olivia C Chang
(74) *Attorney, Agent, or Firm* — Howard & Howard Attorneys PLLC

(57) ABSTRACT

The present disclosure relates generally to a surgical system. The surgical system comprises one or more surgical instrument assemblies and a surgical navigation system. The surgical instrument assemblies comprises a tracking device capable of being tracked by the surgical navigation system. The surgical system is also configured to allow the user to define one or more alert zones relative to anatomical structures of the patient and/or a surgical pathway. The surgical system further comprises an alert device in communication with the surgical navigation system, such that the alert device is configured to provide a user-perceptible alert to the surgeon or medical professional based on the position of the surgical instrument, as determined by the surgical navigation system, relative to the defined alert zones and/or surgical pathway.

19 Claims, 27 Drawing Sheets

(51) Int. Cl.
*A61B 34/10* (2016.01)
*A61B 34/20* (2016.01)
*A61B 17/00* (2006.01)

(52) U.S. Cl.
CPC ...... *A61B 17/1628* (2013.01); *A61B 17/1671* (2013.01); *A61B 34/10* (2016.02); *A61B 34/25* (2016.02); *A61B 34/76* (2016.02); *A61B 2017/00123* (2013.01); *A61B 2017/00128* (2013.01); *A61B 2017/00199* (2013.01); *A61B 2017/00973* (2013.01); *A61B 2034/107* (2016.02); *A61B 2034/254* (2016.02)

(56) References Cited

U.S. PATENT DOCUMENTS

| | | |
|---|---|---|
| 9,295,476 B2 | 3/2016 | Hassler, Jr. |
| 10,016,209 B2 | 7/2018 | Downey et al. |
| 10,235,759 B2 | 3/2019 | Kosmecki et al. |
| 10,517,690 B2 | 12/2019 | Kosmecki et al. |
| 10,555,779 B2 | 2/2020 | Kemp et al. |
| 10,820,912 B2 | 11/2020 | Wildgen et al. |
| 11,432,828 B1 | 9/2022 | Lang |
| 2004/0034283 A1 | 2/2004 | Quaid |
| 2013/0060278 A1* | 3/2013 | Bozung .............. A61B 34/70 606/205 |
| 2014/0039517 A1 | 2/2014 | Bowling et al. |
| 2014/0232316 A1 | 8/2014 | Philipp |
| 2015/0366624 A1 | 12/2015 | Kostrzewski et al. |
| 2016/0074123 A1 | 3/2016 | Bly et al. |
| 2016/0242858 A1 | 8/2016 | Moctezuma de la Barrera et al. |
| 2016/0354162 A1 | 12/2016 | Yen et al. |
| 2017/0061242 A1 | 3/2017 | Vincent et al. |
| 2017/0333137 A1 | 11/2017 | Roessler |
| 2018/0014891 A1 | 1/2018 | Krebs et al. |
| 2018/0199999 A1 | 7/2018 | Syverson et al. |
| 2018/0333207 A1 | 11/2018 | Moctezuma De la Barrera |
| 2019/0105072 A1 | 4/2019 | Govari et al. |
| 2019/0117322 A1 | 4/2019 | Laubenthal et al. |
| 2019/0201023 A1 | 7/2019 | Shelton, IV et al. |
| 2019/0365477 A1 | 12/2019 | Reddy et al. |
| 2019/0388157 A1 | 12/2019 | Shameli et al. |

FOREIGN PATENT DOCUMENTS

| | | |
|---|---|---|
| WO | 2018203304 A1 | 11/2018 |
| WO | 2019215056 A1 | 11/2019 |

OTHER PUBLICATIONS

International Search Report for Application No. PCT/US2020/053092 dated May 19, 2021, 4 pages.

* cited by examiner

SURGICAL NAVIGATION SYSTEMS AND METHODS

CROSS-REFERENCE TO RELATED APPLICATIONS

This application is a National Stage of International Application No. PCT/US2020/053092, filed Sep. 28, 2020, which claims the benefit of U.S. Provisional Application No. 62/906,413, filed Sep. 26, 2019. The entire contents of these applications are hereby incorporated herein by reference in their entirety.

BACKGROUND

In modern surgery, one of the most important instruments available to medical personnel are powered surgical instruments, such as cordless drills, saws, wire drivers, high speed drills, ultrasonic handpieces, or the like. Often these surgical instruments comprise a motor and/or processor within a handpiece or housing. The surgical instrument may comprise an attachment feature configured to receive a cutting attachment designed for application to a surgical site to perform a specific medical procedure. For example, a surgical drill may utilize a cutting attachment such as a drill bit, bur, or reamer for cutting bores into tissue or for selectively removing tissue such as bone. The ability to use powered surgical instruments on a patient lessens the physical strain of surgeons when performing medical procedures on a patient. Moreover, most surgical procedures can be performed more quickly and more accurately with powered surgical instruments than with the manual equivalents that preceded them.

Surgical navigation systems may assist surgeons in navigation of surgical instruments during surgical procedures, such as sinus, spinal, or cranial surgeries. Such surgical procedures may involve inserting a surgical instrument into a surgical site, traversing a surgical pathway from the surgical site to a surgical target region, and manipulating the surgical target region. Some surgical navigation systems include a display on which the location of the surgical instruments is overlaid onto one or more 2-D representations of the patient (e.g., CT or MRI images). Using this system, the surgeon can identify the location of the surgical instrument, but not whether the surgical instrument is correctly proceeding along the surgical pathway, or whether the surgical instrument is correctly manipulating the surgical target region. As a result, in some instances, a surgical instrument can deviate from the surgical pathway or the surgical target region. At the same time, precise navigation of the surgical instrument is important, as vital anatomical features may be in close proximity to the surgical pathway or the surgical target region. It is important to be aware when the surgical instrument has veered off course and/or may be approaching a vital anatomical region. Therefore, there is a need in the art for identifying when the surgical instrument has veered off course and/or may be approaching a vital anatomical region and notifying the medical professional.

SUMMARY

The present disclosure relates generally to a surgical system. The surgical system may generally comprise one or more surgical instrument assemblies and/or a surgical navigation system. The surgical instrument assemblies may comprise a tracking device capable of being tracked by the surgical navigation system. The surgical system may also be configured to allow the user to define one or more alert zones relative to the anatomical structures of the patient and/or the surgical pathway. The surgical system may further comprise an alert device in communication with the surgical navigation system, such that the alert device may be configured to provide a user perceptible alert to the surgeon or medical professional based on the position of the surgical instrument, as determined by the surgical navigation system, relative to the defined alert zones and/or surgical pathway.

An exemplary configuration provides a surgical system configured to allow a medical professional to define an alert zone relative to a critical structure on a patient in a known coordinate system to assist the medical professional in performing surgery on a patient. The surgical system also includes a navigation system. The system also includes a control console may include a control processor in communication with the navigation system. The system also includes a high-speed surgical instrument including a bur, said high-speed surgical instrument may include a variable speed motor in communication with said control processor, said variable speed motor configured to rotate said bur at a first cutting speed of greater than 70,000 rotations per minute and a second cutting speed of below 70,000 rotations per minute and above 60,000 rotations per minute. The system also includes a footswitch for controlling operation of said variable speed motor of said high-speed surgical instrument in communication with said control processor. The system also includes where the navigation system is configured to actively determine a position of said bur relative to the alert zone in the known coordinate system. The system also includes where the navigation system is configured to send a signal to said control processor to manipulate said variable speed motor of said high-speed surgical instrument to transition the rotation of said bur from said first cutting speed to said second cutting speed when the navigation system determines said bur enters the alert zone; and where the transition of said bur from said first cutting speed to said second cutting speed creates a perceptible change as the bur transitions from said first cutting speed to said second cutting speed to notify the medical professional that said bur has entered said alert zone.

In another exemplary configuration, a surgical system capable of defining an alert zone relative to a critical structure in a known coordinate system to assist a medical professional in performing surgery on a patient. The surgical system also includes a navigation system. The system also includes a high-speed surgical instrument may include a bur and may include a variable speed motor configured to rotate a bur. The system also includes a control console may include a control processor, said control processor in communication with said variable speed motor of said high-speed surgical instrument and configured to receive data from the navigation system. The system also includes a footswitch in communication with said control processor for controlling operation of said variable speed motor of said high-speed surgical bur, said footswitch may include a tactile alert device. The system also includes where the navigation system is configured to determine a position of said bur relative to the alert zone and to send data to said control processor indicating the position of said bur relative to the alert zone and said control processor is configured to manipulate said tactile alert device of said footswitch based on said position of said bur relative to said alert zone in the known coordinate system to provide a notification to the medical professional.

In yet another exemplary configuration, a surgical system for use by a medical professional in surgery on a patient. The surgical system also includes a surgical instrument assembly may include: a control console including a processor; a handpiece in communication with said processor of said control console, said handpiece for coupling to an end-effector and a variable speed motor for driving the end-effector; a switch manipulatable by the medical professional between a first position and a second position for controlling the energization of said variable speed motor; a switch sensor configured to detect the position of said switch and communicate a first signal to said processor indicative of said position of said switch The system also includes a navigation system in communication with said processor, said navigation system configured to actively determine a position of said end-effector relative to a first boundary defined in a known coordinate system. The system also includes where said navigation system is configured to communicate a second signal to said processor to deenergize said variable speed motor based upon said position of said end-effector relative to said first boundary in the known coordinate system. The system also includes where upon de-energization of said handpiece said processor is configured to prevent reenergization of said variable speed motor until a subsequent said first signal is received from said switch sensor indicating the medical professional has manipulated said position of said switch while said end-effector remains in the first position.

In yet another exemplary configuration, a surgical system capable of defining an alert zone in a known coordinate system to assist a medical professional in performing surgery on a patient. The surgical system also includes a navigation system. The system also includes a hand-held surgical instrument for coupling to an end-effector, said hand-held surgical instrument may include a motor configured to rotate said end-effector. The system also includes a control processor disposed in said hand-held surgical instrument said control processor in communication with said motor and configured to receive data from said navigation system. The system also includes a trigger disposed on said hand-held surgical instrument, said trigger in communication with said control processor for controlling operation of said motor of said surgical instrument. The system also includes where said trigger may include a tactile alert device. The system also includes where said navigation system is configured to send data to said control processor that said end-effector has entered the alert zone and said control processor is configured to manipulate said tactile alert device of said trigger to notify the medical professional when said end-effector enters said alert zone.

In yet another exemplary configuration, a surgical system for use by a medical professional in surgery on a patient. The surgical system also includes a hand-held surgical instrument configured to drive an end-effector may include: a variable speed motor for rotating said end-effector, a trigger manipulatable by the medical professional between a first position and a second position, a trigger sensor configured to detect said position of said trigger and output a first signal indicative of said position of said trigger. The system also includes a rechargeable battery module removably coupled to said hand-held surgical instrument, said battery module may include: a transceiver configured to send and receive a signal; a battery processor in communication with said transceiver and in communication with said trigger sensor, said battery processor configured to selectively provide power to said variable speed motor of said hand-held surgical instrument based, at least in part, on said first signal indicative of said position of said trigger. The system also includes a navigation system in communication with said battery processor via said transceiver, said navigation system configured to actively determine a position of said end-effector relative to a first boundary defined relative to a known coordinate system. The system also includes where said navigation system is configured to communicate a second signal to said battery processor to limit power to said hand-held surgical instrument based on said position of said end-effector and said first boundary in the known coordinate system. The system also includes where upon said battery processor limiting power to said hand-held surgical instrument, said battery processor is configured to prevent energization of said variable speed motor until a subsequent said first signal is received from said trigger sensor indicating the medical professional has manipulated said position of said trigger.

In yet another exemplary configuration, a surgical system for use by a medical professional in surgery on a patient. The surgical system also includes a hand-held surgical instrument configured to drive an end-effector may include: a variable speed motor; a trigger manipulatable by the medical professional between a first position and a second position; and a handpiece processor configured to control energization of said variable speed motor based, at least in part, on said position of said trigger. The system also includes a rechargeable battery module removably coupled to said hand-held surgical instrument, said battery module may include: a transceiver configured to send and receive a signal; a battery processor in communication with said transceiver, said processor being configured to energize and deenergize said hand-held surgical instrument. The system also includes a navigation system in communication with said battery processor via said transceiver, said navigation system configured to actively determine a position of said hand-held surgical instrument relative to a boundary in a known coordinate system. The system also includes where said navigation system is configured to communicate a first signal to said battery processor to temporarily de-energize said hand-held surgical instrument based on said position of said end-effector relative to said boundary in said known coordinate system. The system also includes while said hand-held surgical instrument remains at or adjacent said boundary and after said battery processor de-energizes said handheld surgical instrument, said navigation system is configured to determine a direction of motion of said end-effector being in a proximal or distal direction relative to the boundary and to communicate a second signal to said battery processor. The system also includes where said battery processor is configured to re-energize said hand-held surgical instrument based on the motion of said hand-held surgical instrument being in a proximal direction relative to said boundary.

In yet another exemplary configuration, a surgical system for use by a medical professional to perform surgical procedure on a patient. The surgical system also includes a hand-held surgical instrument configured to accept an end-effector, said hand-held surgical instrument may include: a variable speed motor configured to rotate said end-effector; a trigger manipulatable by the medical professional between a first position and a second position; a trigger sensor configured to detect said position of said trigger and output a first signal indicative of said position of said trigger; and a handpiece processor configured to control energization of said variable speed motor based, at least in part, upon said first signal from said trigger sensor indicating said position of said trigger. The system also includes a navigation system in communication with said processor, said navigation system configured to define a first boundary and to actively determine a position of said surgical instrument relative to said first boundary and communicate a second signal to said handpiece processor to deactivate said variable speed motor when said trigger sensor indicates said trigger is in said second position and said navigation system determines said hand-held surgical instrument is adjacent and/or distal to said first boundary. The system also includes while said hand-held surgical instrument remains adjacent and/or distal to said first boundary, said handpiece processor is configured to reactivate said variable speed motor upon receiving a subsequent said first signal from said trigger sensor indicating the medical professional has manipulated said trigger to move said trigger from said second position to said first position and back to said second position.

In yet another exemplary configuration, a surgical system for use by a medical professional in spinal or cranial surgery on a patient. The surgical system also includes a hand-held surgical instrument configured to accept an end-effector, said hand-held surgical instrument may include: a handpiece, a variable speed motor disposed within said handpiece, a trigger manipulatable by the medical professional to activate and deactivate said variable speed motor, a switch manipulatable by the medical professional between a first position and a second position for controlling a speed of said variable speed motor, a processor configured to control energization of said variable speed motor. The system also includes a navigation system in communication with said processor, said navigation system configured to determine whether said switch is in said first position or said second position. The system also includes where said navigation system is configured to communicate a signal to said processor to control energization of said variable speed motor based on said switch being in appropriate said position and based on a type of said end-effector coupled to said hand-held surgical instrument.

In yet another exemplary configuration, a surgical system for use by a medical professional in performing a surgical procedure on a patient. The surgical system also includes a hand-held surgical instrument assembly may include: a handpiece; one of a first end-effector or a second end-effector, each of said first end-effector and said second end-effector removably couplable to said handpiece; a variable speed motor disposed within said handpiece; and a processor configured to control energization of said variable speed motor. The system also includes a navigation system in communication with said processor, said navigation system determines an identity of said first end-effector and said second end-effector. The system also includes where said navigation system configured to define a first boundary in a known coordinate system based, at least in part, on identification of said first end-effector and to define a second boundary in the known coordinate system different from said first boundary, said second boundary based, at least in part, on identification said second end-effector. The system also includes when said first end-effector is identified, said navigation system is configured to communicate a first signal to said processor to control energization of said variable speed motor based on position of said first end-effector relative to said first boundary. The system also includes when said second end-effector is identified, said navigation system is configured to communicate a signal to said processor to control energization of said variable speed motor based on position of said second end-effector relative to said second boundary.

In yet another exemplary configuration, a method of navigating a surgical instrument using a navigation system during a medical procedure on a patient. The method also includes determining a planned pose of a selected implant in a known coordinate system; creating a plurality of boundaries within the known coordinate system based on the pose of the selected implant, the plurality of boundaries including a drill-specific boundary and a driver-specific boundary. The method also includes tracking the position of the surgical instrument using the navigation system; activating the drill-specific boundary based on an identification of the end-effector as a drill-instrument, activating the driver-specific boundary based on identification of the end-effector as a driver-instrument. The method also includes controlling the energization of the motor of the handpiece when the drill-instrument has been identified based on the drill-specific boundary and a position of the handpiece. The method also includes controlling energization of the motor of the handpiece when the driver-instrument has been identified based on the driver-specific boundary and a position of the handpiece.

In yet another exemplary configuration, a surgical system for use by a medical professional in surgery on a patient. The surgical system also includes a high-speed surgical instrument assembly may include: a control console including a processor; a handpiece in communication with said processor of said control console, said handpiece may include an end-effector and a variable speed motor for driving said end-effector; a switch manipulatable by the medical professional between a first position and a second position for controlling the energization of said variable speed motor. The system also includes a navigation system in communication with said processor, said navigation system configured to actively determine a position of said handpiece relative a boundary in a known coordinate system. The system also includes where said navigation system is configured to communicate a first signal to said processor to temporarily deenergize said handpiece upon said navigation system determining said position of said handpiece is at or adjacent to the boundary. The system also includes where upon reenergizing said variable speed motor, said navigation system is configured to communicate a second signal to said processor to cause said processor to energize or deenergize said handpiece based on the motion of said handpiece being distal relative to the boundary.

In yet another exemplary configuration, a surgical system for use by a medical professional in surgery on a patient. The surgical system also includes a high-speed surgical instrument assembly may include: a control console including a processor; a handpiece in communication with said processor of said control console, said handpiece may include an end-effector and a variable speed motor for driving said end-effector; a first switch manipulatable by the medical professional between a first position and a second position for controlling the energization of said variable speed motor in a forward direction; and a second switch manipulatable by the medical professional between a first position and a second position for controlling the energization of said variable speed motor in a reverse direction. The system also includes a navigation system in communication with said processor, said navigation system configured to actively determine a position of said handpiece relative to an alert zone defined about a critical structure on the patient. The system also includes where said navigation system is configured to communicate a first signal to said processor to deenergize said handpiece upon said navigation system determining said position of said handpiece has entered said alert zone and said variable speed motor is in said forward direction. The system also includes where upon said processor deenergizing said handpiece and while said handpiece remains in said alert zone, said navigation system is configured to communicate a second signal to said processor to cause said processor to prevent reenergization of said variable speed motor in said forward direction and allow reenergization of said variable speed motor in said reverse direction.

In yet another exemplary configuration, a surgical instrument assembly for use with a navigation system configured to allow a medical professional to define an alert zone on the patient to assist the medical professional in performing surgery on a patient. The surgical instrument assembly also includes a control console may include a control processor in communication with the navigation system. The assembly also includes a high-speed surgical bur assembly may include a variable speed motor in communication with said control processor, said variable speed motor configured to rotate a bur. The assembly also includes a footswitch moveable between a first position and a second position for energizing said variable speed motor of said high-speed surgical bur assembly. The assembly also includes a footswitch sensor in communication with said control processor, said footswitch configured to detect said position of said footswitch and communicate a first signal to said control processor indicative of said position of said footswitch. The assembly also includes a tactile alert device coupled to said footswitch and in communication with said control processor, said tactile alert device position on said footswitch so that said tactile alert device is in contact with the foot of the medical professional when the medical professional compresses said footswitch to operate said high-speed surgical bur assembly. The assembly also includes where the navigation system is configured to actively determine a position of said bur relative to the alert zone in a known coordinate system. The assembly also includes where the navigation system is configured to send a second signal to said control processor to activate said tactile alert device to emit a tactile alert that is capable of being perceived by the medical professional when said bur enters the alert zone; and where, while said bur is still within the alert zone, said processor is configured deactivate said tactile alert device upon receiving a subsequent said first signal from said footswitch sensor indicating the medical professional moved said footswitch.

In yet another exemplary configuration, a surgical system for use by a medical professional in surgery on a patient. The surgical system also includes a drill assembly may include: a control console including a processor; a handpiece in communication with said processor of said control console, said handpiece may include an end-effector and a variable speed motor for driving said end-effector; a switch manipulatable by the medical professional between a first position and a second position for controlling the energization of said variable speed motor. The system also includes a navigation system in communication with said processor, said navigation system configured to actively determine a position of said handpiece relative to a boundary defined relative to a critical structure on the patient. The system also includes where said navigation system is configured to communicate a first signal to said processor to cause said processor to adjust a torque map by which said variable speed motor of said handpiece is powered in response to the end-effector being adjacent or distal to said boundary.

In yet another exemplary configuration, a surgical system configured to allow a medical professional to define an alert zone relative to a critical structure on a patient to assist the medical professional in performing surgery on a patient. The surgical system also includes a navigation system. The system also includes a control console may include a control processor in communication with the navigation system. The system also includes a high-speed surgical instrument including a bur. The system also includes a footswitch for controlling operation of said variable speed motor of said high-speed surgical instrument in communication with said control processor. The system also includes where the navigation system is configured to: actively determine a position of said bur relative to the alert zone, trigger an alert response when the navigation system determines that said bur enters the alert zone, deactivate the alert response based on a user input signal, re-trigger the alert response based on the bur being outside the alert zone for a predetermined time and subsequently re-entering the alert zone.

These and other configurations, features, and advantages of the present disclosure will be apparent to those skilled in the art. The present disclosure is not intended to be limited to or by these configurations, embodiments, features, and/or advantages.

BRIEF DESCRIPTION OF THE DRAWINGS

Advantages of the present invention will be readily appreciated as the same becomes better understood by reference to the following detailed description when considered in connection with the accompanying drawings, wherein.

DETAILED DESCRIPTION

Reliable tracking of surgical instruments during the execution of surgical procedures to follow the planned surgical pathway and/or to avoid critical anatomical structures is of the utmost importance. Furthermore, providing feedback and/or notifying the medical professional executing the procedure when the surgical instrument becomes misaligned with the surgical pathway and/or is at risk of impinging on a critical anatomical structure is of similar importance.

Figure 1A:
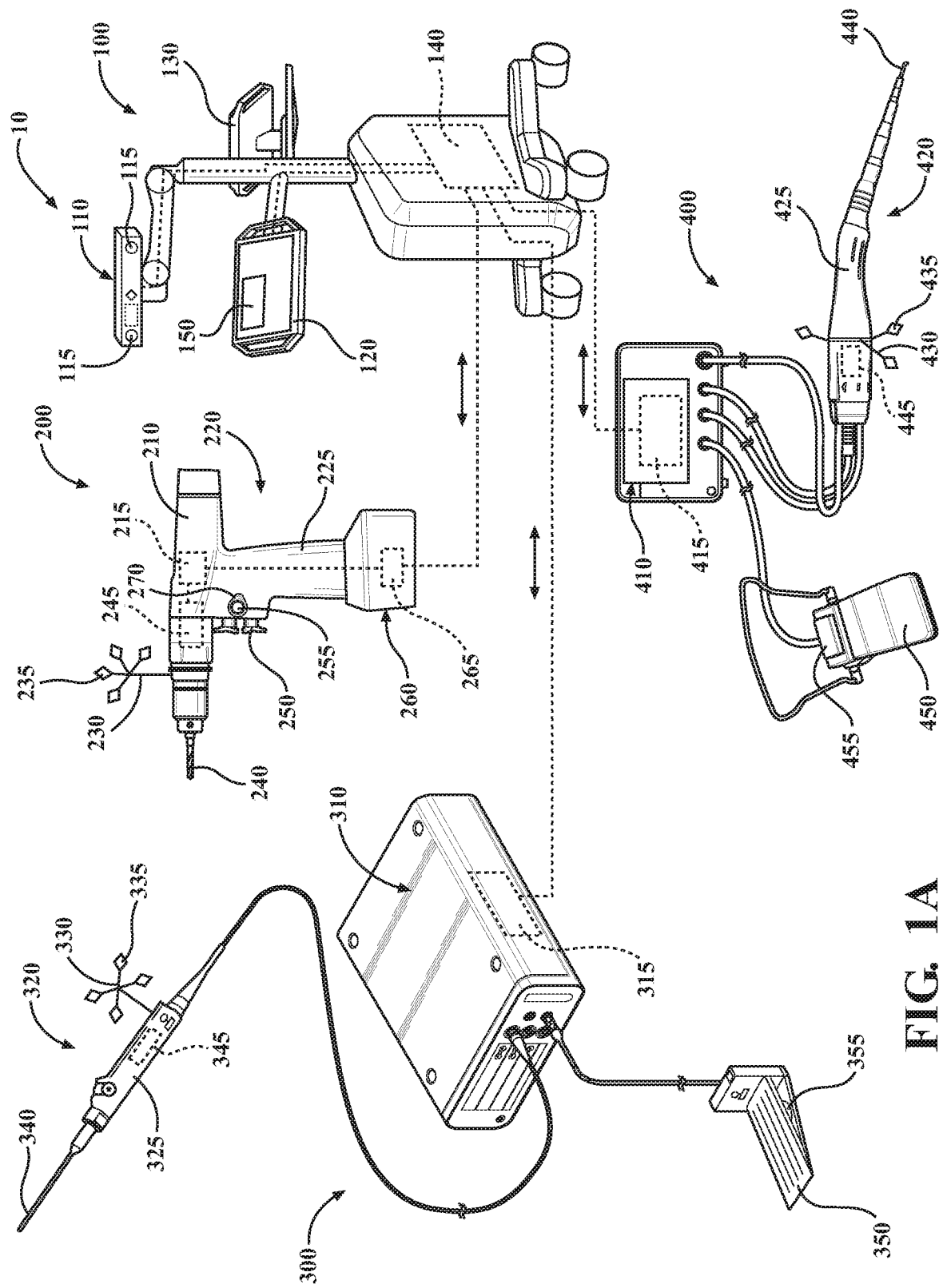
FIG. 1A is a schematic view of a surgical system including a plurality of surgical instrument assemblies and a surgical navigation system for tracking a surgical instrument associated with each of the various surgical instrument assemblies.
Figure 1B:
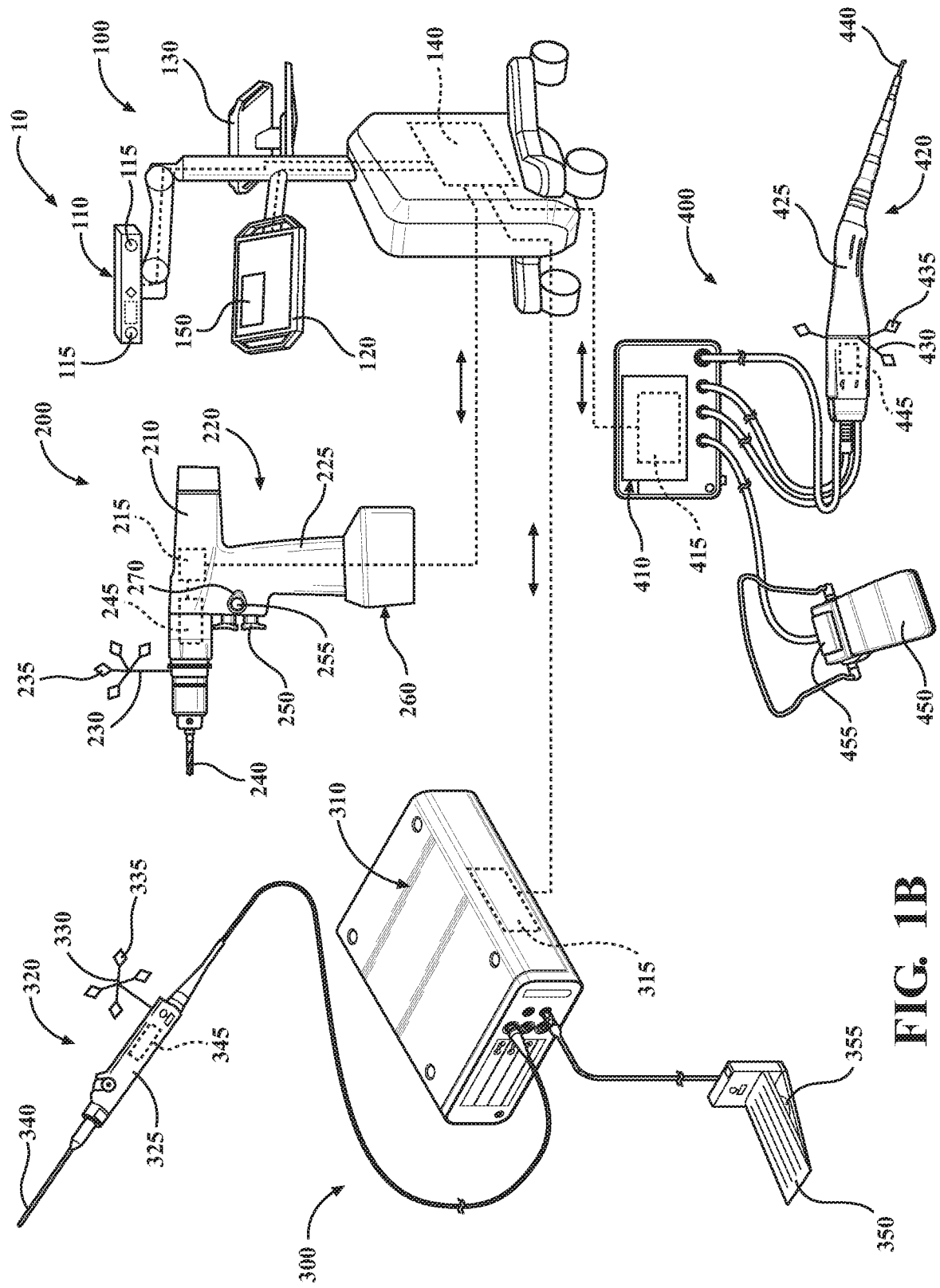
FIG. 1B is a schematic view of an alternative configuration of the surgical system of FIG. 1A.

Accordingly, FIGS. 1A and 1B illustrate an exemplary surgical system 10 that may comprise a surgical navigation system 100 for tracking one or more surgical instrument assemblies 200, 300, 400 including a surgical instrument 220, 320, 420 to assist the medical professional, such as a surgeon, in executing a medical procedure.

The surgical navigation system 100 may comprise a navigation interface that includes one or more display units 120, one or more user inputs 130, such as one or more graphical user interfaces (GUI) 150. The display unit 120 of the surgical navigation system 100 may be configured to display various prompts or data entry boxes. For example, the display unit 120 may be configured to display a text box or prompt that allows the surgeon to manually enter or select the type of surgical procedure to be performed. The display unit 120 may also be configured to display patient data, such as a pre-operative image or scan. As described above, the pre-operative image may be based on MRI scans, radiological scans or computed tomography (CT) scans of the patient's anatomy. The preoperative image may be uploaded to the surgical navigation system 100 and displayed on the display unit 120. The display unit 120 may be further configured to display a surgical plan for a medical procedure overlaid on the patient data or image.

The surgical plan may include the surgical pathway for executing the medical procedure or planned trajectory or orientation for the medical instrument during the medical procedure. The surgical plan may also include overlaying the position and/or orientation of an implant or medical device to be inserted during the medical procedure on the patient data or image. It is contemplated that the surgical navigation system 100 may comprise a display unit 120 configured to display and/or project a holographic image of surgical pathway for executing the medical procedure or planned trajectory or orientation for the medical instrument during the medical procedure. This may include projecting the surgical pathway onto the patient or other surface in the operating room. It may also include a projection of the surgical pathway onto the head unit worn by the surgeon, such as a lens, shield, or glasses of the head unit. An exemplary configuration of surgical navigation system 100 including a display unit worn by the surgeon to display the target trajectory and/or target location is disclosed in International Patent Application No. PCT/IB2018/053130, the entirety of which is hereby incorporated by reference.

The user input 130 and/or the graphical user interface (GUI) 150 may be configured to allow the surgeon to input or enter patient data or modify the surgical plan. The patient data may comprise patient images, such as pre-operative images of the patient's anatomy. These images may be based on MRI scans, radiological scans or computed tomography (CT) scans of the patient's anatomy. The patient data may also include additional information related to the type of medical procedure being performed, the patient's anatomical features, the patient's specific medical condition, and/or operating settings for the surgical navigation settings. For example, in performing a spinal surgery, the surgeon may enter information via the user input 130 and/or the graphical user interface (GUI) 150 related to the specific vertebra on which the medical procedure is being performed. The surgeon may also input various anatomical dimensions related to the vertebrae and/or the size and shape of a medical device or implant to be inserted during the medical procedure. The user input 130 and/or the graphical user interface (GUI) 150 may also be configured to allow the surgeon to select, edit or manipulate the patient data. For example, the surgeon may identify and/or select anatomical features from the patient data. This may include selecting the surgical site, such as selecting the vertebra and/or specific area on the vertebra where the medical procedure is to be performed.

The surgeon may also be able to identify critical anatomical features, such as anatomical features that the surgeon may want to either target or avoid during the medical procedure. For example, the surgeon may use the user input 130 and/or the graphical user interface (GUI) 150 to select, cortical walls, nerves, blood vessels or similar critical anatomical structures that the surgeon wishes to avoid and establish zones surrounding those anatomical structures. The surgeon may also use the user input 130 and/or the graphical user interface (GUI) 150 to select and/or input a target location, target trajectory, target depth or similar feature of the surgical pathway to help guide the surgeon in performing the medical procedure.

The system may be configured to utilize segmentation to facilitate zones and/or boundaries of interests. This segmentation may be performed automatically, semi-automatically, or manually.

In one example of manual segmentation, the surgeon may also utilize the user input 130 and/or the graphical user interface (GUI) 150 to define a geometric primitive to define a region of interest. A method of defining geometric primitives for the purpose of segmentation and visualization of cavities or orifices of the human body may comprise the steps of: manual pre-segmentation by defining enclosing geometric primitives in a 3D patient image for generating initial envelopes; analyzing the anatomy within pre-segmented geometric primitives; using the result of the analysis for adjustment of the envelopes; and visualizing the envelopes. The adjustment of a visualized envelope can be based on analyzed anatomy using computed voxel affiliations and the adjustment of a visualized cell envelope may be achieved by computing a surface mesh of the voxels which are affiliated completely and/or partially to the cell. Further, the adjustment of a visualized envelope may be achieved by optimizing type, orientation, position and/or size of the enclosing geometric primitive. Exemplary methods and systems for defining a geometric primitive and guiding a surgical instrument are disclosed in U.S. patent application Ser. No. 15/300,414 and U.S. patent application Ser. No. 15/582,637, both of which are hereby incorporated by reference in their entirety.

The user input 130 and/or the graphical user interface (GUI) 150 may also be configured to input the surgical plan. This may include selecting the surgical instrument to be used and the device and/or implant to be inserted. It may also include identify a position and/or orientation (i.e., pose) where the device or implant is to be placed within the patient. The user input 130 and/or the graphical user interface (GUI) 150 may also to allow the surgeon to select the parameters of the implant to be inserted, such as the length and/or diameter of the screw to be inserted.

The surgical navigation system 100 may further comprise a navigation processor 140. The navigation processor 140 can be located on a personal computer or laptop computer. The navigation processor 140 may be in communication with the user input 130, display unit 120, central processing unit (CPU) and/or other processors, memory (not shown), and storage (not shown). The navigation processor 140 may further comprise software and/or operating instructions related to the operation of the surgical navigation system 100 and to implement the various routines and/or methods disclosed herein. The software and/or operating instructions may comprise a planning system configured to define an accurate position and/or angular alignment of an implant in relation to the patient 20. The navigation processor 140 may be in wired or wireless communication with the surgical instrument assemblies 200, 300, 400, directly or indirectly.

The navigation system may further comprise software employed by the navigation processor 140 to control operation of the surgical instruments 220, 320, 420. The software may include a boundary and/or alert zone generator. The boundary generator may be implemented on the navigation processor 140, the instrument processor 215, 315, 415, and/or on other components, such as on a separate processor or controller. An exemplary system for and method of boundary generation may be found in U.S. Patent Publ. No. 2004/0034283A1, which is hereby incorporated in by reference in its entirety. The boundary generator may also be part of a separate system that operates remotely from the surgical instruments 220, 320, 420. The boundary generator is a software program or module that generates one or more virtual boundaries for constraining movement and/or operation of the surgical instruments 220, 320, 420. In some examples, the boundary generator provides virtual boundaries that define a virtual drill and/or driver guide (e.g., a virtual implant planning guide). The virtual boundaries or alert zones may also be provided to control operation of the surgical instruments 220, 320, 420 relative to critical anatomical features that the surgeon wishes to avoid, target depths and/or target positions. The virtual boundaries may be one-dimensional (1D), two-dimensional (2D), three-dimensional (3D), and may comprise a point, line, axis, trajectory, plane (an infinite plane or plane segment bounded by the anatomy or other boundary), volume or other shapes, including complex geometric shapes. The virtual boundaries may be represented by pixels, point clouds, voxels, triangulated meshes, other 2D or 3D models, combinations thereof, and the like. U.S. Patent Publication No. 2018/0333207 and U.S. Pat. No. 8,898,043 are incorporated by reference, and any of their features may be used to facilitate planning or execution of the surgical procedure. A plurality of boundaries may be used to define zones.

The virtual boundaries may be used in various ways. For example, the navigation processor 140 may/or control certain operations/functions of the surgical instruments 220, 320, 420 based on a relationship of the surgical instruments 220, 320, 420 to the boundary (e.g., spatial, velocity, etc.). Other uses of the boundaries are also contemplated.

Boundaries to ensure that instruments are positioned at the desired depth may be defined by a virtual planar boundary, a virtual volumetric boundary, or other forms of virtual boundary. Virtual boundaries may also be referred to as virtual objects. The virtual boundaries may be defined with respect to an anatomical model, such as a 3D bone model. In other words, the points, lines, axes, trajectories, planes, volumes, and the like, that are associated with the virtual boundaries may be defined in a coordinate system that is fixed relative to a coordinate system of the anatomical model such that tracking of the anatomical model (e.g., via tracking the associated anatomy to which it is registered) also enables tracking of the virtual boundary.

The anatomical model is registered to the first patient tracker such that the virtual boundaries become associated with the anatomical model and associated coordinate system. The virtual boundaries may be implant-specific, e.g., defined based on a size, shape, volume, etc. of an implant and/or patient-specific, e.g., defined based on the patient's anatomy. The virtual boundaries may be boundaries that are created pre-operatively, intra-operatively, or combinations thereof. In other words, the virtual boundaries may be defined before the surgical procedure begins, during the surgical procedure (including during tissue removal), or combinations thereof. The virtual boundaries may be provided in numerous ways, such as by the navigation processor 140 creating them, receiving them from other sources/systems, or the like. The virtual boundaries may be stored in memory for retrieval and/or updating.

It is further contemplated that in some cases, the virtual boundaries may comprise multiple planar boundaries that can be used to delineate multiple target depths (e.g., three target depths) for separate instruments to be used in a single procedure. For example, a first virtual boundary representing target depth for a drill to bore the hole, a second virtual boundary representing target depth for the tap, and a third virtual boundary representing target depth for the driver to insert the screw, as are illustrated in FIG. 5D and will be explained in greater detail below. These multiple virtual boundaries can be activated, one at a time, by the navigation processor 140 to constrain cutting to one plane at a time. The navigation processor 140 track the state of the surgical instruments 220, 320, 420 relative to the virtual boundaries.

The surgical navigation system 100 may also comprise a tracking unit 110 including one or more sensors 115. The sensors may comprise cameras, such as CCD cameras, CMOS cameras, and/or optical image cameras, magnetic sensors, radio frequency sensors, or any other sensor adapted to detect and/or sense the position of a tracking device 230, 330, 430 of the surgical instrument assemblies 200, 300, 400. Description of a suitable tracking unit, and the various localizers that it can utilize may be found in U.S. Patent Publication No. 2017/0333137, which is hereby incorporated by reference in its entirety.

Referring to FIGS. 1A-1B, various exemplary surgical instrument assemblies 200, 300, 400 are illustrated in communication with the surgical navigation system 100. Each of the various exemplary surgical instrument assemblies will be described in greater detail below. The surgical instruments assemblies 200, 300, 400 may be configured to be in wired and/or wireless communication with the surgical navigation system 100. Furthermore, each of the surgical instrument assemblies 200, 300, 400 may have a number of similar components capable of performing similar functions and/or operations. Similar components between each of the various surgical instrument assemblies 200, 300, 400 will include the same two-digit number with a leading 2, 3, or 4 to reflect the associated surgical instrument assembly 200, 300, 400. For example, each of the surgical instrument assemblies 200, 300, 400 may include a surgical instrument 220, 320, 420.

The surgical system 10 may comprise a first surgical instrument assembly 200 in communication with the navigation system 100. For example, the first surgical instrument assembly 200 may be configured as a first surgical instrument 220, such as a surgical drill or driver, including a handpiece 225. The handpiece 225 may comprise a housing 210 configured to house the components of the first surgical instrument 220. The handpiece 225 may be shaped to define a handle or grip portion for the surgeon to hold while performing a medical procedure. Suitable handpieces are described in U.S. Pat. No. 5,747,953, which is hereby incorporated by reference in its entirety.

The first surgical instrument 220 may further comprise a first instrument processor 215 and a motor 245. Each of the first instrument processor 215 and the motor 245 may be disposed within the handpiece 225 of the first surgical instrument 220. The first instrument processor 215 and the motor 245 may be in communication with one another, and the first instrument processor 215 may be configured to control the operation of the motor 245, and by extension the first surgical instrument 220. For example, the first surgical instrument 220 may comprise a end-effector 240, such as a drill bit for boring a hole or a driver for inserting a screw. The end-effector 240 may be coupled to the handpiece 225 of the first surgical instrument 220 such that the motor 245 may be operably coupled to the end-effector 240. For example, the motor 245 may be configured to rotate a drill bit 240 to bore a hole and/or remove biological tissue. The first instrument processor 215 may be in communication with the motor 245 and configured to control operation of the motor 245, and by extension the drill bit 240. The first instrument processor 215 may also be in communication with the navigation processor 140 and configured to exchange data related to the position and/or orientation of the first surgical instrument 220, as well as data related to the operation of the first surgical instrument 220. For example, the first instrument processor 215 and the navigation processor 140 may be configured to communicate data between one another related to the operation of the first surgical instrument 220 based on the position and/or orientation of the first surgical instrument 220 as detected by the surgical navigation system 100.

The first surgical instrument assembly 200 may also comprise a power source 260. The power source 260 may be removably coupled to the handpiece 225 of the surgical drill 220. For example, the power source 260 may comprise a removable battery pack. It is also contemplated that the power source 260 may be formed as part of, or disposed within, the handpiece 225 of the first surgical instrument 220. The power source 260 may be in electrical communication with the first instrument processor 215 and/or the motor 245 and configured to selectively provide power to the motor 245 to rotate the end-effector 240. The power source may also be a surgical console providing power to the first surgical instrument with a cord.

In instances where the power source takes the form of a removable battery pack, the power source 260 may further comprise a processor 265. The processor 265 may be in communication within the first instrument processor 215 via power signals and/or data signals. The processor 265 and the first instrument processor 215 may be configured to communicate between one another to control operation of the motor 245, and by extension the first surgical instrument 220. For example, the processor 265 in the power source 260 may be configured to identify when the power source 260 has dropped below a threshold charge level such that the power source 260 may be unable to continue operating the motor 245 at a minimum threshold for boring a hole or cutting biological tissue. The processor 265 may be configured to cut off all power to the first instrument processor 215 and/or the motor 245 to prevent operation of the end-effector 240 until the power source 260 has a sufficient charge level to operate the motor 245 at a rate above the minimum threshold for boring a hole or cutting biological tissue. The processor 265 in the power source 260 may also be in wireless communication with the navigation processor 140. The power source 260 may comprise a transceiver configured to send and receive signals between the power source 260 and the surgical navigation system 100 and/or the instrument processor 215.

The processor 265 and the navigation processor 140 may be configured to communicate data between one another related to the operation of the first surgical instrument 220 based on the position and/or orientation of the first surgical instrument 220 as detected by the surgical navigation system 100. For example, the navigation system 100 may be configured to communicate data to the processor 265 including instructions for the processor 265 to discontinue providing energy to the first instrument processor 215 and/or the motor 245 based on the position and/or orientation of the first surgical instrument 220 as detected by the surgical navigation system 100. The navigation system 100 may also be configured to communicate data to the processor 265 including instructions for the processor 265 to continue and/or resume providing energy to the first instrument processor 215 and/or the motor 245 based on the position and/or orientation of the first surgical instrument 220 as detected by the surgical navigation system 100.

The first surgical instrument assembly 200 may also comprise a switch 250, such as a trigger or button or lever, that is operably coupled to the first instrument processor 215. The switch 250 may be configured to be manipulatable by the medical professional to control energization of the variable speed motor 245. For example, the switch 250 may be manipulatable between a first position, a deenergized state, and a second position, an energized state. The first surgical instrument assembly 200 may also comprise a switch sensor that is configured to detect the position of the switch 250 and produce and/or communicate a signal indicative of the position of the switch 250 to the first instrument processor 215 based on a user's manipulation of the switch 250 to control the operation of the first surgical instrument 220. For example, the switch 250 may comprise a first position, a second position and a plurality of intermediary positions between the first and second positions. The first position may be configured as an off position, such that when the first instrument processor 215 receives a signal that the switch sensor has detected that the switch 250 is in the first position, the first instrument processor 215 prevents the flow of energy from the power source 260 to the motor 245, preventing the operation of the first surgical instrument 220. Alternatively, when the first instrument processor 215 receives a signal that the switch sensor has detected that the switch 250 is in the second position, the first instrument processor 215 may be configured to allow maximum flow of energy from the power source 260 to the motor 245, allowing the first surgical instrument 220 to operate at a maximum drilling or cutting speed. When the first instrument processor 215 receives a signal that the switch sensor has detected that the switch 250 is in one of the intermediary positions, the first instrument processor 215 may be configured to allow the flow of energy from the power source 260 to the motor 245 at a level corresponding to the position of the switch 250 between the first and second positions, allowing the first surgical instrument 220 to operate at an intermediate drilling or cutting speed. For example, if the first instrument processor 215 receives a signal that the switch sensor has detected that the switch 250 is positioned half-way (50%) between the first and second positions, the first instrument processor 215 may be configured to allow the flow of energy from the power source 260 to the motor 245 at a level that allows the first surgical instrument 220 to operate at a rate of 50% of the maximum drilling or driving speed. Alternatively, the first instrument processor 215 may be configured to allow the maximum flow of energy from the power source 260 to the motor 245 whenever the switch 250 is in a position other than the first position, allowing the first surgical instrument 220 to operate at the maximum drilling or cutting speed when the switch 250 is in the second position or any of the intermediary positions. An exemplary switch sensor may be found in U.S. Pat. No. 9,295,476, which is hereby incorporated in by reference in its entirety.

The first surgical instrument assembly 200 may also comprise a first alert device 255. The first alert device 255 may comprise an audible, a tactile, and/or a visually perceptible device. The first alert device 255 may be configured to be in communication with the first instrument processor 215 or the processor of the power source 260. The first instrument processor 215 or other processor may be configured to send a signal to activate the first alert device 255 to provide a warning or notification based on a pre-programmed condition or setting.

For example, as described above, the surgeon may use the user input 130 to enter defined conditions and/or settings into the surgical navigation system 100, such as selecting cortical walls, nerves, blood vessels, or similar anatomical structures that the surgeon wishes to avoid and establish regions or zones surrounding those anatomical structures. The surgeon may also use the user input 130 to select and/or input a target location (position(s)), target trajectory in one or more degree of freedoms, or no-cut zones, or similar features of the surgical pathway to help guide the surgeon in performing the medical procedure. The first instrument processor 215, based on data provided by the navigation processor 140, may be configured to send a signal to activate the first alert device 255 upon the end-effector 240 of the first surgical instrument 220 entering one of the regions and/or zones, as defined by the surgeon. The first instrument processor 215 or other processor, based on data provided by the navigation processor 140, may also be configured to send a signal to activate the first alert device 255 upon the end-effector 240 of the first surgical instrument 220 being off trajectory and/or upon the end-effector 240 reaching the target location.

In an exemplary configuration, the first alert device 255 may comprise a vibrating device that is placed in contact with the surgeon and configured to vibrate to notify the surgeon of a particular condition or to provide a warning. In an exemplary configuration, as illustrated in FIGS. 1A-1B, the first alert device 255 may comprise a vibrating device coupled to the switch 250 for controlling the operation of the first surgical instrument 220. The first alert device 255 may be configured to vibrate upon the occurrence of a defined condition. As the surgeon would be in constant contact with the switch 250 when actuating the first surgical instrument 220, the surgeon would feel the first alert device 255 vibrate and be notified of the occurrence of a defined condition. The first alert device 255 may be configured to produce a vibration in a specific pattern or interval upon the occurrence of the defined condition. Alternatively, the first alert device 255 may be configured to produce a first vibration in a specific pattern or interval upon the occurrence of a first condition and produce a second vibration in a different pattern or interval upon the occurrence of a second condition.

The first alert device 255 may also be configured as an audible device, such as a speaker, configured to provide an audible alert to the surgeon upon the occurrence of the defined condition. For example, the first alert device 255 may comprise a speaker configured to produce a specific sound upon the occurrence of the defined condition. Alternatively, the first alert device 255 may comprise a speaker configured to produce a sound in a specific pattern or interval upon the occurrence of the defined condition. The speaker may be included as part of the surgical navigation system.

In yet another configuration, the first alert device 255 may be configured as a visually perceivable device or indicator, such as a visual display, configured to provide a visual alert to the surgeon upon the occurrence of the defined condition. For example, the first alert device 255 may comprise a light configured to blink upon the occurrence of the defined condition. Alternatively, the first alert device 255 may comprise a plurality of multi-colored lights configured to light up and/or blink in a defined color or pattern upon the occurrence of the defined condition. In instances where the first alert device is a display, the display may be configured to generate visual cues to indicate an alert condition. The navigation display 120 may be utilized as the display for the first alert device 255 such that the navigation display 120 is configured to provide a visual cue to alert the surgeon. For example, the navigation display 120 may be configured to display a prompt or window when the first alert device 255 is triggered providing a notification to the surgeon. Alternatively, the navigation display 120 be configured to flash and/or change color when the first alert device is triggered. One of the many advantages of utilizing the navigation display 120 as the display of the first alert device 255 is that the surgeon will already be regularly watching the navigation display 120 during execution of the procedure, so the surgeon is likely to receive the visual notification promptly if the navigation display 120 is configured to display the notification provided by the first alert device 255.

The removable power source 260 may also include the first alert device in certain configurations. For example, the removable power source 260 may include a vibratory motor or a speaker responsive to signals generated by the navigation processor.

It is also contemplated that the first alert device 255 may include a combination of audible, tactile, and/or visually perceptible devices. For example, the first alert device 255 may be configured as a combination of an audible device and a tactile device, such that the tactile device may be configured to vibrate to provide a first alert and the audible device may be configured to produce a noise to provide a second alert. The first and second alerts may be indicative of an occurrence of the same defined conditions, or the first and second alerts may indicative of an occurrence of distinct defined condition. For example, the first alert may be based on the first surgical instrument 220 being misaligned with the target trajectory, and the second alert may be based on the end-effector 240 reaching the target location.

While the first alert device 255 is illustrated as being coupled to or proximate the switch 250 of the first surgical instrument assembly 200, it is contemplated that the first alert device 255 may be coupled to and/or positioned in alternative positions. For example, when the first alert device 255 comprises a tactile device, the first alert device 255 may be configured as a vibrating member that is removably attached to the surgeon. The first alert device 255 may be configured as a wearable device, such as a bracelet to be worn on the surgeon's wrist or arm so that the surgeon would be able to feel the first alert device 255 vibrating upon the occurrence of the defined condition. Alternatively, when the first alert device 255 comprises an audible device, the first alert device 255 may be configured as a speaker that is removably attached to the surgeon. The first alert device 255 may be configured as a blue-tooth speaker or earpiece to be worn on the surgeon's head or positioned within the surgeon's ear so that the surgeon would be able to hear the first alert device 255 producing a noise upon the occurrence of the defined condition.

While not required, there are a number of advantages to positioning the first alert device 255 away from the first surgical instrument 220. For example, one advantage of positioning the first alert device 255 away from the first surgical instrument 220 is that it may reduce the size of the first surgical instrument 220. This may allow for the first surgical instrument 220 to fit in smaller spaces. A smaller first surgical instrument 220 may also provide a less obstructed view of the surgical site for the surgeon. Another advantage of positioning the first alert device 255 away from the first surgical instrument 220, particularly in the case of a tactile device, is that the first alert device 255 will not vibrate or impact the movement of the first surgical instrument 220 while still providing an alert or notification to the surgeon. During highly technical procedures, an alert that vibrates the first surgical instrument 220 may be likely to cause the surgeon to move the first surgical instrument 220 in an undesirable position as a result of being startled by the first alert device 255 and/or the vibration imparting an undesirable movement to the first surgical instrument 220.

The first surgical instrument assembly 200 may also comprise a tracking device 230. The tracking device 230 may be coupled to the handpiece 225 of the first surgical instrument 220. The tracking device 230 may comprise a plurality of markers 235 that are identifiable by the tracking unit 110 of the surgical navigation system 100. The markers 235 may comprise passive tracking elements (e.g., reflectors) for transmitting light signals (e.g., reflecting light emitted from the tracking unit 110) to the sensor(s) 115. In other configurations, the markers 235 may be configured as active tracking markers. It is also contemplated that the markers 235 may comprise a combination of active and passive arrangements. The markers 235 may be arranged in a defined or known position and orientation relative to the other markers 235 in order to allow the surgical navigation system 100 to determine the position and orientation (pose) of the surgical instrument 220. For example, the markers 235 may be registered to the first surgical instrument 220 to allow the surgical navigation system 100 to determine the position and/or orientation of a end-effector 240 or cutting portion of the first surgical instrument 220 within a defined space, such as the surgical field. In one exemplary configuration, the surgical navigation system 100 may be configured to determine the position and/or orientation of the end-effector 240 or cutting portion of the second surgical instrument 220 or relative to the target trajectory and/or the target location of the planned surgical pathway. In another exemplary configuration, the surgical navigation system 100 may also be configured to determine the position and/or orientation of the end-effector 240 or cutting portion of the second surgical instrument 220 or relative to critical anatomical structures within the patient's body, as well as relative to user-defined boundaries, zones, and/or regions.

The surgical system 10 may alternatively comprise a second surgical instrument assembly 300 to be used with the navigation system 100. For example, the second surgical instrument assembly 300 may comprise a second surgical instrument 320, such as a high-speed surgical bur or ultrasonic surgical handpiece, including a handpiece 325. The handpiece 325 may be coupled to a console 310 that is configured to control the operation of various components of the second surgical instrument 320. The handpiece 325 may be shaped to define a handle or grip portion for the surgeon to hold while performing a medical procedure. Exemplary second surgical instruments that connect to consoles may be found in U.S. Pat. No. 10,016,209 and U.S. Patent Publication No. 20190117322, which are each hereby incorporated in by reference in their entirety.

The second surgical instrument 320 may further comprise a second instrument processor 315 and a motor 345. The second instrument processor 315 may be disposed within the console 310 of the second surgical instrument assembly 300. The motor 345 may be disposed within the handpiece 325 of the second surgical instrument 320. The second instrument processor 315 and the motor 345 may be in communication with one another and the second instrument processor 315 may be configured to control the operation of the motor 345, and by extension the second surgical instrument 320. For example, the second surgical instrument 320 may be coupled to the console by a cord connecting the second instrument processor 315 to the motor 345 to allow communication between the second instrument processor 315 to the motor 345 to control operation of the motor. The second instrument processor 315 may also comprise a end-effector 340, such as a high-speed cutting bur or ultrasonic tip. The end-effector 340 may be coupled to the handpiece 325 of the second surgical instrument 320 such that the motor 345 may be operably coupled to the end-effector 340. For example, the motor 345 may be configured to actuate the high-speed cutting bur 340 to grind and/or remove biological tissue from the surgical site or to vibrate the ultrasonic tip. The second instrument processor 315 may be in communication with the motor 345 and configured to control the operation of the motor 345, and by extension the high-speed cutting bur 340. The second instrument processor 315 may also be in communication with the navigation processor 140 and configured to exchange data related to the position and/or orientation of the second surgical instrument 320, as well as data related to the operation of the second surgical instrument 320. For example, the second instrument processor 315 and the navigation processor 140 may be configured to communicate data between one another related to the operation of the second surgical instrument 320 based on the position and/or orientation of the second surgical instrument 320 as detected by the surgical navigation system 100. It is also contemplated that additional surgical instruments may be coupled the console and/or in communication with the second instrument processor 315 disposed within the console 310.

The second surgical instrument assembly 300 may also comprise a power source (not shown). The power source may be coupled to the console 310 of the second surgical instrument assembly 300 and configured to provide energy to the motor 345 of the second surgical instrument 320 to actuate the end-effector 340. It is also contemplated that the console 310 may be comprise a cord configured to be plugged into an outlet that is connected to an electrical grid for supplying energy to the second surgical instrument assembly 300. The power source may be in electrical communication with the second instrument processor 315 and/or the motor 345 and configured to selectively provide power to the motor 345 to actuate the end-effector 340.

The second surgical instrument assembly 300 may also comprise a switch 350, such as a footswitch, trigger or button, that is operably coupled to the second instrument processor 315. The switch 350 may be configured to produce and/or communicate a signal to the second instrument processor 315 based on a user input to control the operation of the second surgical instrument 320. For example, the switch 350 may comprise a first position, a second position and a plurality of intermediary positions between the first and second positions. The first position may be configured as an off position, such that when the first instrument processor 315 detects that the switch 350 is in the first position, the first instrument processor 315 prevents the flow of energy from the power source to the motor 345, preventing the operation of the second surgical instrument 320. Alternatively, when the first instrument processor 315 detects that the switch 350 is in the second position, the second instrument processor 315 may be configured to allow maximum flow of energy from the power source to the motor 345, allowing the second surgical instrument 320 to operate at a maximum speed or displacement, such as maximum cutting speed or grinding speed or vibrating speed or vibrating amplitude. When the second instrument processor 315 detects that the switch 350 is in one of the intermediary positions, the second instrument processor 315 may be configured to allow the flow of energy from the power source to the motor 345 at a level corresponding to the position of the switch 350 between the first and second positions, allowing the second surgical instrument 320 to operate at an intermediate cutting or grinding speed. For example, if the second instrument processor 315 detects that the switch 350 is positioned half-way (50%) between the first and second positions, the second instrument processor 315 may be configured to allow the flow of energy from the power source to the motor 345 at a level that allows the second surgical instrument 320 to operate at a rate of 50% of the maximum cutting or grinding speed. Alternatively, the second instrument processor 315 may be configured to allow the maximum flow of energy from the power source to the motor 345 whenever the switch 350 is in a position other than the first position, allowing the second surgical instrument 320 to operate at the maximum cutting or grinding speed when the switch 350 is in the second position or any of the intermediary positions.

While not illustrated in the figures, it is contemplated that a plurality of surgical instrument 320 may be coupled to the console 310 and controlled by a footswitch. The switch 350, such as a footswitch, may be configured to control each of the plurality of surgical instruments. For example, a single footswitch may comprise a plurality of buttons, each of which may assigned to one of the plurality of surgical instruments. An exemplary surgical system including a switch connected to a console for controlling a plurality of surgical instruments is disclosed in U.S. patent application Ser. No. 15/450,477, which is incorporated in its entirety.

The second surgical instrument assembly 300 may also comprise a second alert device 355. The second alert device 355 may comprise an audible, a tactile, and/or a visually perceptible device. The second alert device 355 may be configured to be in communication with the second instrument processor 315 or directly with the navigation processor. The second instrument processor 315 or navigation processor may be configured to send a signal to activate the second alert device 355 to provide a warning or notification based on a pre-programmed condition or setting.

For example, as described above, the surgeon may use the user input 130 to enter defined conditions and/or settings into the surgical navigation system 100, such as selecting cortical boundaries, nerves, blood vessels, or similar anatomical structures that the surgeon wishes to avoid and establish boundaries or zones surrounding those anatomical structures. The surgeon may also use the user input 130 to select and/or input a target location, target trajectory, or similar features to help guide the surgeon in performing the medical procedure. The second instrument processor 315, based on data provided by the navigation processor 140, may be configured to send a signal to activate the second alert device 355 upon the end-effector 340 of the second surgical instrument 320 entering one of the regions and/or zones, as defined by the surgeon, that surround an anatomical structure. For example, the surgeon may utilize the user input 130 of the surgical navigation system 100 to define a boundary or zone relative to the anatomical model. This may include identifying a critical anatomical feature such as a particular wall of the vertebral body, the central foramen, a nerve or blood vessel and assigning it a zone. The navigation system 100, as described above, may comprise a boundary generator for generating virtual boundaries within the patient relative to critical anatomical feature. As part of generating those boundaries, the navigation system 100 may be configured to recognize and/or define the virtual boundaries based on the segmentation algorithm. Upon the navigation system 100 generating one or more virtual boundaries, the navigation system 140 may be further configured to allow the surgeon to select a depth or distance. Upon the surgeon selecting a depth, the navigation system 100 may be configured to project a second virtual boundary at the selected depth or distance from the original virtual boundary. The area and/or volume defined between the original virtual boundary and the second virtual boundary may define at least portion of the zone. An exemplary system and/or method of segmentation may be found in U.S. Patent Publ. No. 2017/0061242A1, which is hereby incorporated in by reference in its entirety.

It may also comprise identifying additional zones that include regions or areas surrounding the critical anatomical feature, such as defining a second zone encircling the critical anatomical feature that is spaced a distance from the boundary of the critical anatomical feature. It may also include defining additional subsequent zones, such as a third zone encircling the second zone and is spaced a distance from the boundary of the critical anatomical feature that is greater than the distance the second zone is spaced from the critical anatomical feature. In this exemplary configuration, the end-effector 340 is likely to contact the outermost alert zone first, triggering the second alert device 355 to produce a first alert. The end-effector 340 may then contact the next alert zone closest to the critical anatomical structure, triggering the alert device 355 to produce a second alert. The first and second alerts configured to notify the surgeon of the occurrence of the end-effector 340 entering the respective alert zones assigned to the first and second alerts. The surgical navigation system 100 may be configured to allow the surgeon to define the alert zone(s) or region(s) as needed for the specific procedure. The alert zones may be configured as boundary lines or as regions encircling the critical anatomical structure. For example, the alert zone(s) may comprise a region or layer encircling the critical anatomical structure. The surgeon may define the thickness of the alert zone in the surgical navigation system 100. For example, a second alert zone located adjacent the critical anatomical structure may be defines as a two-millimeter-thick region surrounding the critical anatomical structure. The thickness may be varied based on the type of procedure and/or the surgeon's preference to ensure that the critical anatomical structure is not contacted. The surgeon may define a subsequent alert zone may adjacent the second alert zone and opposite the critical anatomical structure, such that the subsequent alert zone is further from the critical anatomical structure than the second alert zone.

The surgeon may define the subsequent alert zone as a five-millimeter-thick region encircling the outermost perimeter of the second alert zone. The thickness through manipulation of a user input device based on the type of procedure and/or the surgeon's preference.

It should be appreciated that these alert zones may be automatically generated based on segmentation data from the patient scan.

The second instrument processor 315, based on data provided by the navigation processor 140, may also be configured to send a signal to activate the second alert device 355 upon the end-effector 340 of the second surgical instrument 320 being off trajectory and/or upon the end-effector 340 reaching the target location/zone/boundary. For example, the second alert device 355 may be activated to produce at least one of an audible, a tactile, or a visually perceptible alert based on the surgical navigation system 100 identifying that the end-effector 340 and/or the second surgical instrument 320 are not properly aligned with the target trajectory established as part of the panned surgical pathway. In this exemplary configuration, the second alert device 355 may produce a tactile alert, such as vibrating the switch 350 or removable power source, to notify the surgeon that the end-effector 340 is not properly aligned with the target trajectory. Once the end-effector 340 is properly aligned with the target trajectory, the second alert device 355 may be deactivated. The second alert device 355 may be similarly configured to be activated to produce at least one of an audible, a tactile, or a visually perceptible alert based on the surgical navigation system 100 identifying that the end-effector 340 and/or the second surgical instrument 320 have reached a target location as defined by the surgeon. For example, the second alert device 355 may produce a tactile alert, such as vibrating the switch 350, to notify the surgeon that the end-effector 340 has reached the target location/zone, such as a preferred depth or position relative to a critical anatomical boundary. Once the end-effector 340 has reached the target location, it is also contemplated that the control console may be configured to deactivate the motor, and by extension the end-effector 340, to prevent the end-effector 340 from going beyond the target location/zone.

In an exemplary configuration, the second alert device 355 may comprise a vibrating device that is placed in contact with the surgeon and configured to vibrate to notify the surgeon of a particular condition or to provide a warning. In an exemplary configuration, as illustrated in FIGS. 1A-1B, the second alert device 355 may comprise a vibrating device coupled to the switch 350, such as a footswitch, for controlling the operation of the second surgical instrument 320. The second alert device 355 may be configured to vibrate upon the occurrence of a defined condition. For example, the second alert device may include a vibrating device coupled to and/or in communication with the footswitch 350. In this configuration, the second alert device 355 may be configured to vibrate the footswitch 350 to notify the surgeon of the occurrence of a defined condition, such as the end-effector 340 of the second surgical instrument 320 approaching and/or entering one of the defined alert zones. As the surgeon would be in constant contact with the switch 350 when actuating the second surgical instrument 320, the surgeon would feel the second alert device 355 vibrate and be notified of the occurrence of a defined condition without affecting his or her grip on the handheld surgical instrument. The second alert device 355 may be configured to produce a vibration in a specific pattern or interval upon the occurrence of the defined condition. Alternatively, the second alert device 355 may be configured to produce a first vibration in a specific pattern or interval upon the occurrence of a first condition and produce a second vibration in a different pattern or interval upon the occurrence of a second condition. For example, the second alert device 355 may be configured to alternatingly vibrate and stop when the end-effector 340 of the second surgical instrument 320 approaches and/or enters a first alert zone, and the second alert device 355 may be configured to vibrate continuously when the end-effector 340 of the second surgical instrument 320 approaches and/or enters a second alert zone.

The second alert device 355 may also be configured as an audible device, such as a speaker, configured to provide an audible alert to the surgeon upon the occurrence of the defined condition. For example, the second alert device 355 may comprise a speaker configured to produce a specific sound upon the occurrence of the defined condition. Alternatively, the second alert device 355 may comprise a speaker configured to produce a sound in a specific pattern or interval upon the occurrence of the defined condition, such as the position of the end-effector crossing a defined zone/boundary.

In yet another configuration, the second alert device 355 may be configured as a visually perceivable device, such as a visual display, configured to provide a visual alert to the surgeon upon the occurrence of the defined condition. For example, the second alert device 355 may comprise a light configured to blink upon the occurrence of the defined condition. Alternatively, the second alert device 355 may comprise a plurality of multi-colored lights configured to light up and/or blink in a defined color or pattern upon the occurrence of the defined condition. The display may be integrated into the handpiece or the battery or as part of the navigation system, or combinations thereof.

It is also contemplated that the second alert device 355 may include a combination of audible, tactile, and/or visually perceptible devices. For example, the second alert device 355 may be configured as a combination of an audible device and tactile device, such that the tactile device may be configured to vibrate to provide a first alert and the audible device may be configured to produce a noise to provide a second alert. The first and second alerts may be indicative of an occurrence of the same defined conditions, or the first and second alerts may be indicative of an occurrence of distinct defined condition. For example, the first alert may be based on the second surgical instrument 320 entering a first region, and the second alert may be based on the end-effector 340 entering a second region.

While the second alert device 355 is illustrated as being coupled to the switch 350 of the second surgical instrument assembly 300, it is contemplated that the second alert device 355 may be coupled to and/or positioned in alternative positions. For example, when the second alert device 355 comprises a tactile device, the second alert device 355 may be configured as a vibrating member that is removably attached to the surgeon. The second alert device 355 may be configured as a bracelet to be worn on the surgeon's wrist or arm so that the surgeon would be able to feel the second alert device 355 vibrating upon the occurrence of the defined condition. Alternatively, when the second alert device 355 comprises an audible device, the second alert device 355 may be configured as a speaker that is removably attached to the surgeon. The second alert device 355 may be configured as a blue-tooth speaker or earpiece to be worn on the surgeon's head or positioned within the surgeon's ear so that the surgeon would be able to hear the second alert device 355 producing a noise upon the occurrence of the defined condition.

While not required, there are a number of advantages to positioning the second alert device 355 away from the second surgical instrument 320. For example, one advantage of positioning the second alert device 355 away from the second surgical instrument 320 is that it may reduce the size of the second surgical instrument 320. This may allow for the second surgical instrument 320 to fit in smaller spaces. A smaller second surgical instrument 320 may also provide a less obstructed view of the surgical site for the surgeon. Another advantage of positioning the second alert device 355 away from the second surgical instrument 320, particularly in the case of a tactile device, is that the second alert device 355 will not vibrate or impact the movement of the second surgical instrument 320 while still providing an alert or notification to the surgeon. In some medical procedures, the surgeon may rely on their feel and/or touch of the instrument to execute the procedure. For example, the surgeon may rely on the feel or touch of the instrument to recognize a change in torque, which may indicate a change in the consistency/density of the biological material being cut and/or removed. The surgeons feel and/or touch of the instrument may also indicate when the end-effector is spinning free compared to when it is cutting/removing biological material. In these exemplary circumstances, as well as others where the surgeons tough and/or feel for the instrument may assist them in accurate executing the medical procedure, it may be advantageous to the alert device 355 positioned away from the second surgical instrument 320, such as in a footswitch 350. During highly technical procedures, an alert device that vibrates being positioned on or proximate the second surgical instrument 320 may be likely to cause the surgeon to move the second surgical instrument 320 in an undesirable position as a result of being startled by the second alert device 355 and/or the vibration imparting an undesirable movement to the second surgical instrument 320. Vibrating the second surgical instrument 320 could also lead to the end-effector 340 grabbing or biting into the biological material causing an unwanted result, such as contacting a critical anatomical feature or removing/damaging biological material that was not intended to be removed during the medical procedure.

The second surgical instrument assembly 300 may also comprise a tracking device 330. The tracking device 330 may be coupled to the handpiece 325 of the second surgical instrument 320. The tracking device 330 be similar to as described above for the first surgical instrument assembly.

The surgical system 10 may comprise a third surgical instrument assembly 400 in communication with the navigation system 100. For example, the third surgical instrument assembly 400 may comprise a third surgical instrument 420, such as an ultrasonic instrument, including a handpiece 425. The handpiece 425 may be coupled to a console 410 that is configured to control the operation of various components of the third surgical instrument 420. The handpiece 425 may be shaped to comprise a handle or grip portion for the surgeon to hold while performing a medical procedure.

The third surgical instrument 420 may further comprise a third instrument processor 415 and a motor 445. The third instrument processor 415 may be disposed within the console 410 of the third surgical instrument assembly 400. The motor 445 may be disposed within the handpiece 425 of the third surgical instrument 420. The third instrument processor 415 and the motor 445 may be in communication with one another. The motor 445 may comprise a piezoelectric element configured to expand and contract upon the application of an electric current to the piezoelectric element. The piezoelectric element may comprise a plurality of disc-shaped piezoelectric elements arranged end to end in a stack. The third instrument processor 415 may be configured to control the operation of the motor 445, and by extension the third surgical instrument 420. For example, the third surgical instrument 420 may comprise a end-effector 440, such as an ultrasonic tip assembly. The end-effector 440 may comprise an ultrasonic tip assembly including a horn of which an ultrasonic tip portion vibrates at an ultrasonic wave velocity as the piezoelectric element(s) expand and contract. The ultrasonic tip assembly may also include an external sheath at least partially disposed over the horn except for the ultrasonic tip portion. The end-effector 440 may be coupled to the handpiece 425 of the third surgical instrument 420 such that the motor 445 may be operably coupled to the end-effector 440. For example, the motor 445 may be configured to actuate the ultrasonic tip assembly 440 to grind and/or remove biological tissue from the surgical site. The third instrument processor 415 may be in communication with the motor 445 and configured to control the flow of electric current to the piezoelectric element(s), controlling operation of the motor 445, and by extension the ultrasonic tip assembly 440. The third instrument processor 415 may also be in communication with the navigation processor 140 and configured to exchange data related to the position and/or orientation of the third surgical instrument 420, as well as data related to the operation of the third surgical instrument 420. For example, the third instrument processor 415 and the navigation processor 140 may be configured to communicate data between one another related to the operation of the third surgical instrument 420 based on the position and/or orientation of the third surgical instrument 420 as detected by the surgical navigation system 100.

The third surgical instrument assembly 400 may also comprise a power source (not shown). The power source may be coupled to the console 410 of the third surgical instrument assembly 400 and configured to provide energy to the motor 445 of the third surgical instrument 420 to actuate the end-effector 440. For example, the power source may comprise a removable battery pack. It is also contemplated that the console 410 may comprise a cord configured to be plugged into an outlet that is connected to an electrical grid for supplying energy to the third surgical instrument assembly 400. The power source may be in electrical communication with the third instrument processor 415 and/or the motor 445 and configured to selectively provide power to the motor 445 to actuate the end-effector 440.

The third surgical instrument assembly 400 may also comprise a switch 450, such as a footswitch, pedal or button, that is operably coupled to the third instrument processor 415. The switch 450 may be configured to produce and/or communicate a signal to the third instrument processor 415 based on a user input to control the operation of the third surgical instrument 420. For example, the switch 450 may comprise a first position, a second position and a plurality of intermediary positions between the first and second positions. The first position may be configured as an off position, such that when the third instrument processor 415 detects that the switch 450 is in the first position, the third instrument processor 415 prevents the flow of energy from the power source to the motor 445, preventing the operation of the third surgical instrument 420. Alternatively, when the first instrument processor 415 detects that the switch 450 is in the second position, the third instrument processor 415 may be configured to allow maximum flow of energy from the power source to the motor 445, allowing the third surgical instrument 420 to operate at a maximum displacement. When the third instrument processor 415 detects that the switch 450 is in one of the intermediary positions, the third instrument processor 415 may be configured to allow the flow of energy from the power source to the motor 445 at a level corresponding to the position of the switch 450 between the first and second positions allowing the third surgical instrument 420 to operate at an intermediate displacement. For example, if the third instrument processor 415 detects that the switch 450 is positioned half-way (50%) between the first and second positions, the third instrument processor 415 may be configured to allow the flow of energy from the power source to the motor 445 at a level that allows the third surgical instrument 420 to operate at a rate of 50% of the maximum displacement. Alternatively, the third instrument processor 415 may be configured to allow the maximum flow of energy from the power source to the motor 445 whenever the switch 450 is in a position other than the first position, allowing the third surgical instrument 420 to operate at the maximum displacement when the switch 450 is in the second position or any of the intermediary positions.

The third surgical instrument assembly 400 may also comprise a third alert device 455. The third alert device 455 may comprise an audible, a tactile, and/or a visually perceptible device. The third alert device 455 may be configured to be in communication with the third instrument processor 415. The third instrument processor 415 may be configured to send a signal to activate the third alert device 455 to provide a warning or notification based on a pre-programmed condition or setting. For example, as described above, the surgeon may use the user input 130 to enter defined conditions and/or settings into the surgical navigation system 100, such as selecting cortical boundaries, nerves, blood vessels, or similar anatomical structures that the surgeon wishes to avoid and establish regions or zones surrounding those anatomical structures. For example, the surgeon may utilize the user input 130 of the surgical navigation system 100 to define a region or zone within the patient data. This may include identifying a critical anatomical feature such as a nerve or blood vessel and assigning it a zone. It may also comprise identifying additional zones that include regions or areas surrounding the critical anatomical feature, such as defining a second zone encircling the critical anatomical feature that is spaced a distance from the boundary of the critical anatomical feature. It may also include defining additional subsequent zones, such as a third zone encircling the second zone and is spaced a distance from the boundary of the critical anatomical feature that is greater than the distance the second zone is spaced from the critical anatomical feature. In this exemplary configuration, the end-effector 440 is likely to contact the outmost zone first, triggering the alert device 455 to produce a first alert. The end-effector 440 may then contact the next zone closest to the critical anatomical structure, triggering the alert device 455 to produce a second alert. The first and second alerts configured to notify the surgeon of the occurrence of the end-effector 440 entering the respective zones assigned to the first and second alerts.

The surgeon may also use the user input 130 to select and/or input a target location, target trajectory, or similar features of the surgical pathway to help guide the surgeon in performing the medical procedure. The third instrument processor 415, based on data provided by the navigation processor 140, may be configured to send a signal to activate the third alert device 455 upon the end-effector 440 of the third surgical instrument 420 entering one of the regions and/or zones, as defined by the surgeon, that surrounds an anatomical structure. The third instrument processor 415, based on data provided by the navigation processor 140, may also be configured to send a signal to activate the third alert device 455 upon the end-effector 440 of the third surgical instrument 420 being off trajectory and/or upon the end-effector 440 reaching the target location. For example, the third alert device 455 may be activated to produce at least one of an audible, a tactile, or a visually perceptible alert based on the surgical navigation system 100 identifying that the end-effector 440 and/or the third surgical instrument 420 are not properly aligned with the target trajectory established as part of the panned surgical pathway. In this exemplary configuration, the third alert device 455 may produce a tactile alert, such as vibrating the switch 450, to notify the surgeon that the end-effector 440 is not properly aligned with the target trajectory. Once the end-effector 440 is properly aligned with the target trajectory, the third alert device 455 may be deactivated. The third alert device 455 may be similarly configured to be activated to produce at least one of an audible, a tactile, or a visually perceptible alert based on the surgical navigation system 100 identifying that the end-effector 440 and/or the third surgical instrument 420 have reached a target location as defined by the surgeon in the panned surgical pathway. For example, the third alert device 455 may produce a tactile alert, such as vibrating the switch 450, to notify the surgeon that the end-effector 440 has reached the target location, such as preferred depth. Once the end-effector 440 has reached the target location, it is also contemplated that the control console may be configured to deactivate the motor, and by extension the end-effector 340, to prevent the end-effector 340 from going beyond the target location.

In an exemplary configuration, the third alert device 455 may be configured as described above for the first and second alert devices.

The third surgical instrument assembly 400 may also comprise a tracking device 430. The tracking device 430 may be coupled to the handpiece 425 of the third surgical instrument 420. The tracking device 430 may be similar as defined above for the other instrument assemblies.

The surgical instrument assemblies 200, 300, 400 described above are intended to be exemplary instruments and/or configurations within the surgical system 10 but are not intended to be limiting. Other types and forms of surgical instrument assemblies are contemplated. While a plurality of exemplary surgical instrument assemblies 200, 300, 400 are described as being a part of the surgical system 10 and in communication with the surgical navigation system 100, it is contemplated that the surgical system 10 may only comprise a single surgical instrument assembly 200, 300, 400 and a navigation system 100. Furthermore, while the surgical system 10 illustrated in FIGS. 1A-1B includes three surgical instrument assemblies 200, 300, 400 and a single surgical navigation system 100, it is contemplated that the surgical system 10 may be configured to include any combination of surgical instrument assemblies 200, 300, 400, and/or surgical navigation systems 100. For example, the surgical system 10 may include a single surgical instrument assembly 200, 300, 400 and a plurality of surgical navigation systems 100.

Figure 2:
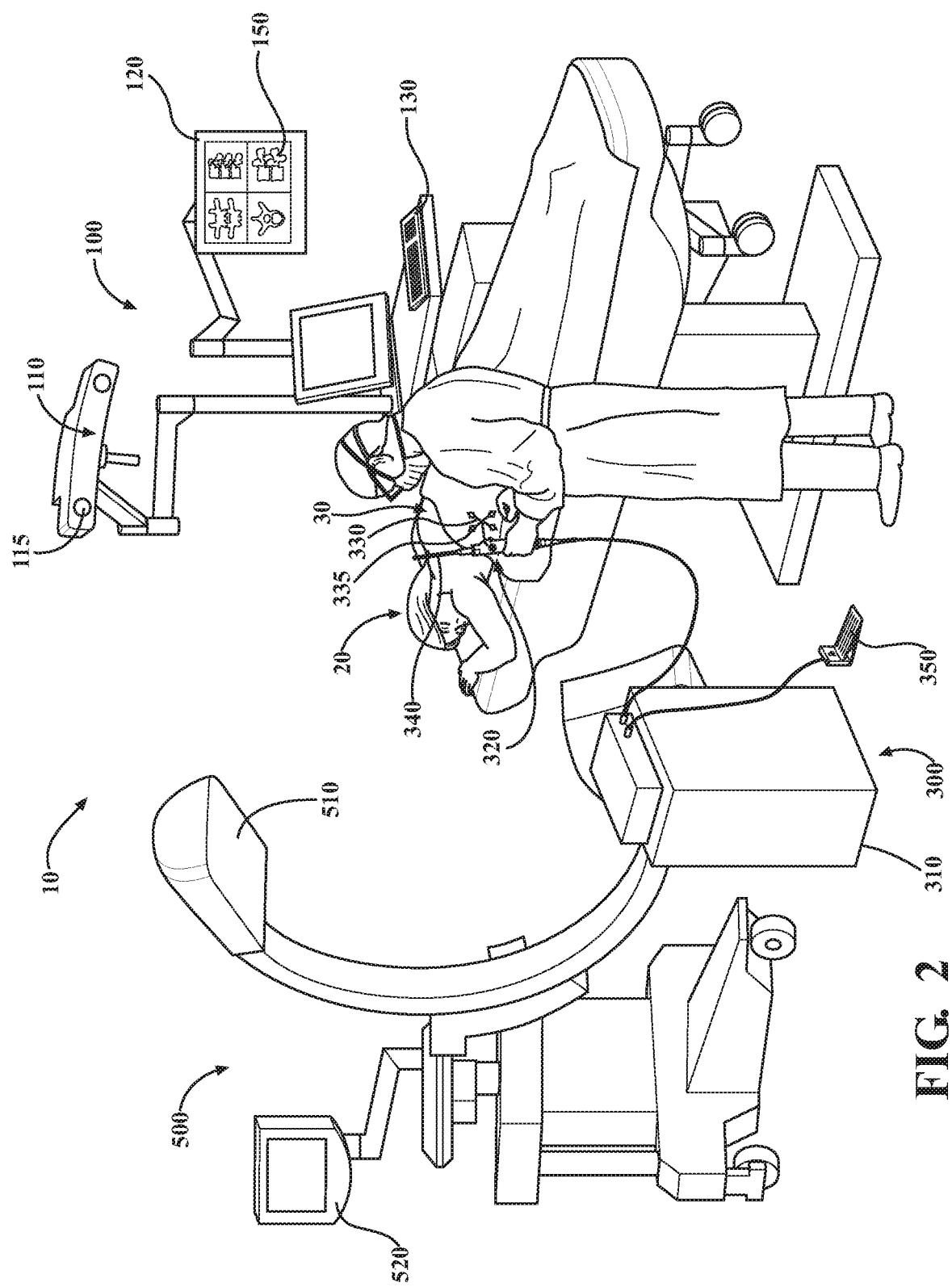
FIG. 2 is a perspective view of an exemplary layout of an operating room including at least one of the surgical instrument assemblies and the surgical navigation system of FIGS. 1A-1B for performing a medical procedure on a patient.

Referring to FIG. 2, an exemplary configuration of an operating room or surgical suite for performing a medical procedure on a patient 20 using the surgical system 10 described above is shown. The surgical system 10 including the surgical navigation system 100 and at least one of the surgical instrument assemblies 200, 300, 400 described above may be placed in the operating room surrounding the patient 20 and/or the surgical site 30 where the medical procedure is to be performed.

While only the second surgical instrument assembly 300 is illustrated in FIG. 2, it should be understood that it is only an exemplary configuration of the surgical system 10, and that it is contemplated that any number of surgical instrument assemblies 200, 300, 400 may be positioned within the operating room. As described above, the second surgical instrument assembly 300 comprises the second surgical instrument 320 including the end-effector 340 and the tracking device 330. The tracking device 330 includes a plurality of markers 335 that are capable of being identified and/or tracked by the surgical navigation system 100. The second surgical instrument 320 is coupled to the console 310 that is positioned away from the second surgical instrument 320. The second surgical instrument assembly 300 also comprises the switch 350 that is positioned away from the patient 20 and that is coupled to the console 310. The switch 350 is in communication with second surgical instrument 320 via the second instrument processor 315 (not shown) housed within the console 310.

While not illustrated in FIG. 2, the second surgical instrument assembly 300 also comprises the second alert device 355 described above. The second alert device 355 may be positioned on the switch 350, somewhere on the surgeon's person, and/or a location within the operating room that is observable by the surgeon based on the configuration of the second alert device 355. For example, as described above, the second alert device 355 including a tactile member may be positioned on the surgeon, such as on their wrist or ankle. Alternatively, a second alert device 355 including an audible member may be positioned on the surgeon's ear. In yet another configuration, a second alert device 355 including a visual device, the second alert device 355 may be positioned on the display unit 120 of the surgical navigation system 100 or in a similar location that is capable of being perceived by the surgeon without blocking or interfering with the surgeons view of the surgical site 30. In other configurations, the second alert device is a footswitch, and is not readily observable during the surgery because of its position underneath an operating room table.

While not previously discussed, it is also contemplated that the surgical system 10 may further comprise an imaging system 500, such as CT or MRI imaging device. The imaging system 500 may comprise a scanner 510 and a display unit 520. The scanner 520 may be utilized to take an image of the surgical site 30 on the patient 20 and display it on the display unit 520. For example, the scanner may comprise a C-arm configured to be rotated about the patient 20 to produce a plurality of images of the surgical site 30. The imaging system 500 may also comprise a processor (not shown) including software, as is known by those skilled in the art, which is capable of taking the plurality of images captured by the scanner 510 and producing a 2-D image and/or a 3-D model of the surgical site 30. The display unit 520 may be configured to display the resulting 2-D image and/or 3-D model.

The imaging system 500 may also be in communication with the navigation processor 140 of the surgical navigation system 100. The imaging system 500 may be configured to communicate via a wired and/or a wireless connection with the navigation processor 140. For example, the imaging system 500 may be configured to provide pre-operative and/or intra-operative image data, such as the resulting 2-D image and/or 3-D model of the surgical site 30, to the navigation processor 140. The navigation processor 140 may then be configured to provide the resulting 2-D image and/or 3-D model to the navigation display unit 120, where the surgeon, using the user input 130 or using algorithms, may identify and/or define the corresponding regions and/or zones around critical anatomical structures. For example, the surgeon may utilize the user input 130 of the surgical navigation system 100 to define an alert zone around a vertebral body, a nerve or a blood vessel that the surgeon wishes to avoid during execution of the medical procedure. The surgeon may utilize the user input 130 of the surgical navigation system 100 to input and/or modify the planned surgical pathway, boundaries, or alert zones to be utilized in executing the medical procedure.

Figure 3:
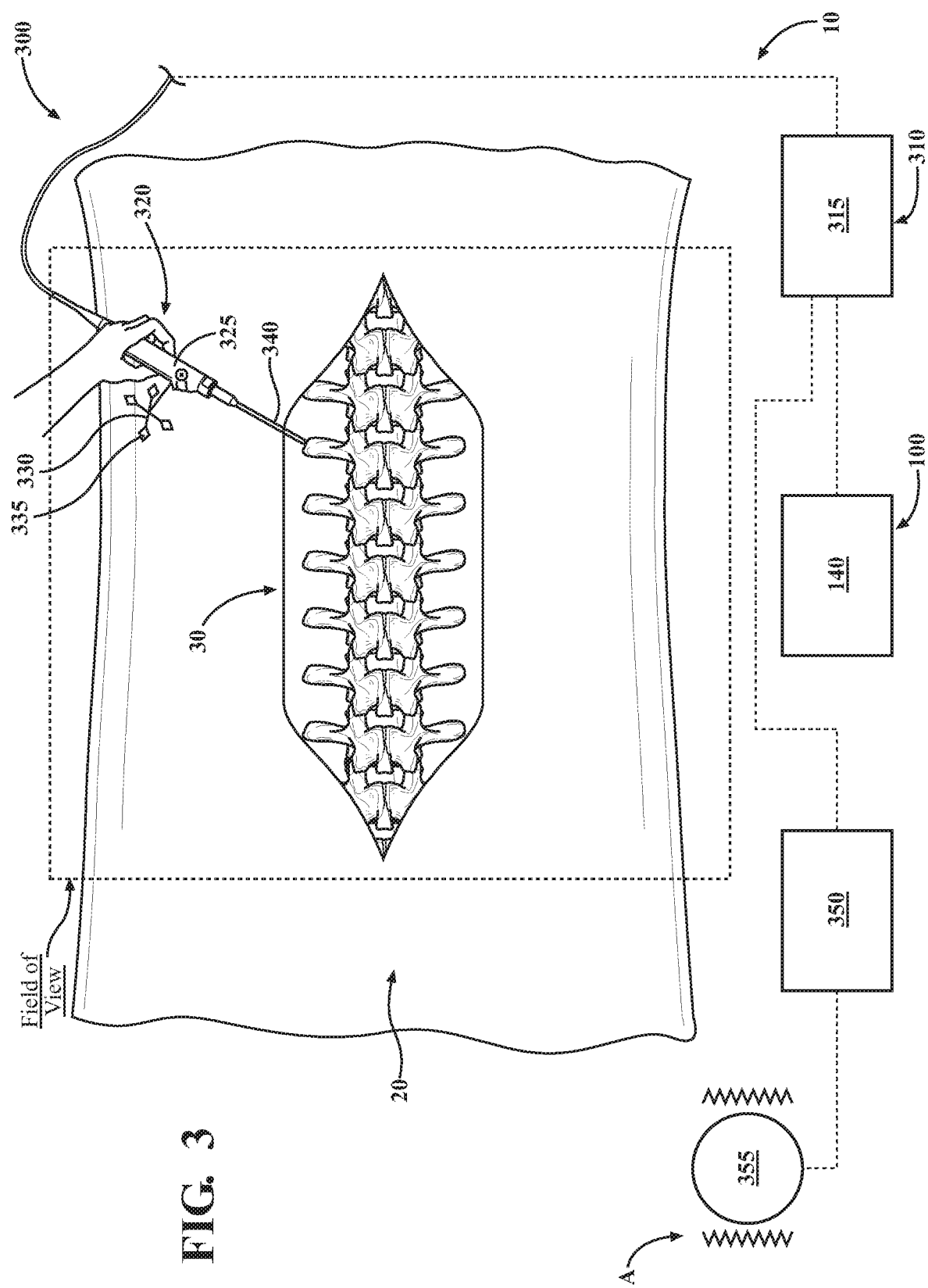
FIG. 3 is a schematic view of a surgical site as viewed from the surgeon's perspective while using at least one of the surgical instrument assemblies of FIGS. 1A-1B to execute a medical procedure on a patient.

Referring to FIG. 3, an exemplary schematic view of the surgical site 30 on the patient 20 during the execution of a medical procedure as viewed from the surgeon's perspective is illustrated. The exemplary schematic of FIG. 3 depicts an exemplary arrangement of the surgical system 10 described above during a medical procedure, including the second surgical instrument assembly 300. The second surgical instrument assembly 300 comprises the second surgical instrument 320, including the handpiece 325 and end-effector 340, positioned proximate the surgical site 30 and within the surgeon's field of view. Additional components of the second surgical instrument assembly 300 are in communication with the second surgical instrument 320 but are positioned away from the second surgical instrument 320 and outside the surgeon's field of view. For example, the surgical navigation system 100, the console 310, the switch 350, and the alert device 355 may all be positioned away from the second surgical instrument 320 and outside the surgeon's field of view when the surgeon is focused on the surgical site. This may reduce the obstructions to the surgeons view of the surgical site and improve the surgeons' ability to focus on the surgical site 30 and/or execute the medical procedure.

Referring to FIGS. 4A-5C, various schematic views of the surgical system 10 described above during execution of a medical procedure are illustrated. The various schematic views of the surgical system 10 include one or more of the surgical instruments 220, 320, 420 described above in various orientations relative to the patient 20 for the purpose of further explaining the operation of the surgical system 10. The surgical instrument 220, 320, 420, such as the second surgical instrument 320, is illustrated in a first position relative to the surgical site 30 on the patient 20. The surgical instrument 220, 320, 420 may comprise the console or housing 210, 310, 410 including the instrument processor 215, 315, 415. As described above, the instrument processor 215, 315, 415 may be in communication with the navigation processor 140 of the navigation system. The surgical instrument 220, 320, 420 may also comprise the switch 250, 350, 450, such as a trigger, hand-switch, or footswitch, that is coupled to the console or housing 210, 310, 410 and in communication with the instrument processor 215, 315, 415. The alert device 255, 355, 455 may be coupled to the switch 250, 350, 450 and in communication with the instrument processor 215, 315, 415. While not shown in the figures, as described above, the alert device 255, 355, 455 is not required to be coupled to the switch 250, 350, 450. By contrast, it is contemplated that the alert device 255, 355, 455 may be separate from the switch 250, 350, 450. For example, the alert device 255, 355, 455 may be coupled to the console or housing 210, 310, 410 and either in wired or wireless communication with the instrument processor 215, 315, 415. It is also contemplated that the alert device 255, 355, 455 is a standalone device, such as a bracelet or armband to be worn by the surgeon, which is in wireless communication with the instrument processor 215, 315, 415.

Figure 4A:
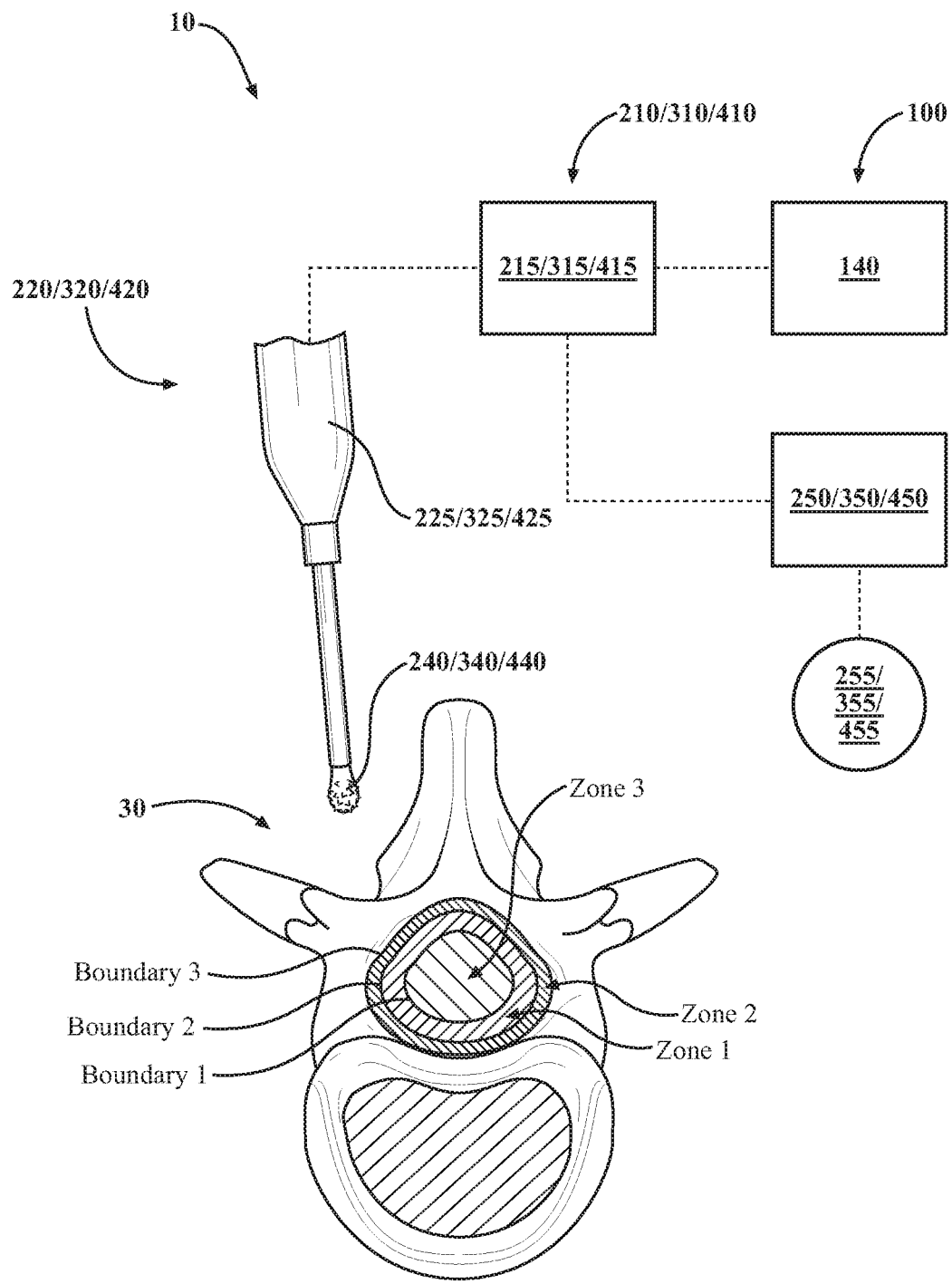
FIG. 4A is a schematic view of a first exemplary surgical instrument of the surgical system of FIGS. 1A-1B, the first surgical instrument oriented in a first position relative to the patient.
Figure 4B:
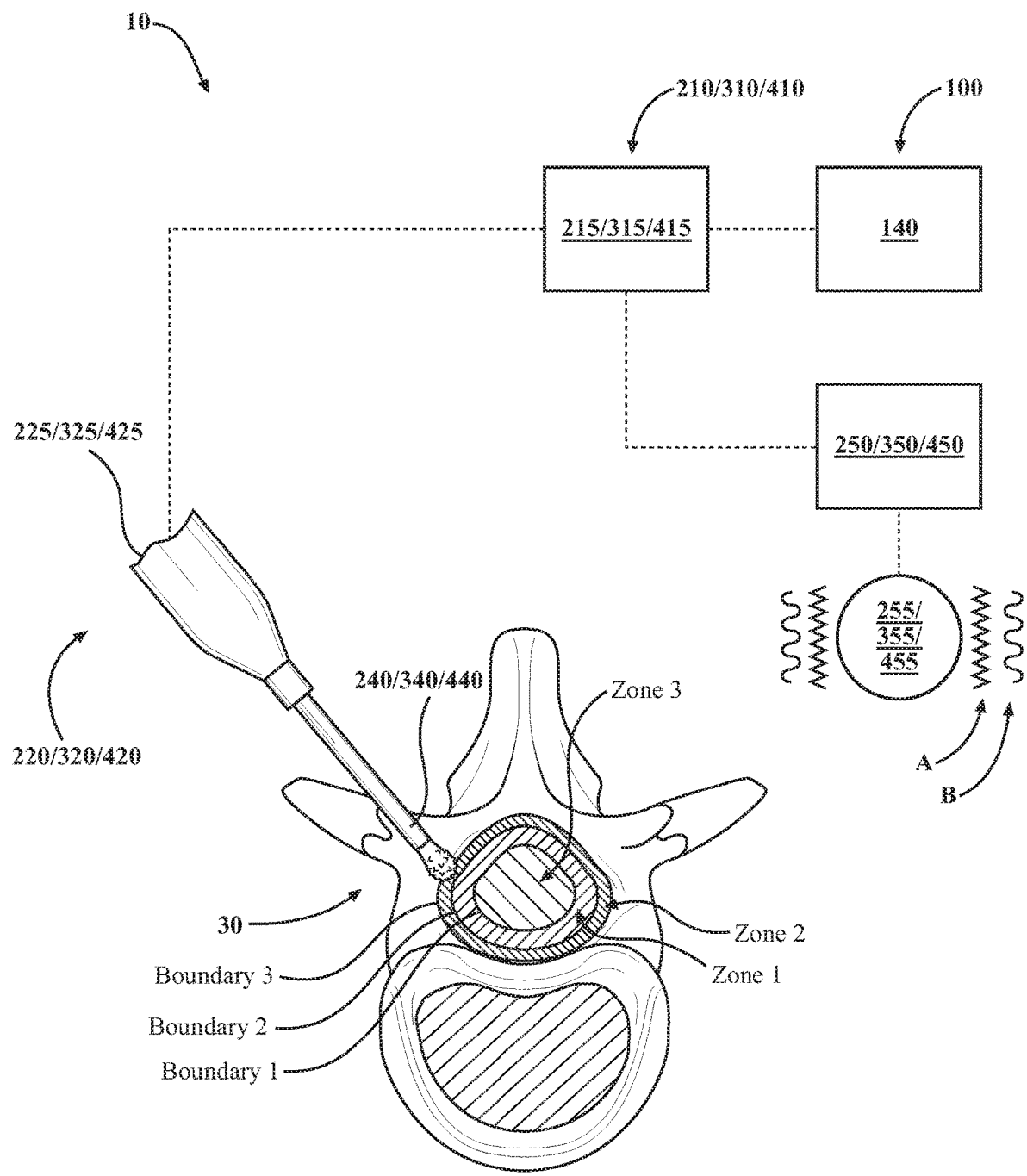
FIG. 4B is a schematic view of the first surgical instrument of FIG. 4A, the first surgical instrument oriented in a second position relative to the patient.
Figure 4C:
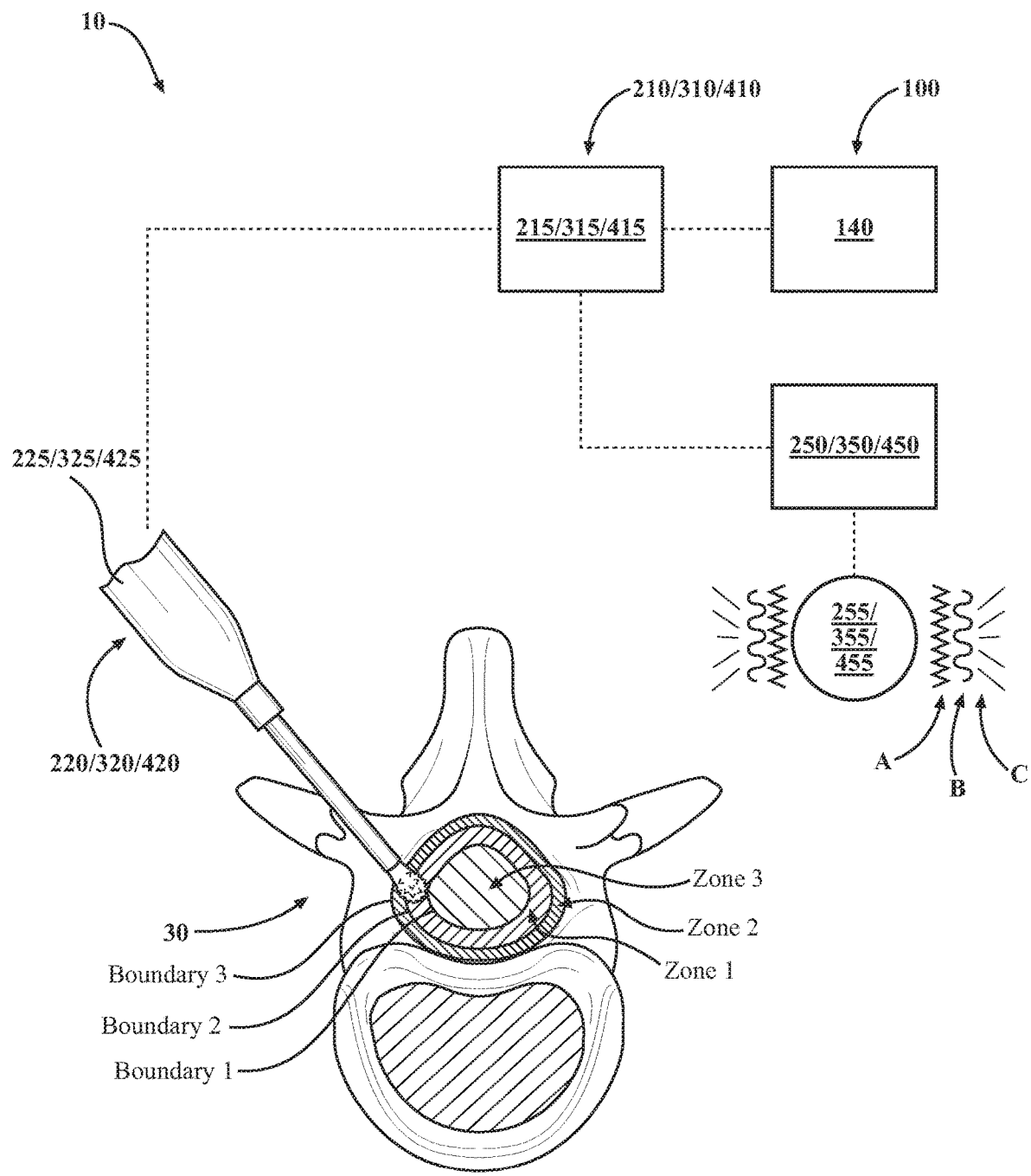
FIG. 4C is a schematic view of the first surgical instrument of FIG. 4A, the first surgical instrument oriented in a third position relative to the patient.

Furthermore, as described above, the surgeon, using the surgical navigation system 100, may identify and/or define various boundaries, regions, target trajectories, target locations, or the like in the pre-operative and/or intra-operative patient data, such as a CT or MM scan. For example, as illustrated in FIGS. 4A-4C, the surgeon may utilize the surgical navigation system 100 to select and/or define a virtual boundary (Boundary 1, 2, 3) and/or an alert zone (Zones 1, 2, 3) relative to a critical anatomical structure or boundary, such as the central foramen, a wall of a vertebral body, a nerve or blood vessel, within the surgical site 30. This may include defining a plurality of virtual boundaries (Boundary 1, 2, 3) and/or alert zones (Zones 1, 2, 3) at varying distances from the critical anatomical structure. For example, as illustrated in FIGS. 4A-5C, the surgical site 30 includes a vertebra, on which a medical procedure is to be performed. A first virtual boundary, Boundary 1, may be defined relative to the critical anatomical structure, such as an outer perimeter of the spinal cord. Boundary 1 may be defined manually by the surgeon using the navigation system 100. However, Boundary 1 may also be selected by the surgeon from a populated list of virtual boundaries provided by the boundary generator software of the navigation system 100. As described above, the navigation system 100 may comprise software including a boundary generator. The navigation processor 140 may be configured to provide a listing of one or more virtual boundaries based on various data points selected or input by the surgeon. For example, the surgeon may select the location of the surgery, the type of surgery, the type of surgical instrument 200, 300, 400 to be used, the type of device or implant to be inserted or the like, and the boundary generator may be configured to define one or more virtual boundaries for selection by a user. The boundary generator may also be configured to define the alert zone (Zones 1, 2, 3, 4). A first alert zone, Zone 1, may be defined a first distance from a critical anatomical structure, such as an outer boundary of the spinal cord. Zone 1 may be defined as a volume between the first virtual boundary, Boundary 1, and a second virtual boundary, Boundary 2. Boundary 2 may be defined by the surgeon, including the surgeon inputting and/or selecting a desired depth of Zone 1, and the navigation system being configured to define Boundary 2 based on the depth. For example, the navigation system 100 may be configured to prompt the surgeon to enter and/or select a depth, and then the navigation system may define Boundary 2 based on the depth. Alternatively, Boundary 2 may be selected by the surgeon from a populated list of virtual boundaries provided by the boundary generator software of the navigation system 100. For example, the navigation system 100 may be configured to provide a populated list of end-effectors 240, 340, 440, including a default depth of the alert zone for each of the end-effectors 240, 340, 440, and the navigation system may be configured to define Zone 1 based on the end-effector 240, 340, 440 selected by the surgeon.

In one exemplary configuration, the boundary generator may be configured to generate the second virtual boundary, Boundary 2, at a default distance from the first virtual boundary, Boundary 1, based, at least in part, on the surgical procedure being performed. For example, the boundary generator may be configured to generate Boundary 2 to be two millimeters from Boundary 1. The surgeon may edit or modify the distance or depth between Boundary 1 and Boundary 2 using the graphical user interface (GUI) 150 and or the user input 130. The volume defined between Boundary 1 and Boundary 2 may define the first alert zone, Zone 1.

A second alert zone, Zone 2, may be defined a second distance from the critical anatomical structure, such that the second distance is greater than the first distance. Zone 2 may be defined as a volume between by Boundary 2 and a third virtual boundary, Boundary 3. Boundary 3 may be defined by the surgeon, or Boundary 3 may be selected by the surgeon from a populated list of virtual boundaries provided by the boundary generator software of the navigation system 100. For example, the boundary generator may be configured to generate Boundary 3 a default distance from Boundary 2 based, at least in part, on the surgical procedure being performed. The surgeon may edit or modify the distance or depth between Boundary 2 and Boundary 3 using the graphical user interface (GUI) 150 and or the user input 130. A third alert zone, Zone 3, may be defined at the boundary of and/or including the critical anatomical structure. A fourth virtual boundary, Boundary 4, may also be defined at a perimeter and/or boundary of the biological tissue, such as the vertebra. It is also contemplated that the surgical navigation system 100 may be configured to define the virtual boundaries (Boundary 1, 2, 3, 4) and/or alert zone(s) (Zones 1, 2, 3, 4) based on information selected or input by the medical professional. For example, the surgical navigation system 100 may be configured to define the alert zone (Zones 1, 2, 3, 4) based on one or more of the following items input by the medical professional: the type procedure to be performed, the location of the procedure on the patient, the type of implant 275 to be used, the type of surgical instrument 220, 320, 420 to be used and/or the type end-effector 240, 340, 440. The medical professional may then have the opportunity to modify or alter the virtual boundaries (Boundary 1, 2, 3, 4) and/or alert zone(s) (Zones 1, 2, 3, 4) defined by the surgical navigation system 100 using the user input device 130 and/or the graphical user interface (GUI) 150. Again, it is also contemplated that the various zones are automatically generated based on an algorithm recognizing certain critical anatomical structures in the image data.

During a medical procedure to remove biological tissue from the surface of the vertebra at the surgical site, the end-effector 240, 340, 440 of the surgical instrument 220, 320, 420 may approach one of the various virtual boundaries (Boundary 1, 2, 3, 4) and/or alert zones (Zones 1, 2, 3, 4). As described above, the surgical navigation system 100 may be configured to track the position and/or orientation of the surgical instrument 220, 320, 420 relative to the various virtual boundaries (Boundary 1, 2, 3, 4) and/or alert zones (Zones 1, 2, 3, 4) and communicate a signal or instruction to the instrument processor 215, 315, 415 to activate the alert device 255, 355, 455 to notify the surgeon when the end-effector 240, 340, 440 approaches and/or enters one of the various virtual boundaries (Boundary 1, 2, 3, 4) and/or alert zones (Zones 1, 2, 3, 4). For example, in the case of the virtual boundaries (Boundary 1, 2, 3, 4), the surgical navigation system 100 may be configured to track the position and/or location of the surgical instrument 220, 320, 420 relative to the various virtual boundaries (Boundary 1, 2, 3, 4) and communicate a signal or instruction to the instrument processor 215, 315, 415 to activate the alert device 255, 355, 455 to notify the surgeon when the end-effector 240, 340, 440 is adjacent and/or distal to the virtual boundary (Boundary 1, 2, 3, 4). For example, the instrument processor 215, 315, 415 to activate the alert device 255, 355, 455 based upon the tip of the end-effector being positioned adjacent the virtual boundary (Boundary 1, 2, 3, 4). The instrument processor 215, 315, 415 to activate the alert device 255, 355, 455 based upon the tip of the end-effector being positioned a defined distance distal of the virtual boundary (Boundary 1, 2, 3, 4). The instrument processor 215, 315, 415 may be configured to define the distance as the tip being positioned 0.5 mm, 1 mm, 2 mm, 3 mm, etc. distal of the virtual boundary (Boundary 1, 2, 3, 4). The surgical navigation system 100 may be configured to allow the surgeon to assign a particular type of alert to each of the various virtual boundaries (Boundary 1, 2, 3, 4) and/or alert zones (Zones 1, 2, 3, 4). This may include an audible, a tactile, and/or a visual alert to notify the surgeon. The audible, tactile, and/or visual alert may be coupled to the switch 250, 350, 450, such as a footswitch or trigger that the surgeon will be in contact with when operating the surgical instrument. As described above, there are various advantages to position an alert device 255, 355, 455 including a tactile alert on the switch 250, 350, 450. This may be particularly true when the alert device 355, 455 including a tactile alert is position on a switch 350, 450 that is positioned away from the surgical instrument 320, 420, such as was the case in the exemplary second and third surgical instrument assemblies 300, 400 described above.

Once the alert device 255, 355, 455 has been activated, the system 10 may be configured such that the alert device 255, 355, 455 may be deactivated by the surgeon. This may be accomplished by pressing a button or switch or icon configured to deactivate alert device 255, 355, 455. The buttons, switches, and/or icons for deactivating the alert device(s) 255, 355, 455 may be positioned on the navigation system 140. For example, the navigation display 120 may be configured as a touchscreen that allows the user to select an icon to deactivate the alert device(s) 255, 355, 455. It is further contemplated that the surgeon may manipulate a button or switch on the user input 130 of the navigation system 100 to deactivate the alert device(s) 255, 355, 455. It is also contemplated that the buttons or switches for deactivating the alert device(s) 255, 355, 455 may be positioned on the housing 210 or console 310, 410 of the surgical instrument assembly 200, 300, 400, and the surgeon may manipulate the button or switch to deactivate the alert device(s) 255, 355, 455. Alternatively, it is also contemplated that this may be accomplished by manipulating the trigger and/or foot switch 250, 350, 450 in a defined pattern or cadence to deactivate the alert device 255, 355, 455. For example, the system may be configured such that double tapping the switch 250, 350, 450 after the alert device 255, 355, 455 has been activated will deactivate the alert device 255, 355, 455 to allow the surgeon to continue the procedure uninterrupted. The system 10 may be configured such that deactivating the alert device 255, 355, 455 may require an action by the surgeon, such as double tapping the switch 250, 350, 450. This ensures that the surgeon acknowledges and/or confirms having received the alert and has taken an affirmative and unambiguous step to deactivate the alert device 255, 355, 455. This may prevent accidental deactivation of the alert device 255, 355, 455 without the surgeon receiving and/or being aware the alert device 255, 355, 455 was activated.

The surgical navigation system 100 may also be configured to provide an alert by manipulating the speed of the motor 245, 345, 445, and by extension the speed at which the end-effector 240, 340, 440 is operated based on the position and/orientation of the surgical instrument 220, 320, 420 relative to the one or more of the virtual boundaries (Boundary 1, 2, 3, 4) and/or alert zones (Zones 1, 2, 3, 4). For example, the surgical navigation system 100 may be configured to decelerate the motor 245, 345, 445 from a maximum cutting speed to a minimum cutting speed based on the position of the surgical instrument 220, 320, 420 relative to the one or more virtual boundaries (Boundary 1, 2, 3, 4) and/or alert zones (Zones 1, 2, 3, 4).

This may include the surgical navigation system 100 sending a signal to the second instrument processor 315 to reduce the output of the motor 345 of the second surgical instrument 320, such as a high speed cutting bur, to reduce the rotation of the end-effector 340 from a current operating speed, such as 75,000 RPMs to a lower speed that is still effective to cut tissue, such as 60,000 RPMs, once the end-effector 340 is adjacent and or distal to the second virtual boundary, Boundary 2, and/or enters the first alert zone, Zone 1. Manipulation of the speed of the motor 245, 345, 445 of the surgical instrument 220, 320, 420, and by extension the rotation of the end-effector 240, 340, 440, may be caused by the instrument processor 215, 315, 415 being configured to regulate the current and/or voltage supplied to the motor 245, 345, 445. For example, to decelerate the motor 245, 345, 445 of the surgical instrument 220, 320, 420, the instrument processor 215, 315, 415 may be configure to reduce the voltage and/or current supplied to the motor 245, 345, 445. The instrument processor 215, 315, 415 may be configured to gradually reduce current and/or voltage supplied to the motor 245, 345, 445 resulting in a gradual reduction of the rotation of the end-effector 240, 340, 440. This gradual reduction of the current and/or voltage allows the motor 245, 345, 445 to drift from the first cutting speed to second cutting speed. The reverse may also be true. The instrument processor 215, 315, 415 may similarly be configured to accelerate the motor 245, 345, 445 of the surgical instrument 220, 320, 420 by increasing the voltage and/or current supplied to the motor 245, 345, 445.

Decelerating the motor 245, 345, 445 of the surgical instrument 220, 320, 420 may provide an alert or notification to the surgeon in the form of a tactile alert felt by the surgeon in the handpiece 225, 325, 425. It is also contemplated that decelerating the motor 245, 345, 445 of the surgical instrument 220, 320, 420 may provide an alert or notification to the surgeon in the form an audible alert as the surgeon hears a change in the pitch of the motor 245, 345, 445 as the motor 245, 345, 445 is decelerated from the maximum cutting speed to the minimum cutting speed, or perceives a change in cutting efficacy. While it is not required that the motor 245, 345, 445 is decelerated from the maximum cutting speed to the minimum cutting speed, it is desirable that the motor 245, 345, 445 not decelerate below a predetermined minimum cutting speed to prevent the end-effector 240, 340, 440 from biting or grabbing and being thrown offline and/or off-trajectory. This could result in the end-effector 240, 340, 440 contacting and/or damaging a critical anatomical structure. It is further contemplated that the surgical navigation system 100 may also be configured to disable or stop the motor 245, 345, 445 if the end-effector 240, 340, 440 approaches the critical anatomical structure. This may prevent the end-effector 240, 340, 440 from contacting and/or damaging the critical anatomical structure. During the course of tracking surgical instrument 220, 320, 420 and by extension the end-effector 240, 340, 440, it is contemplated that the tracking device of the surgical instrument 220, 320, 420 may be blocked from view of the navigation system. It is further contemplated that the navigation system 100 may be configured to disable or stop the motor 245, 345, 445 to prevent operation of the end-effector 240, 340, 440 if the tracking device of the surgical instrument 220, 320, 420 is out of view of the navigation system 100 for a defined period of time in order to prevent operation of the surgical instrument 220, 320, 420 when its position is unknown within the patient space. An exemplary navigation system and/or method of configured to prevent operation of a surgical instrument when outside the view of the navigation system is described in in U.S. Patent Publ. No. 2016/0242858A1, which is hereby incorporated in by reference in its entirety.

Referring to FIG. 4A, the surgical instrument 220, 320, 420, such as the second surgical instrument 320, 420, is illustrated in a first position and/or orientation relative to the surgical site 30 on the patient. The surgical instrument 220, 320, 420 may be configured to remove biological tissue from the surgical site 30. In the first position, the end-effector 240, 340, 440 is spaced from the defined virtual boundaries (Boundary 1, 2, 3) and/or outside the volumes defining the alert zones (Zones 1, 2, 3). In this exemplary scenario, the surgical navigation system 100 may identify that the end-effector 240, 340, 440 is spaced from the defined virtual boundaries (Boundary 1, 2, 3) and/or outside the defined alert zones (Zones 1, 2), and allow the surgical instrument 220, 320, 420 to operate under normal working conditions when the switch 250, 350, 450 is manipulated to actuate the end-effector 240, 340, 440. The alert device 255, 355, 455 may be configured to be inactive in this scenario. The nested nature of boundaries 1, 2, and 3 and zones 1, 2, and 3 (one being more distal than the other) may provide progressively more alerts to ensure that the surgeon is aware that the surgical instrument 220, 320, 420 is in close proximity to the critical anatomical structure and/or target depth.

Referring to FIG. 4B, the surgical instrument 220, 320, 420 is illustrated in a second position relative to the surgical site 30 on the patient. In the second position, the end-effector 240, 340, 440, while removing biological tissue, has at least partially entered the second alert zone, Zone 2. In this example, Zone 2 is defined between Boundary 3 and Boundary 2. In this exemplary scenario, the surgical navigation system 100 may identify that the end-effector 240, 340, 440 is positioned adjacent and/or distal to Boundary 3 and/or has entered the volume representing the second alert zone, Zone 2, and trigger one of the various alerts described above. For example, the surgical navigation system 100 may be configured to send a signal to the instrument processor 215, 315, 415 and/or navigation processor to activate the alert device 255, 355, 455 because the end-effector 240, 340, 440 is positioned adjacent and/or distal to Boundary 3 and/or has entered the second alert zone, Zone 2. The alert device 255, 355, 455, depending on the type of alert assigned to the second alert zone, Zone 2, may be configured to provide a tactile alert A, such as vibrating the switch 250, 350, 450. Alternatively, the alert device 255, 355, 455 may be configured to provide a visual alert B, such as a blinking light on the display screen of the navigation system. In yet another configuration, the alert device 255, 355, 455 may be configured to provide an audible alert C, such as a beeping noise. The surgical navigation system 100 may also be configured to send a signal to the instrument processor 215, 315, 415 to reduce the output of the motor 245, 345, 445 of the surgical instrument 220, 320, 420 to reduce the rotation of the end-effector 240, e.g., a surgical bur, 340, 440 from a first cutting speed of greater than 70,000 rotations per minute (70,000 RPMs) to a second cutting speed of below 70,000 rotations per minute and above 60,000 rotations per minute (60,000 RPMs). It is also contemplated that a combination of the various alerts may be utilized, such as the alert device 255, 355, 455 producing a combination of a tactile alert A and a visual alert B, as is illustrated in FIG. 4B.

Referring to FIG. 4C, the second surgical instrument 220, 320, 420 is illustrated in a third position relative to the surgical site 30 on the patient. In the third position, the end-effector 240, 340, 440, while removing biological tissue, is distal to Boundary 2 and/or has entered the first alert zone, Zone 1, defined between Boundary 1 and Boundary 2.

In this exemplary scenario, the surgical navigation system 100 may determine that the end-effector 240, 340, 440 entered the first alert zone, Zone 1, and trigger one of the various alerts described above. For example, the surgical navigation system 100 may be configured to send a signal to the instrument processor 215, 315, 415 indicating the position of the end-effector 240, 340, 440 relative to the Boundary 2 and/or Zone 1. The signal from the surgical navigation system 100 may include a command causing the instrument processor 215, 315, 415 to activate the alert device 255, 355, 455 if the end-effector 240, 340, 440 is positioned adjacent and/or distal to Boundary 2 and/or has entered the first alert zone, Zone 1. Alternatively, is also contemplated that that the signal from the surgical navigation system 100 may include the position of the position of the end-effector 240, 340, 440 relative to the Boundary 2 and/or Zone 1, and the instrument processor 215, 315, 415 may be configured to activate the alert device 255, 355, 455 upon the surgical navigation system 100 indicating the end-effector 240, 340, 440 is positioned adjacent and/or distal to Boundary 2 and/or has entered the first alert zone, Zone 1. The alert device 255, 355, 455, depending on the type of alert assigned to the first alert zone, Zone 1, may be configured to provide a tactile alert A, such as vibrating the switch 250, 350, 450. Alternatively, the alert device 255, 355, 455 may be configured to provide a visual alert B, such as a blinking light. In yet another configuration, the alert device 255, 355, 455 may be configured to provide an audible alert C, such as a beeping noise. The surgical navigation system 100 may also be configured to send a signal to the instrument processor 215, 315, 415 to reduce the output of the motor 245, 345, 445 of the surgical instrument 220, 320, 420 to reduce the rotation of the end-effector 240, 340, 440 from 75,000 RPMs to 60,000 RPMs. Alternatively, the surgical navigation system 100 may be configured to disable or stop the rotation of the end-effector 240, 340, 440 once it enters the first alert zone, Zone 1, to prevent the end-effector 240, 340, 440 from being active in the critical anatomical structure. This may prevent the end-effector 240, 340, 440 from damaging the critical anatomical structure. It is also contemplated that a combination of the various alerts may be utilized, such as the alert device 255, 355, 455 producing a combination of a tactile alert A, a visual alert B, and an audible alert C, as is illustrated in FIG. 4C.

Figure 4D:
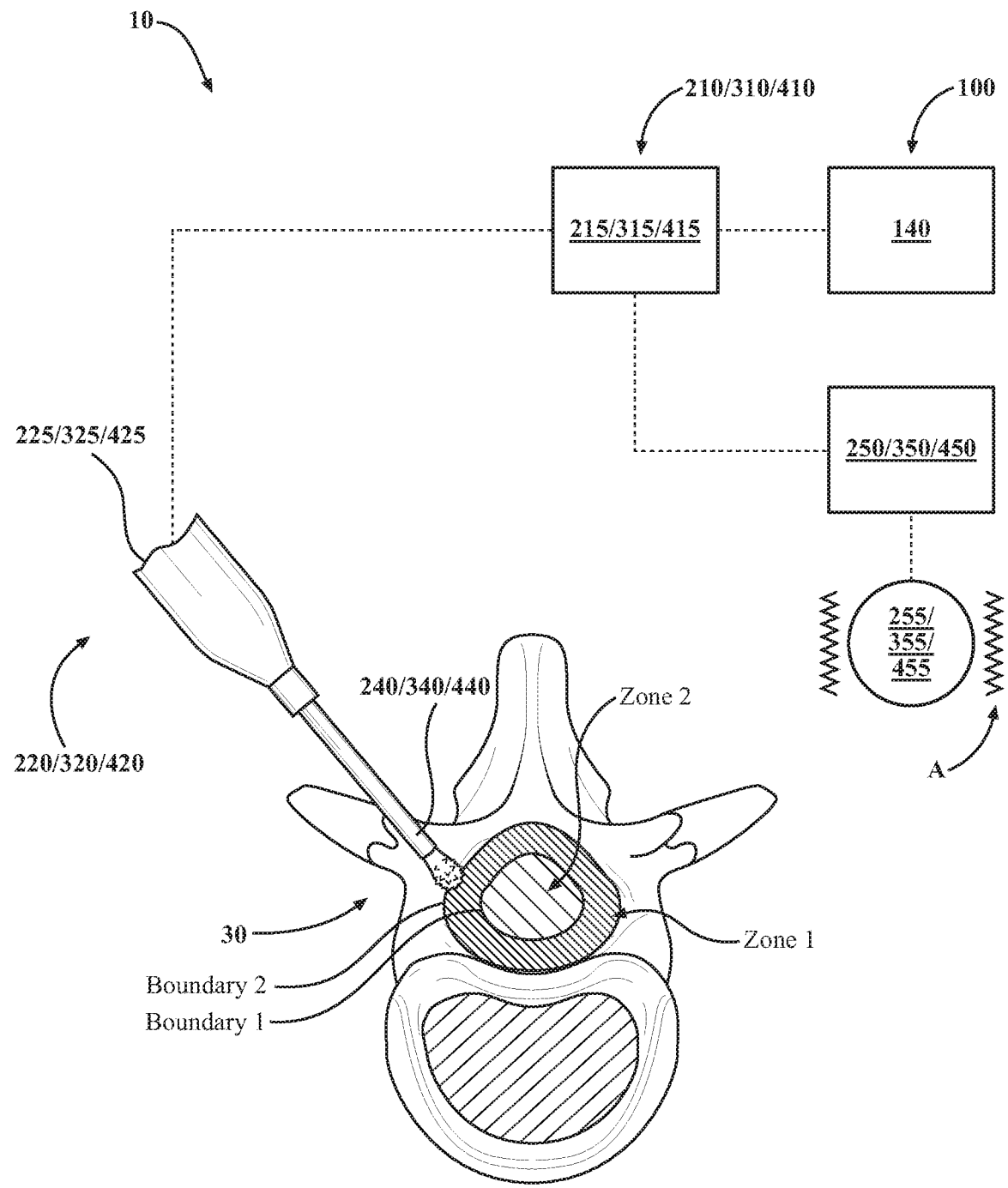
FIG. 4D is a schematic view of the first surgical instrument of FIG. 4A, the first surgical instrument oriented in a fourth position relative to the patient.

Referring to FIG. 4D, the second surgical instrument 220, 320, 420 is illustrated in a fourth position relative to the surgical site 30 on the patient. As illustrated in FIG. 4D, the surgical navigation system and/or the medical professional have only selected and/or defined two alert zones including a first alert zone, Zone 1 and second alert zone, Zone 2. Zone 2 represents the critical anatomical structure, such as the central foramen. Zone 1 is defined between Boundary 1 and Boundary 2, wherein Boundary 1 is a recognized perimeter of the critical anatomical structure, a boundary of the central foramen. As described above, this boundary can be recognized through uses of a segmentation algorithm. In the fourth position, the end-effector 240, 340, 440, while removing biological tissue, is positioned adjacent and/or distal to Boundary 2 and/or has entered the first alert zone, Zone 1. In this exemplary scenario, the surgical navigation system 100 may identify that the end-effector 240, 340, 440 is positioned adjacent and/or distal to Boundary 2 and/or has entered the first alert zone, Zone 1, and trigger one of the various alerts described above. For example, the surgical navigation system 100 may be configured to send a signal to the instrument processor 215, 315, 415 indicating the position of the end-effector 240, 340, 440 relative to the Boundary 2 and/or Zone 1. The signal from the surgical navigation system 100 may include a command causing the instrument processor 215, 315, 415 to activate the alert device 255, 355, 455 if the end-effector 240, 340, 440 is positioned adjacent and/or distal to Boundary 2 and/or has entered the first alert zone, Zone 1. Alternatively, is also contemplated that that the signal from the surgical navigation system 100 may include the position of the position of the end-effector 240, 340, 440 relative to the Boundary 2 and/or Zone 1, and the instrument processor 215, 315, 415 may be configured to activate the alert device 255, 355, 455 upon the surgical navigation system 100 indicating the end-effector 240, 340, 440 is positioned adjacent and/or distal to Boundary 2 and/or has entered the first alert zone, Zone 1. The alert device 255, 355, 455, depending on the type of alert assigned to each of Boundary 2 and the first alert zone, Zone 1, may be configured to provide a tactile alert A, such as vibrating the switch 250, 350, 450. Alternatively, the alert device 255, 355, 455 may be configured to provide a visual alert B, such as a blinking light. In yet another configuration, the alert device 255, 355, 455 may be configured to provide an audible alert C, such as a beeping noise. The surgical navigation system 100 may also be configured to send a signal to the instrument processor 215, 315, 415 to reduce the output of the motor 245, 345, 445 of the surgical instrument 220, 320, 420 to reduce the rotation of the end-effector 240, 340, 440 from a first cutting speed of greater than 70,000 rotations per minute (70,000 RPMs) to a second cutting speed of below 70,000 rotations per minute and above 60,000 rotations per minute (60,000 RPMs). Alternatively, the surgical navigation system 100 may be configured to disable or stop the rotation of the end-effector 240, 340, 440 once it is positioned adjacent and/or distal to Boundary 2 and/or has enters the first alert zone, Zone 1, to prevent the end-effector 240, 340, 440 from contacting and/or entering the second alert zone, Zone 2, defined around the critical anatomical structure. This may prevent the end-effector 240, 340, 440 from contacting and/or damaging the critical anatomical structure. It is also contemplated that a combination of the various alerts may be utilized, such as the alert device 255, 355, 455 producing a combination of a tactile alert A, a visual alert B, and an audible alert C.

Figure 5A:
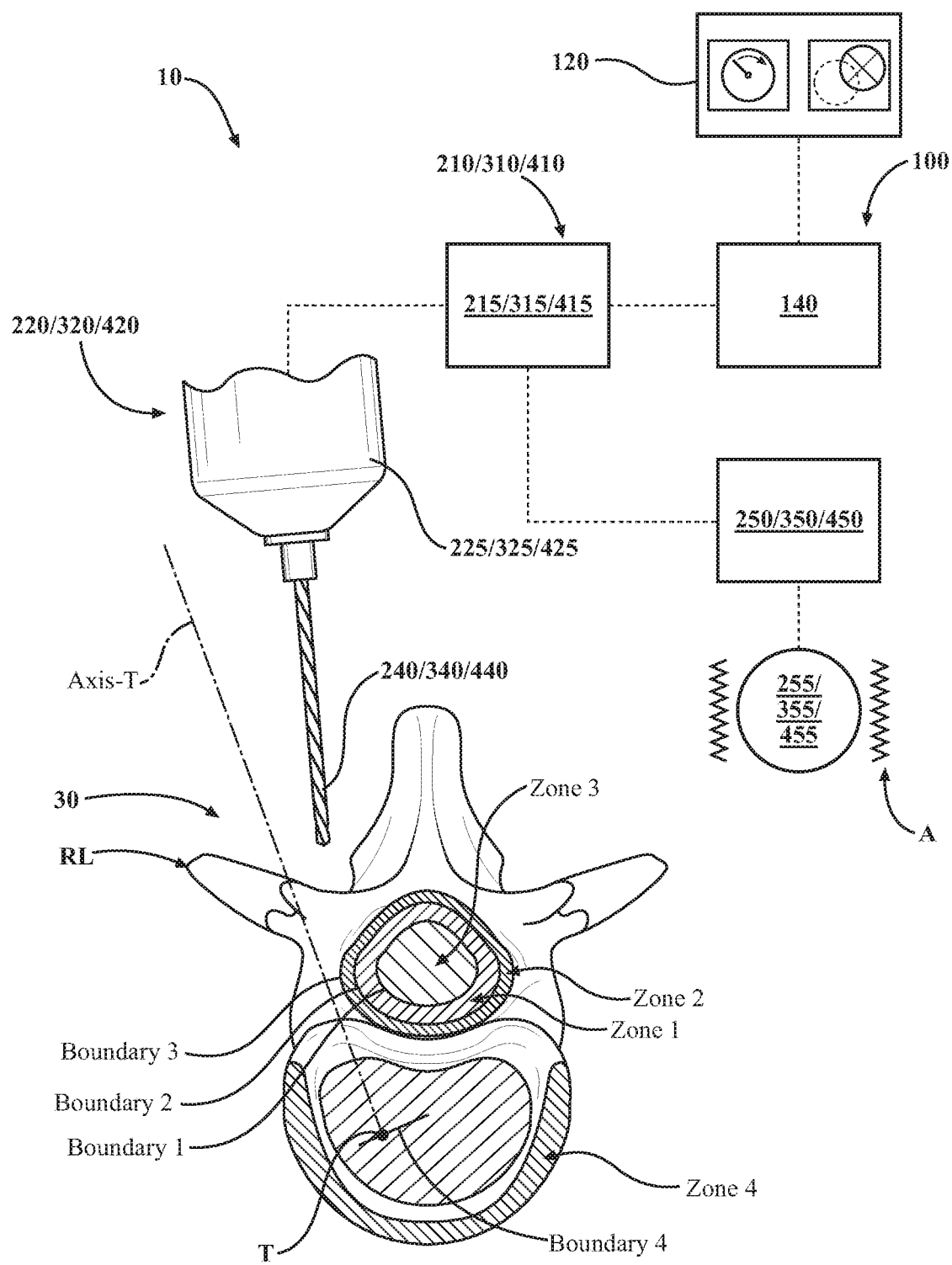
FIG. 5A is a schematic view of a second exemplary surgical instrument of the surgical system of FIGS. 1A-1B, the second surgical instrument oriented in a first position relative to the patient and a defined first set of exemplary alert zones.
Figure 5B:
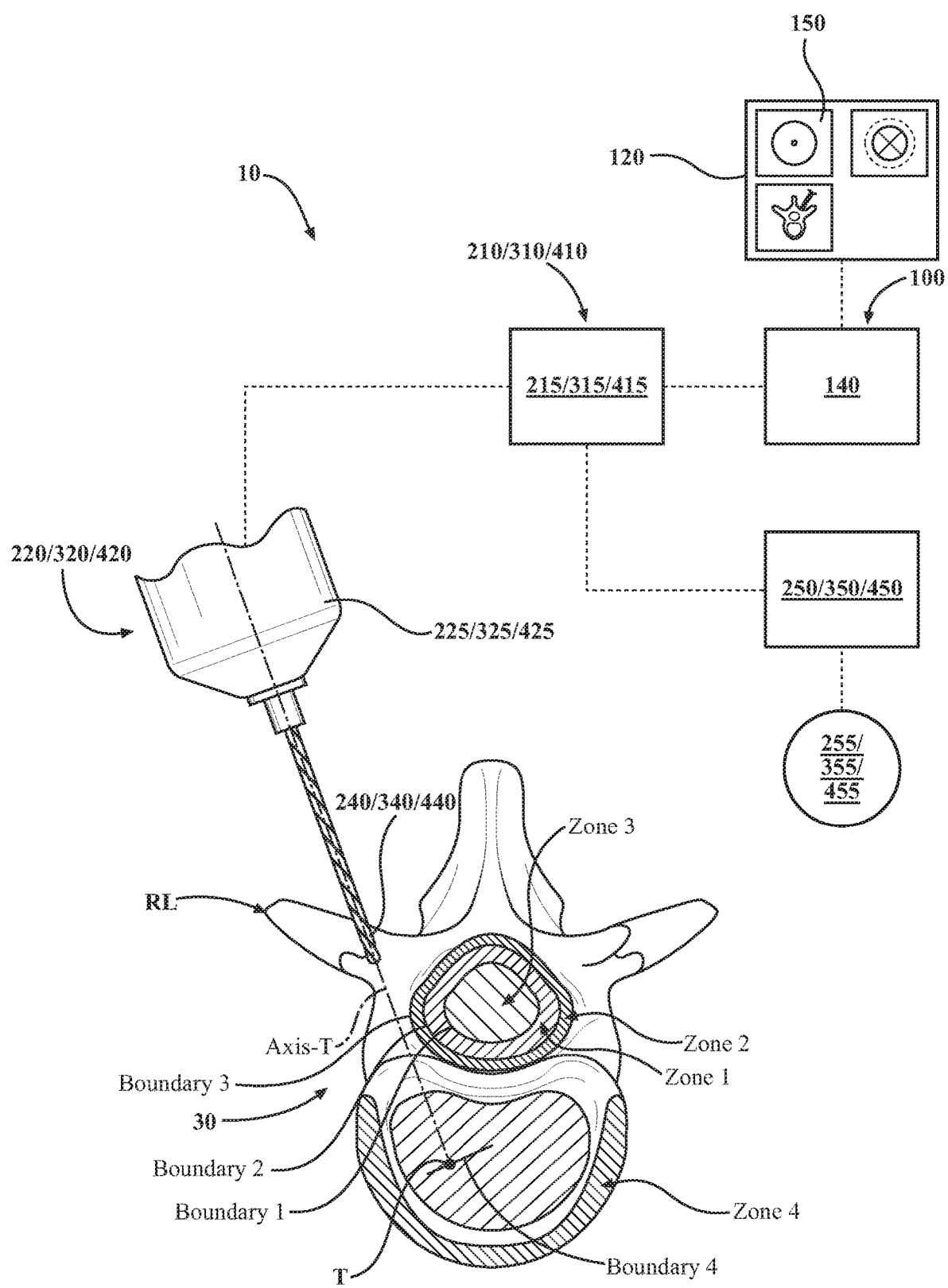
FIG. 5B is a schematic view of the second surgical instrument of FIG. 5A, the second surgical instrument oriented in a second position relative to the patient and the defined first set of exemplary alert zones.
Figure 5C:
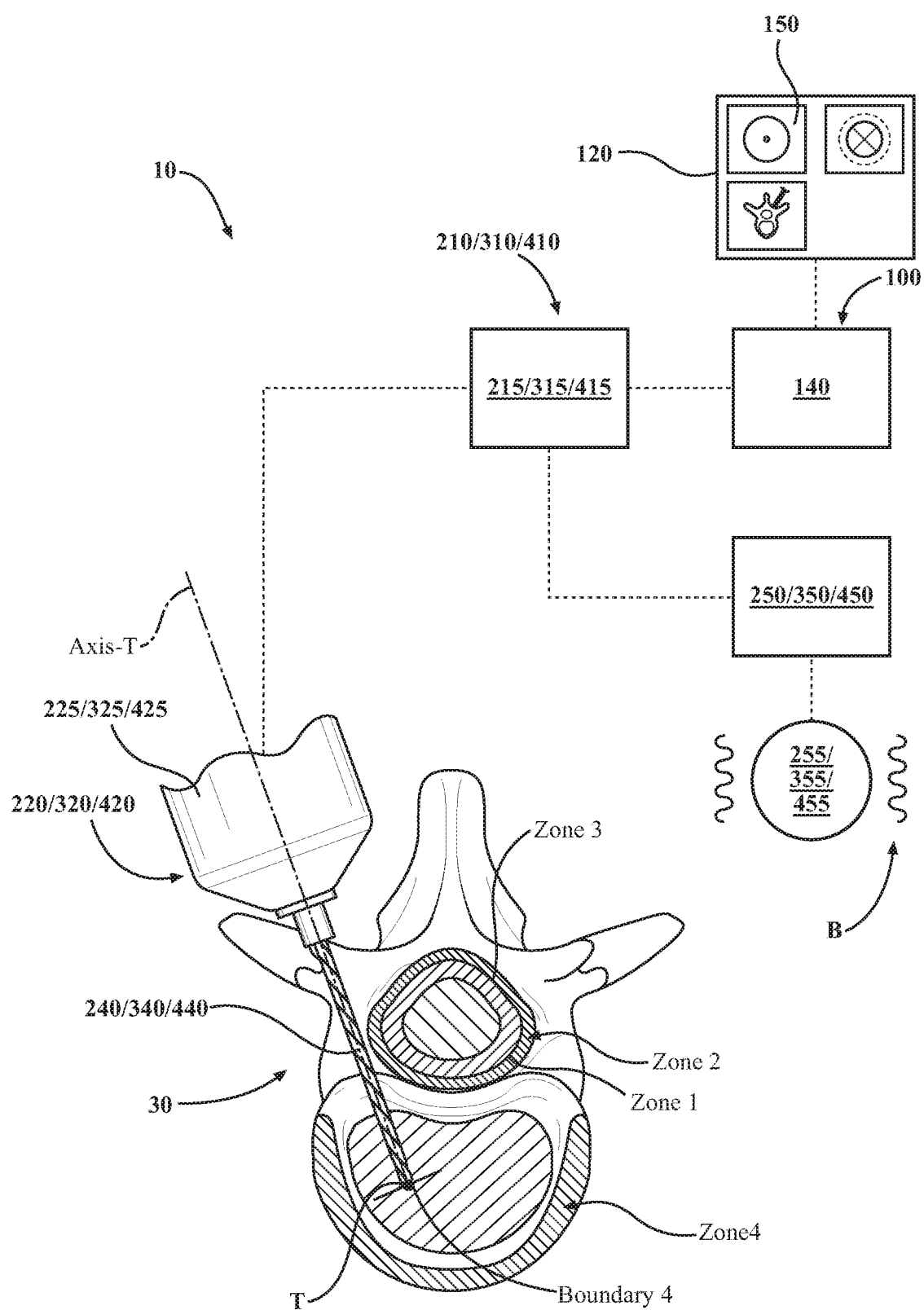
FIG. 5C is a schematic view of the second surgical instrument of FIG. 5A, the second surgical instrument oriented in a third position relative to the patient and the defined first set of exemplary alert zones.
Figure 5D:
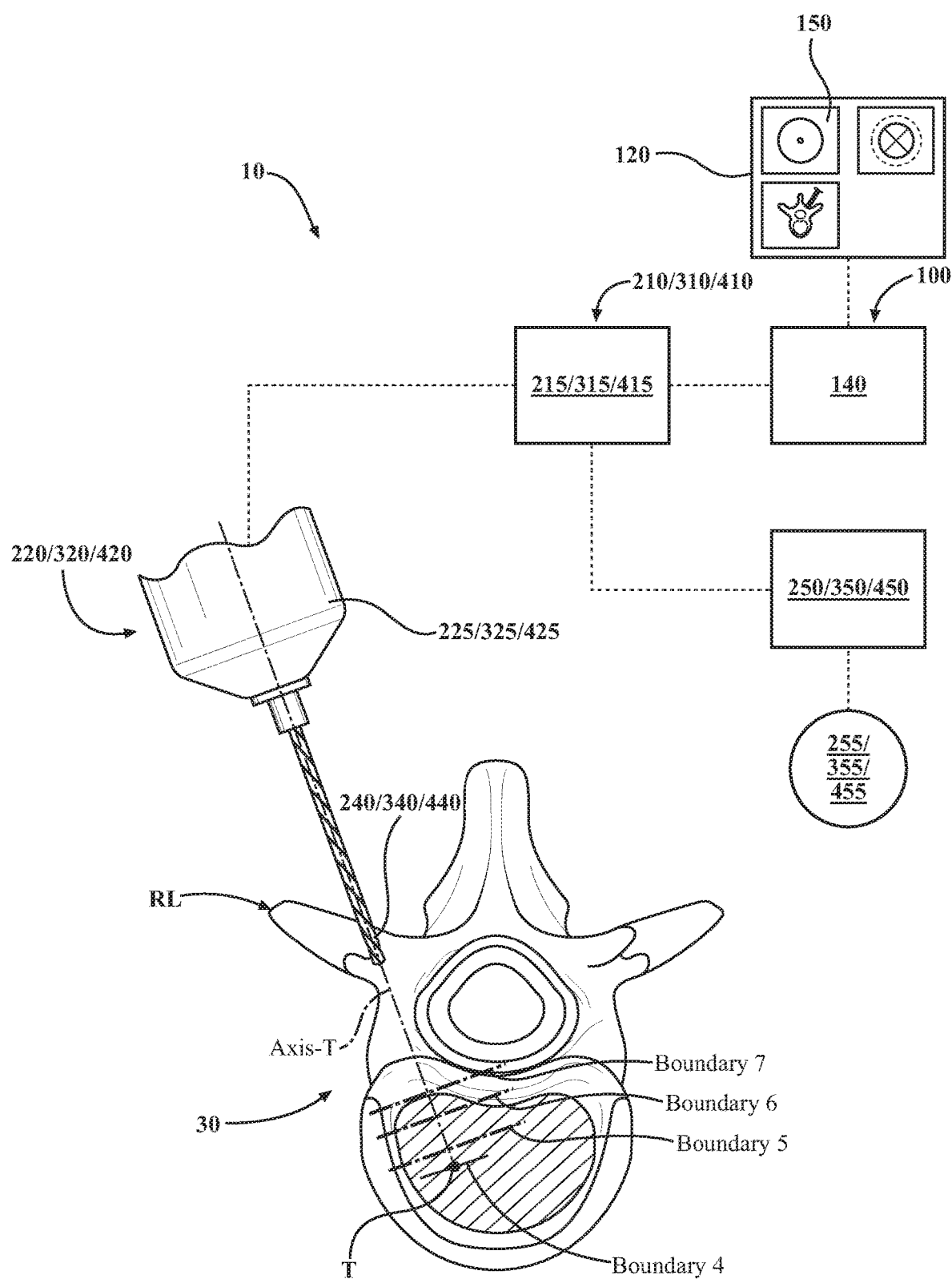
FIG. 5D is a schematic view of the second surgical instrument of FIG. 5A, the second surgical instrument oriented in the third position relative to the patient and a defined second set of exemplary alert zones.

Referring to FIGS. 5A-5F, various schematic views of one of the surgical instrument assemblies 200, 300, 400 described above including the surgical instrument 220, 320, 420 in various orientations relative to the patient 20 are illustrated. Referring to FIG. 5A, the surgical instrument 220, 320, 420, such as the first surgical instrument 220, is illustrated in a first position relative to the surgical site 30 on the patient. The surgical instrument 220, 320, 420 may be configured to bore a hole to remove biological tissue from the surgical site 30 or drive a screw, such as a pedicle screw, into a surgical site. In this scenario, the surgeon may select and/or define a planned implant pose, such as one or more planned screw poses, including a target trajectory, Axis-T, and a target depth T. the target trajectory, Axis-T, and the target depth T. Alternatively, the navigation processor 140 may receive a planned surgical pathway that was automatically generated based on the segmentation of the patient image data and the planned pose of the medical device or implant 275 to be inserted during the procedure.

The target trajectory, Axis-T, may comprise the desired orientation of the implant 275 to be inserted during the procedure, and may be utilized to align with the surgical instrument 220, 320, 420, and by extension the one or more end-effectors 240, 340, 440 when preparing the biological tissue for receiving the screw. The target depth T may comprise a desired depth or position in the known coordinate system. The target depth may also be referred to as a boundary and may be configured as a partial plane perpendicular to the target trajectory. It is also contemplated that the surgical navigation system 100 may be configured to define the target trajectory, Axis-T, and the target depth T based on information selected or input by the medical professional. For example, the surgical navigation system 100 may be configured to define the target trajectory, Axis-T, and the target depth T based on one or more of the following items input by the medical professional: the type procedure to be performed, the type or size of implant 275 to be used, the type of surgical instrument 220, 320, 420 to be used and/or the type end-effector 240, 340, 440.

In the first position, all portions of the end-effector 240, 340, 440 is outside the one or more defined virtual boundaries (Boundary 1, 2, 3, 4) and/or alert zones (Zones 1, 2, 3, 4). Therefore, no alert is required to notify the surgeon of possible contact with a critical anatomical structure. However, the surgical instrument 220, 320, 420, as determined by the surgical navigation system 100, is not aligned with the target trajectory, Axis-T. In this exemplary scenario, the surgical navigation system 100 may be configured to trigger one of the various alerts described above. For example, the surgical navigation system 100 may be configured to send a signal to the instrument processor 215, 315, 415 to activate the alert device 255, 355, 455 because the orientation of the end-effector 240, 340, 440 is not aligned with the target trajectory, Axis-T. The alert device 255, 355, 455, depending on the type of alert assigned to the target trajectory, Axis-T, may be configured to provide a tactile alert A, such as a vibrating the switch 250, 350, 450. Alternatively, the alert device 255, 355, 455 may be configured to provide a visual alert B, such as a blinking light. In yet another configuration, the alert device 255, 355, 455 may be configured to provide an audible alert C, such as a beeping noise. The surgical navigation system 100 may also be configured to send a signal to the instrument processor 215, 315, 415 to reduce the output of the motor 245, 345, 445 of the surgical instrument 220, 320, 420 to reduce the rotation of the end-effector 240, 340, 440 from a maximum cutting speed to a minimum cutting speed. Alternatively, the surgical navigation system 100 may be configured to disable or stop the rotation of the end-effector 240, 340, 440 until it has been aligned with the target trajectory, Axis-T, to prevent the end-effector 240, 340, 440 from boring a misaligned hole. It is also contemplated that a combination of the various alerts may be utilized, such as the alert device 255, 355, 455 producing a combination of a tactile alert A, a visual alert B, and an audible alert C. As is illustrated in FIG. 5A, the surgeon has assigned a tactile alert A, such as vibrating the switch 250, 350, 450 when the end-effector 240, 340, 440 is not aligned with the target trajectory, Axis-T. It also contemplated that one or more of the various alerts described above may be assigned in this scenario to notify the surgeon when the end-effector 240, 340, 440 is adjacent and/or distal to one of the virtual boundaries (Boundary 1, 2, 3, 4) and/or approaches and/or enters one of the various alert zones (Zones 1, 2, 3, 4).

Furthermore, it is also contemplated that the surgical navigation system 100 may be configured to only send a signal to activate an alert device 255, 355, 455 to produce one of the various alerts described above and/or to deactivate/disable the variable speed motor 245, 345, 445 to prevent actuation of the end-effector 240, 340, 440 when the end-effector 240, 340, 440 and/or surgical instrument 220, 320, 420 are positioned within a threshold distance of the patient and/or surgical site. This may be measured relative to a reference location RL and/or reference coordinate system defined in the known coordinate system, such as position on bone. By computing the distance between the reference location and the end effector, the navigation system can determine whether the surgical instrument is relatively close to the surgical site.

In the alternatively, the surgical navigation system 100 may be configured to allow the variable speed motor 245, 345, 445 to actuate the end-effector 240, 340, 440 uninterrupted irrespective of the position of the end-effector 240, 340, 440 and/or surgical instrument 220, 320, 420 relative to the target trajectory Axis-T when the end-effector 240, 340, 440 and/or surgical instrument 220, 320, 420 are outside a threshold distance, i.e. a safe distance, from the patient and/or surgical site. This may include deactivating all alert devices 255, 355, 455 when the end-effector 240, 340, 440 and/or surgical instrument 220, 320, 420 are outside a threshold distance from the patient and/or surgical site. This may allow the medical professional to test the surgical instrument 220, 320, 420 without interruption to make sure everything is in proper working order prior to approaching the surgical site and beginning the procedure. However, once the end-effector 240, 340, 440 and/or surgical instrument 220, 320, 420 are within the threshold distance of the reference location/reference coordinate system, the alert device 255, 355, 455 may be activated and the surgical navigation system 100 may again communicate all appropriate signals to processor 215, 315, 415 to activate the alert device 255, 355, 455 and/or deactivate the variable speed motor 245, 345, 445 in the manner described above.

Referring to FIG. 5B, the surgical instrument 220, 320, 420, such as the first surgical instrument 220, is illustrated in a second position relative to the surgical site 30 on the patient. In the second position, the end-effector 240, 340, 440 is spaced from the virtual boundaries (Boundary 1, 2, 3, 4) and/or outside the defined alert zones (Zones 1, 2, 3, 4). The end-effector 240, 340, 440 is also properly aligned with the target trajectory, Axis-T. In this exemplary scenario, the surgical navigation system 100 may identify that the end-effector 240, 340, 440 is spaced from one or more of the virtual boundaries (Boundary 1, 2, 3, 4) and/or outside the one or more defined alert zones (Zones 1, 2, 3, 4) and is aligned with the target trajectory, Axis-T, and allow the surgical instrument 220, 320, 420 to operate under normal working conditions when the switch 250, 350, 450 is manipulated to actuate the end-effector 240, 340, 440. The alert device 255, 355, 455 may be also be inactive in this scenario.

Referring to FIG. 5C, the surgical instrument 220, 320, 420, such as the third surgical instrument 220, is illustrated in a third position relative to the surgical site 30 on the patient. In the second position, the end-effector 240, 340, 440 is spaced from to one or more of the boundaries (Boundary 1, 2, 3, 4) and/or outside the one or more defined alert zones (Zones 1, 2, 3, 4). The end-effector 240, 340, 440 is also properly aligned with the target trajectory, Axis-T. However, the tip of the end-effector 240, 340, 440 has reached the target depth T, at or adjacent to boundary 5. In this exemplary scenario, the surgical navigation system 100 may identify that the end-effector 240, 340, 440 or implant 275 has reached the target depth T, and be configured to disable or stop the rotation of the end-effector 240, 340, 440 because it has reached the target depth T, to prevent the end-effector 240, 340, 440 from boring a hole beyond the depth of the target depth T. In addition, the surgical navigation system may be configured to trigger one of the various alerts described above. For example, the surgical navigation system 100 may be configured to send a signal to the instrument processor 215, 315, 415 to activate the alert device 255, 355, 455 because the end-effector 240, 340, 440 has reached the target depth T. The alert device 255, 355, 455, depending on the type of alert assigned to the target location T, may be configured to provide a tactile alert A, such as a vibrating the switch 250, 350, 450 upon the surgical navigation system 100 determining that the end-effector 240, 340, 440 has reached the target location T. Alternatively, the alert device 255, 355, 455 may be configured to provide a visual alert B, such as a blinking light. In yet another configuration, the alert device 255, 355, 455 may be configured to provide an audible alert C, such as a beeping noise. The surgical navigation system 100 may also be configured to send a signal to the instrument processor 215, 315, 415 to reduce the output of the motor 245, 345, 445 of the surgical instrument 220, 320, 420 to reduce the rotation of the end-effector 240, 340, 440 from a maximum cutting speed to a minimum cutting speed. It is also contemplated that a combination of the various alerts may be utilized, such as the alert device 255, 355, 455 producing a combination of a tactile alert A, a visual alert B, and an audible alert C. As is illustrated in FIG. 5A, the surgeon has assigned a visual alert B, such as a blinking light on the switch 250, 350, 450 when the end-effector 240, 340, 440, has reached the target depth T.

Figure 5E:
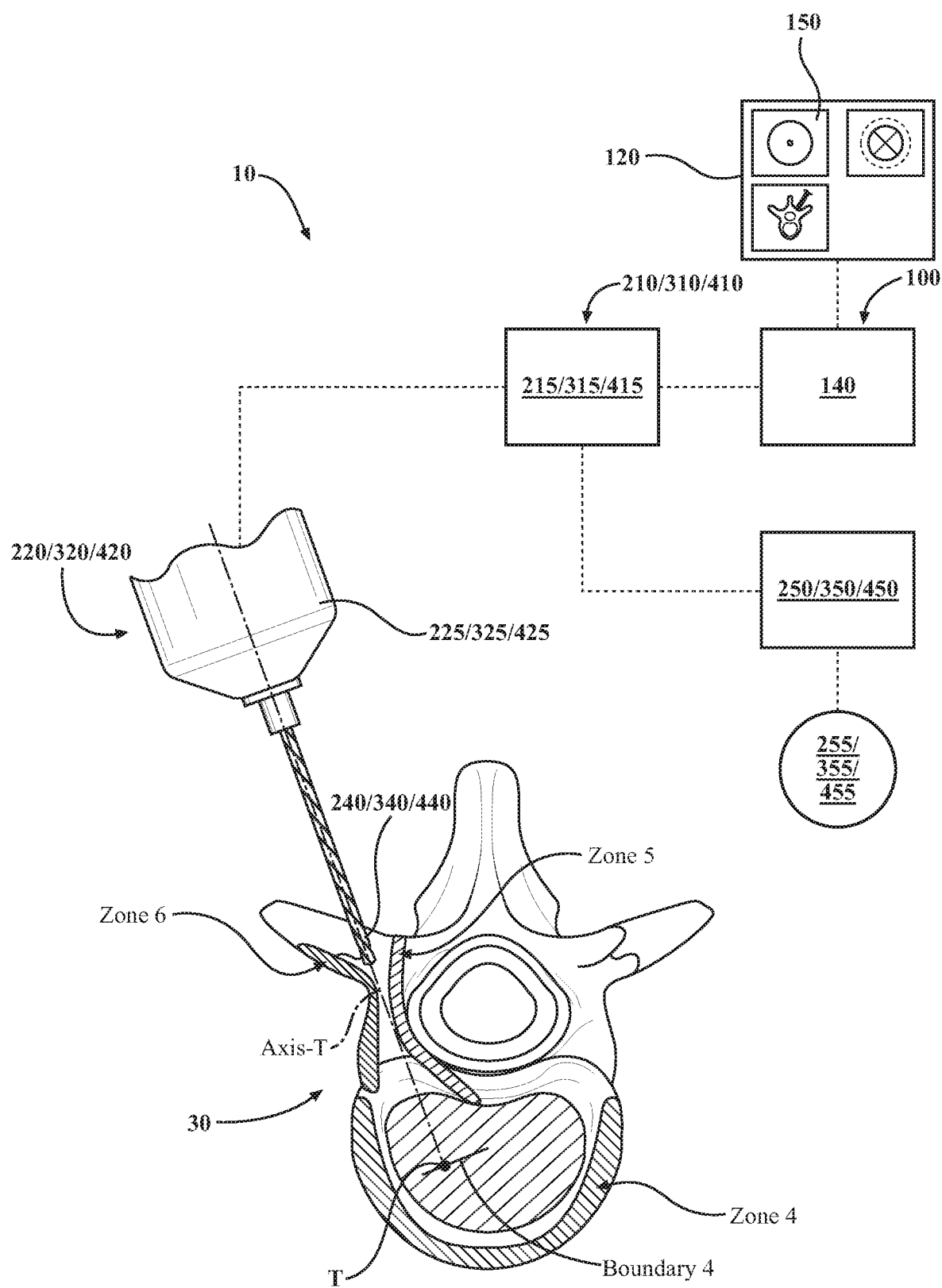
FIG. 5E is a schematic view of the second surgical instrument of FIG. 5A, the second surgical instrument oriented in the third position relative to the patient and a defined second set of exemplary alert zones.
Figure 5F:
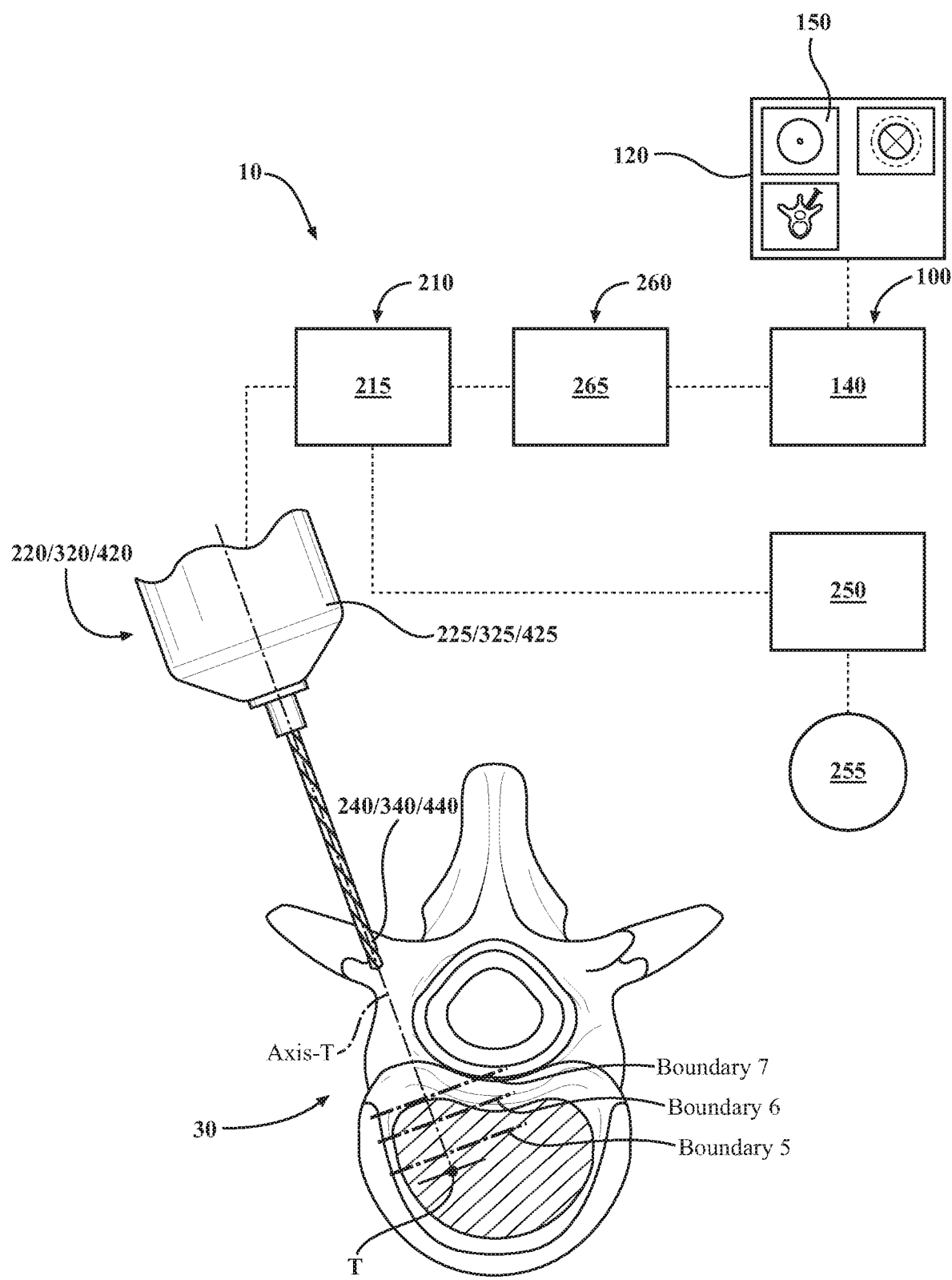
FIG. 5F is a schematic view of the second surgical instrument of FIG. 5A, the second surgical instrument further comprising a battery module and battery processor.

Referring to FIGS. 5D-5F, the surgical instrument 220, 320, 420, such as the first surgical instrument 220, is illustrated relative to the surgical site 30 on the patient. The first surgical instrument 220 may be configured to operate in a similar manner relative to the defined boundaries as described above with regard to FIG. 5A-5C. However, in FIGS. 5D-5F, some additional exemplary virtual boundaries (Boundary 4, 5, 6, 7) and/or alert zones are illustrated. For example, FIG. 5D illustrates various additional exemplary virtual boundaries (Boundary 4, 5, 6, 7). The virtual boundaries (Boundary 4, 5, 6, 7) may correspond to varying depths for inserting different end-effectors 240 that are coupled to the first surgical instrument 220. It is contemplated that a plurality of different end-effectors 240, which will be described in more detail below, may be coupled to the handpiece 225 of the first surgical instrument 220. Each of the different end-effectors 240 may be configured to perform a different function and/or operation as part of executing the surgical procedure on the patient. The surgical navigation system 100 may be configured to identify which of the end-effectors 240 is coupled to the handpiece 225 and define a corresponding virtual boundary (Boundary 4, 5, 6, 7) and/or alert zone that corresponds to each of the respective end-effectors 240A, 240B, 240C. The fourth virtual boundary, Boundary 4, may correspond to the target depth of the selected implant 275. Each of the fourth, fifth, and sixth virtual boundaries (Boundary 5, 6, 7) may be configured to correspond to a target depth for each the respective end-effectors 240A, 240B, 240C. Each of the virtual boundaries (Boundary 5, 6, 7) corresponding to each of the respective end-effectors 240A, 240B, 240C may be determined as a defined distance from the fourth virtual boundary, Boundary 4, based on the desired depth and/or position of the corresponding end-effectors 240A, 240B, 240C. It is also contemplated that the fourth virtual boundary, Boundary 4, and the fifth virtual boundary, Boundary 5, are positioned at the same location. In this scenario, the fifth virtual boundary, Boundary 5, corresponding to the first end-effector 240A may define the initial target depth of the implant 275, and each of the subsequent virtual boundaries (Boundary 6, 7) may be defined based on a distance from the fifth virtual boundary, Boundary 5. For example, a first end-effector 240A may comprise a drill, a second end-effector 240B may comprise a tap, and a third end-effector 240C may comprise a driver as used in the surgical procedure of preparing and inserting a pedicle screw into a vertebra. As illustrated in FIG. 5D, the fifth virtual boundary (Boundary 5) may be defined by the surgical navigation system 100 to correspond to the depth for the first end-effector 240A, the sixth virtual boundary (Boundary 6) may be defined by the surgical navigation system 100 to correspond to the depth for the second end-effector 240B, and the seventh virtual boundary (Boundary 7) may be defined by the surgical navigation system 100 to correspond to the depth for the third end-effector 240C. Each of the virtual boundaries (Boundary 4, 5, 6, 7) may comprise a plane perpendicular the axial location along the target axis, Axis-T, corresponding to a target depth for the attached end-effector 240A, 240B, 240C. The navigation system 100 may be configured to define the virtual boundaries (Boundary 4, 5, 6, 7) based on the position of the surgical instrument and a known position of a tip of the respective end-effector 240A, 240B, 240C that is coupled to the handpiece 225.

One or more of the various alerts and/or alert devices 255, 355, 455 described above may assigned to each of the various virtual boundaries (Boundary 4, 5, 6, 7). While the virtual boundaries (Boundary 4, 5, 6, 7 are described as being defined by the surgical navigation system 100, it is also contemplated that they may be defined and/or selected by the medical professional. For example, the medical professional may define or select the virtual boundaries (Boundary 4, 5, 6, 7) within the patient data using the user input device 130 or the graphical user interface (GUI) 150. It is also contemplated that the virtual boundaries (Boundary 4, 5, 6, 7) may be defined and/or recommended by the surgical navigation system 100, and the medical professional may modify or alter the virtual boundaries (Boundary 4, 5, 6, 7) defined by the surgical navigation system 100 using the user input device 130 and/or the graphical user interface (GUI) 150.

Referring to FIG. 5E, the surgical instrument 220, 320, 420, such as the first surgical instrument 220, is illustrated relative to the surgical site 30 on the patient. The first surgical instrument 220 may be configured to operate in a similar manner relative to the defined alerts zones as described above with regard to FIG. 5A-5C. FIG. 5E illustrates and alternative exemplary configuration of the alert zones (Zones 5, 6). As described above, the alert zones may be defined encircle or abut critical anatomical structures, such as Zones 1, 2, and 3 illustrated in FIGS. 4A-5C to alert the medical professional when approaching the critical anatomical structure. The alert zones may also be defined to identify borders of anatomical structures, such as Zone 4 illustrated in FIGS. 5A-5D to alert the medical professional when approaching a boundary and to avoid breaching the cortical wall. As illustrated in FIG. 5E, alert zones (Zones 5, 6) may be defined along boundaries on opposing sides of the target trajectory, Axis-T, to alert the medical profession of any deviation from the target trajectory, Axis-T. The alert zones (Zones 5, 6) may also be shaped or contoured to match the shape of critical anatomical structures and/or boundaries. For example, the surgical navigation system 100 may be configured to define the alert zone (Zone 6) such that it is curved around the outer perimeter of the pedicle to alert the medical professional when the end-effector 240 of the first surgical instrument 220 is approaching the outer perimeter of the vertebra to prevent the medical profession from breaching the outer perimeter of the pedicle. The surgical navigation system 100 may also be configured to define the alert zone (Zone 5) such that it is contoured around a critical anatomical structure (the central foramen) within the vertebra to alert the medical professional when the end-effector 240 of the first surgical instrument 220 is approaching the critical anatomical structure to prevent the medical profession from contacting the critical anatomical structure.

Referring to FIG. 5F, surgical instrument 220, 320, 420, such as the first surgical instrument 220, is illustrated relative to the surgical site 30 on the patient. The virtual boundaries (Boundary 4, 5, 6, 7) are similar to those described with regard to FIG. 5D above. However, the system in FIG. 5F illustrates an alternative arrangement of the components, wherein the surgical instrument also comprises a battery module 260, the battery module comprising a battery processor 265. The system may be configured such that the navigation processor 140 is in communication with the battery processor 265. The battery processor 265 may receive the signal from the navigation processor 140 to manipulate the flow of power from the battery module 260 to handpiece 225, and by extension the variable speed motor 245, based on the position of the surgical instrument relative to the virtual boundaries (Boundary 4, 5, 6, 7). The signal from the navigation processor 140 may be configured to indicate to the battery processor 265 that the position of the end-effector 240 is adjacent and/or distal to virtual boundaries (Boundary 4, 5, 6, 7), causing the battery processor 265 to discontinue the flow of power from the battery module 260 to handpiece 225, and by extension the variable speed motor 245. Alternatively, it is also contemplated that the signal from the navigation processor 140 may include a command to the battery processor 265 directing the battery processor 265 to discontinue the flow of power from the battery module 260 to handpiece 225, and by extension the variable speed motor 245, based on that the navigation system 100 determining the position of the end-effector 240 being adjacent and/or distal to virtual boundaries (Boundary 4, 5, 6, 7). The battery processor 265 may also be in communication with the instrument processor 215, such that the instrument processor 215 may be configured to deactivate the motor based on data received from the battery processor.

Figure 6:
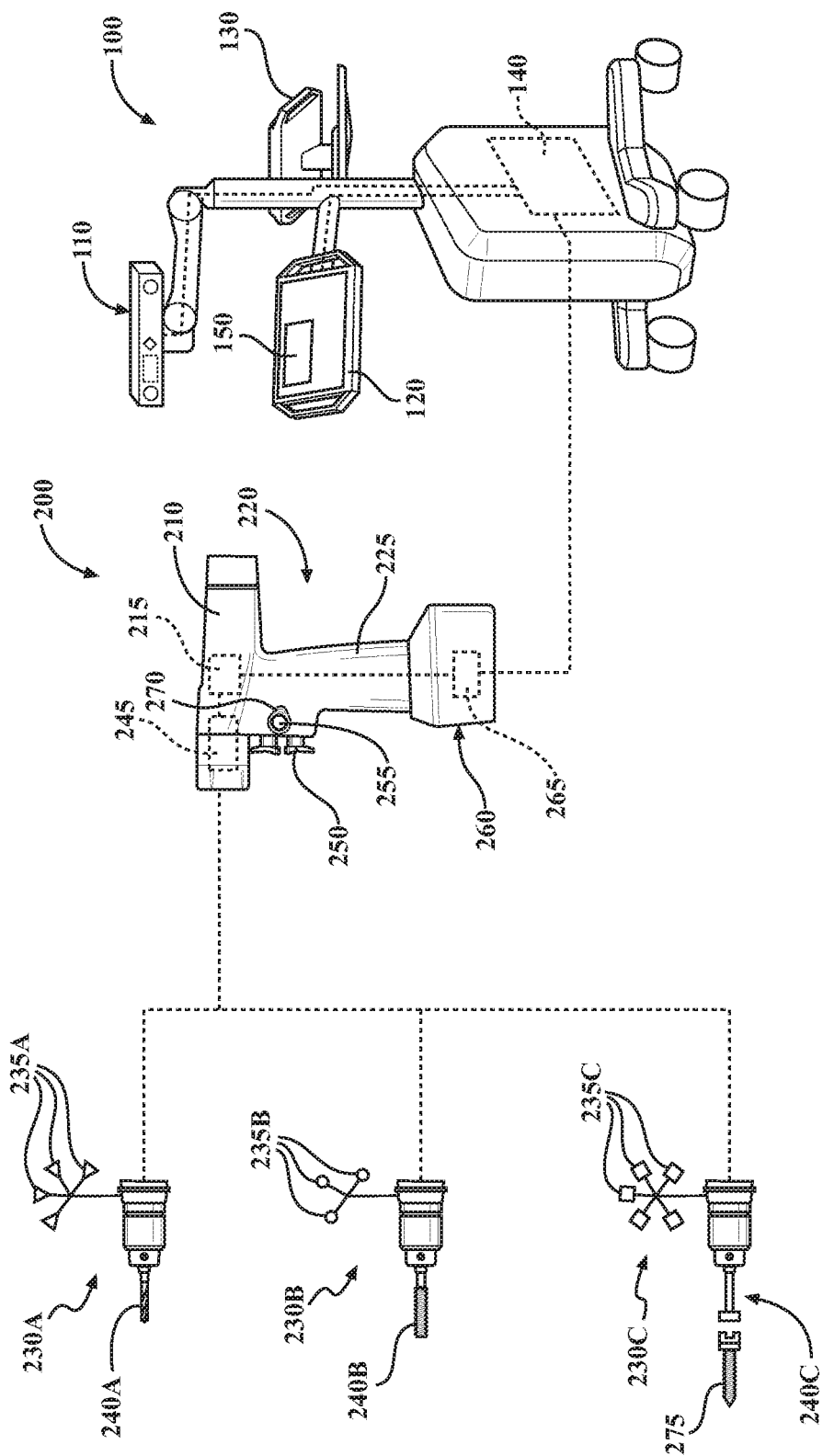
FIG. 6 is a schematic of an exemplary surgical system including a navigation system and a hand-held surgical instrument, the hand-held surgical instrument comprising a battery module and a plurality of end-effectors.

Referring to FIG. 6, an exemplary configuration of a surgical system is illustrated including the surgical navigation system 100 and the first surgical instrument 220 described above. While only the first surgical instrument is illustrated in FIG. 6, it is contemplated that any of the surgical instruments 220, 320, 420 described above may be included in the system. The surgical system may also comprise a plurality of end-effectors 240A, 240B, 240C that are removably couplable to the handpiece 225 of the first surgical instrument 220. The end-effectors 240A, 240B, 240C may also be referred to as end-effectors, surgical attachments, and/or tool attachments. For example, the surgical system may comprise a first end-effector 240A comprising a drill for cutting and/or boring a hole in biological material. The surgical system may also comprise a second end-effector 240B comprising a tap for creating threads on the interior surface of a hole or aperture. The surgical system may also comprise a third end-effector 240C comprising a driver for driving or inserting a screw within the hole or aperture. Each of the end-effectors 240A, 240B, 240C may comprise an instrument tracking device 230A, 230B, 230C comprising a unique configuration and/or arrangement of markers 235A, 235B, 235C. For example, markers 235A, 235B, 235C of the instrument tracking devices 230A, 230B, 230C may comprise a unique size, shape, and/or arrangement relative to the markers 235A, 235B, 235C of the other instrument tracking devices 230A, 230B, 230C. While not illustrated in the figures, it is also contemplated that each of the end-effectors 240A, 240B, 240C may be coupled to a separate handpiece 225, wherein each of the of the handpieces 225 may comprise a tracking device 230A, 230B, 230C having a unique configuration and/or arrangement of markers 235A, 235B, 235C. For example, markers 235A, 235B, 235C of the instrument tracking devices 230A, 230B, 230C may comprise a unique size, shape, and/or arrangement relative to the markers 235A, 235B, 235C of the other instrument tracking devices 230A, 230B, 230C. The navigation system 100 may be configured to identify the end-effectors 240A, 240B, 240C based on a known association with a particular handpiece 225 and the unique size, shape, and/or arrangement relative to the markers 235A, 235B, 235C of the instrument tracking devices 230A, 230B, 230C that is attached to the specific handpiece 225. The navigation system may then be configured to provide the virtual boundaries (Boundary 4, 5, 6, 7) and/or alert zones (Zones 4, 5, 6, 7) for the appropriate end-effectors 240A, 240B, 240C that are presently being navigated.

The surgical navigation system 100 may be configured to identify which of the end-effectors 240A, 240B, 240C is coupled to the handpiece 225 of the first surgical instrument based on the arrangement and/or configuration of the markers 235A, 235B, 235C of the instrument tracking devices 230A, 230B, 230C. The surgical navigation system 100 may then be configured to define various alert zones. For example, the surgical navigation system 100 may be configured to define an alert zone and/or boundary corresponding to the target depth for each of the individual end-effectors 240A, 240B, 240C. An exemplary configuration of the virtual boundaries (Boundary 4, 5, 6, 7) and/or alert zones, Zones 5, 6, and 7, are illustrated in FIG. 5D, wherein Boundary 5 may correspond to the target depth for the first end-effector 240A, Boundary 6 may correspond to the target depth for the second end-effector 240B, and Boundary 7 may correspond to the target depth for the third end-effector 240C. The surgical navigation system 100 may be programmed and/or configured to manipulate the speed of the motor 245, 345, 445 of the surgical instrument 220, 320, 420, and/or activating an alert device 255, 355, 455, upon the surgical navigation system 100 determining the surgical instrument 220, 320, 420 is at/or adjacent to one or more of the virtual boundaries (Boundary 4, 5, 6, 7) or has entered one of the defined alert zones. For example, when the surgical navigation system 100 detects that that the first end-effector 240A is coupled to the handpiece 225, the surgical navigation system 100 may be configured to transmit a signal to the processor 215, 315, 415 of the surgical instrument 220 to deactivate the variable speed motor 245, 345, 445 when the first end-effector 240A is adjacent and/or distal to Boundary 5. When the surgical navigation system 100 detects that that the second end-effector 240B is coupled to the handpiece 225, the surgical navigation system 100 may be configured to transmit a signal to the processor 215, 315, 415 of the surgical instrument 220 to deactivate the variable speed motor 245, 345, 445 when the second end-effector 240B is adjacent and/or distal to Boundary 6. When the surgical navigation system 100 detects that that the third end-effector 240C is coupled to the handpiece 225, the surgical navigation system 100 may be configured to transmit a signal to the processor 215, 315, 415 of the surgical instrument 220 to deactivate the variable speed motor 245, 345, 445 when the third end-effector 240C is adjacent and/or distal to Boundary 7. In other words, only certain alert zones and/or virtual boundaries are active for certain end effectors. When the appropriate end effector enters the field, the surgical navigation system only activates the appropriate virtual boundaries and/or alert zones that are suitable for the identified end effector.

Once the surgical navigation system 100 has transmitted a signal to the processor 215, 315, 415 of the surgical instrument 220, 320, 420 to deactivate the variable speed motor 245, 345, 445 upon the end-effector 240, 340, 440 being adjacent and/or distal to one of the virtual boundaries and/or entering one of the various alert zones, the processor 215, 315, 415 deactivates the variable speed motor 245, 345, 445, such as causing the motor to rotate at 0 rpms. While the end-effector 240, 340, 440 remains adjacent and/or distal to one of the virtual boundaries and/or within one of the various alert zones, after the temporarily deactivating the variable speed motor 245, 345, 445, the processor 215, 315, 415 may be configured to reactivate the variable speed motor 245, 345, 445. The variable speed motor 245, 345, 445 may be reactivated by the processor 215, 315, 415 following a defined period of time, such as the passage of greater than 1, 2, 3, or 4 o seconds.

Alternatively, variable speed motor 245, 345, 445 may be reactivated by the processor 215, 315, 415 following the processor 215, 315, 415 receiving a signal that the switch 250, 350, 450 has been manipulated by the user. For example, the processor to analyze the cadence of switch activations within a defined period of time. For example, the processor 215, 315, 415 may be configured to reactivate the variable speed motor 245, 345, 445 after receiving a signal from the switch sensor that the switch 250, 350, 450 has been manipulated between the second position, to the first position and back to second position within half-a-second. The time and number of times the switch 250, 350, 450 are manipulated are only intended as one example cadence and/or time frame for manipulating the switch 250, 350, 450 to reactivate the variable speed motor 245, 345, 445 following the variable speed motor 245, 345, 445 being deactivated for entering an alert zone. In one example, the processor 215, 315, 415 may reactivate the motor 245, 345, 445 when the trigger or footswitch 250, 350, 450 has been fully released.

Once the motor 245, 345, 445 is reactivated, control of the speed of the end effector 240, 340, 440 may be performed by manipulation of the switch or trigger 250, 350, 450, as is the case for normal operation.

Once the variable speed motor 245, 345, 445 has been reactivated while the end-effector 240, 340, 440 is adjacent and/or distal to one of the virtual boundaries and/or still within one of the various alert zones, the surgical navigation system 100 will continue tracking the position of the end-effector 240, 340, 440 and/or the surgical instrument 220, 320, 420.

However, after reactivation, the surgical navigation system 100 may be configured to send a subsequent signal to the processor 215, 315, 415 to once again manipulate the speed of and/or to deactivate the variable speed motor 245, 345, 445 if the surgical navigation system 100 detects that the end-effector 240, 340, 440 and/or the surgical instrument 220, 320, 420 are moving further in a distal direction relative to the boundary and/or further into the alert zone, or have traveled a threshold distance distal to the boundary and/or through a portion of the alert zone. For example, the surgical navigation system 100 may be configured to send a subsequent signal to the processor 215, 315, 415 to once again deactivate the variable speed motor 245, 345, 445 if the surgical navigation system 100 detects that the end-effector 240, 340, 440 has moved two millimeters distal to the virtual boundary and/or further into the alert zone. The surgeon would then need to once again go through one of the processes described above to reactivate the variable speed motor 245, 345, 445 again. The navigation processor 140 and/or the instrument processor 215, 315, 415 may be configured to only allow a limited number of reactivations, and/or may only allow reactivations when the end effector 240, 340, 440 is within a threshold distance of the boundary and/or zone.

Alternatively, once the variable speed motor 245, 345, 445 has been reactivated while the end-effector 240, 340, 440 is adjacent and/or distal to one of the virtual boundaries and/or still within one of the various alert zones, the surgical navigation system 100 may be configured allow the variable speed motor 245, 345, 445 to operate uninterrupted if the surgical navigation system 100 determines that the end-effector 240, 340, 440 is being moved in a proximal direction relative to virtual boundary and/or being withdrawn from the alert zone. In other words, once the navigation system 100 determines that the end-effector 240, 3240, 440 is being reversed, navigation processor 140 and/or the instrument processor 215, 315, 415 may be configured to allow for normal operation of the surgical instrument 220, 320, 420.

The first surgical instrument 220 may also comprise a mode switch 270 configured to alter an operational characteristic of the variable speed motor 245. The switch may be configured to be slidable and/or rotatable between two or more positions. For example, may have a first position and a second position, wherein the mode switch may be configured to switch the variable speed motor between a high speed and a low speed based on the position of the mode switch. Alternatively, the mode switch may be configured to switch the variable speed motor between a high torque and a low torque operating mode based on the position of the mode switch. In yet another configuration, the mode switch may be configured to switch the variable speed motor between a high speed and low torque operating mode and a low speed and high torque operating mode based on the position of the mode switch. The operating mode may be selected by the medical professional based on the type of procedure to be performed. For example, when performing a drilling process, the medical professional may want the surgical instrument 220 in a high speed and low torque operating mode. Alternatively, when performing a driving process, the medical professional may want the surgical instrument 220 in a low speed and high torque operating mode.

The surgical navigation system 100 may also be configured to determine the position of the mode switch 270. The surgical instrument 220 may comprise a mode switch sensor that detect the position of the mode switch 270. The processor 215 may then be configured to communicate the position of the mode switch to the surgical navigation system 100. Alternatively, the mode switch may comprise a tracker that allows the surgical navigation system 100 to determine the position of the mode switch 270. In yet another configuration, the surgical navigation system 100 may be configured to use machine vision to determine the position of the mode switch 270. As described above, the surgical navigation system may also be configured to determine which of the plurality of end-effectors 240A, 240B, 240C is coupled to the handpiece 225 of the surgical instrument 220. As mentioned above, a specific operating mode may be advantageous for different procedures. Therefore, the surgical navigation system 100 may be configured to compare the end-effector 240A, 240B, 240C against the operating mode, based on the identified position of the mode switch 270. The surgical navigation system 100 may then be configured to send a signal to the processor 215, 265 of the surgical instrument 220 to prevent operation of the handpiece 225 if the position of the mode switch 270 does not match the preferred operating mode of the end-effector 240A, 240B, 240C coupled to the handpiece 225. For example, if a drill-type end-effector 240A is coupled to the handpiece 225, with a recommended operating mode of high speed and low torque, and the mode switch 270 is in the low speed and high torque position, the surgical navigation system 100 may send a signal to the processor 215, 265, and the processor 215, 265 may be configured to prevent energization of the variable speed motor 245 until the mode switch 270 is moved to the high speed and low torque position.

Figure 7:
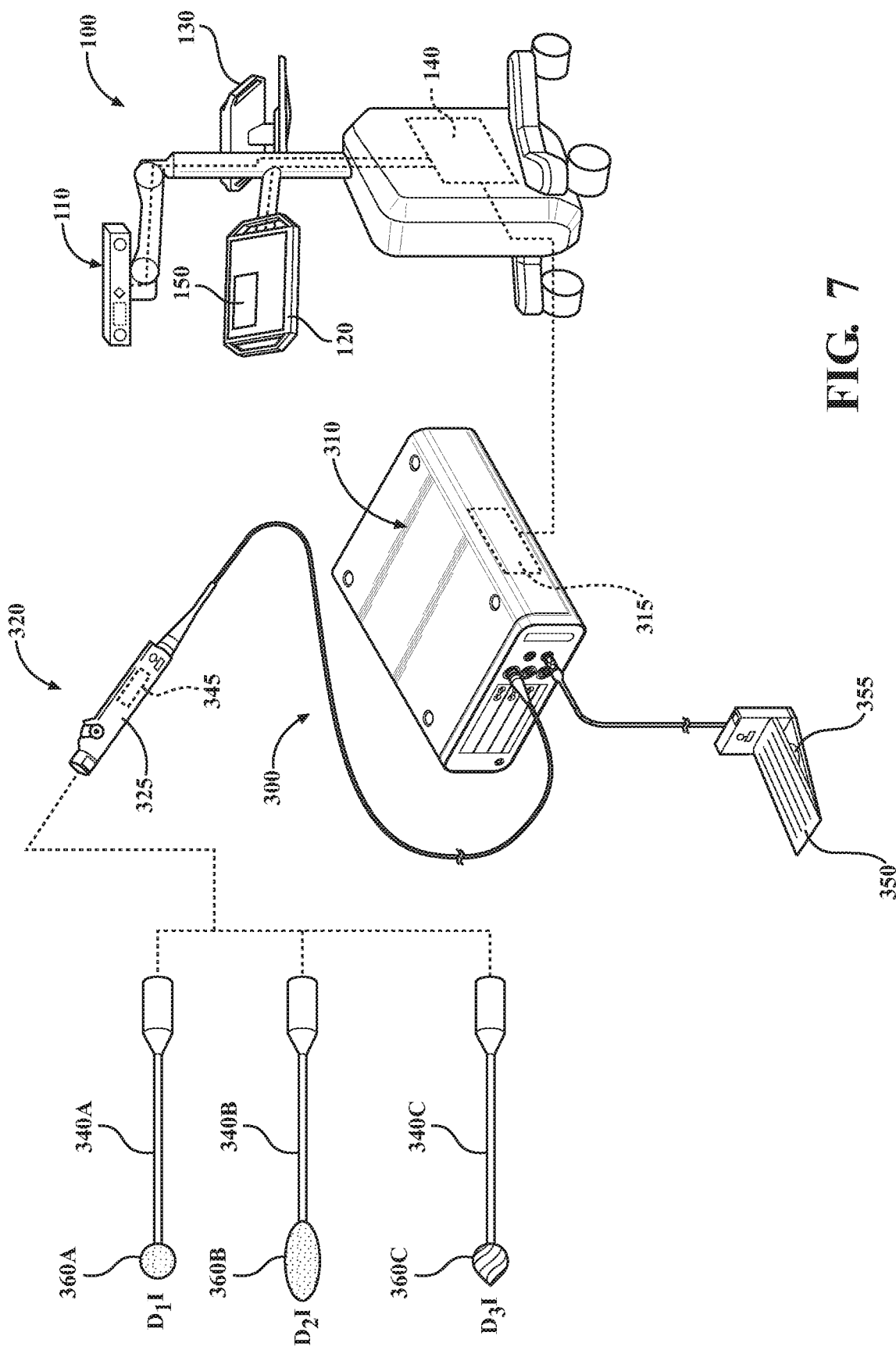
FIG. 7 is a schematic of an exemplary surgical system including a navigation system and a high-speed bur, the high-speed bur comprising a control console and a plurality of cutting burs.

Referring to FIG. 7, an exemplary configuration of a surgical system is illustrated including the surgical navigation system 100 and the second surgical instrument 320 described above. While only the first surgical instrument is illustrated in FIG. 6, it is contemplated that any of the surgical instruments 220, 320, 420 described above may be included in the system. The surgical system may also comprise a plurality of end-effectors 340A, 340B, 340C that are removably couplable to the handpiece 325 of the second surgical instrument 320. The end-effectors 340A, 340B, 340C may also be referred to as end-affecters, surgical attachments, and/or tool attachments. For example, the surgical system may comprise a first end-effector 340A comprising a first bur head 360A having a first diameter head D1. The surgical system may also comprise a second end-effector 340B a second bur head 360B having a second diameter head D2. The surgical system may also comprise a third end-effector 340C a third bur head 360C having a first diameter head D3. It is also contemplated that the head of each the end-effector 340A, 340B, 340C may vary by shape, material, and/or cutting type. It is also contemplated that the length of the shaft may vary from one end-effector 340A, 340B, 340C to the next.

The surgical navigation system 100 may be configured to identify which of the end-effectors 340A, 340B, 340C is coupled to the handpiece 325. One exemplary manner of identifying the end-effectors 340A, 340B, 340C that is coupled to the handpiece 325 is using machine vision. In this exemplary configuration, the surgical navigation system 100 may be configured to identify the end-effectors 340A, 340B, 340C that is coupled to the handpiece 325 based on the characteristics of each of the various end-effectors 340A, 340B, 340C. For example, the surgical navigation system 100 may be configured to identify the end-effectors 340A, 340B, 340C based on the diameter D1, D2, D3 of the head 360A, 360B, 360C. The surgical navigation system 100 may then be configured to define various alert zones based on the identified end-effector 340A, 340B, 340C. For example, the surgical navigation system 100 may be configured to define an alert zone surrounding one or more critical anatomical structures. An exemplary configuration of the virtual boundaries (Boundary 1, 2, 3) and/or alert zones (Zones 1, 2, and 3), are illustrated in FIGS. 4A-4D. The various virtual boundaries and/or alert zones may be based on varying distances around a single critical anatomical structure, or multiple critical anatomical structures may be identified using one or more virtual boundaries and/or alert zones. The surgical navigation system 100 may be programmed and/or configured to execute any of the various alert types, such as deactivating the surgical instrument 220, 320, 420, or activating an alert device 255, 355, 455, upon the surgical navigation system 100 determining the surgical instrument 220, 320, 420 has entered one of the define alert zones. For example, different end-effector diameters may have different thickness alert zones. In other words, the depth of the alert zones relative to the critical structure and/or boundaries may be automatically adjusted and/or set by the navigation system 100 based on the identification of the end-effector 240, 340, 440.

Figure 8:
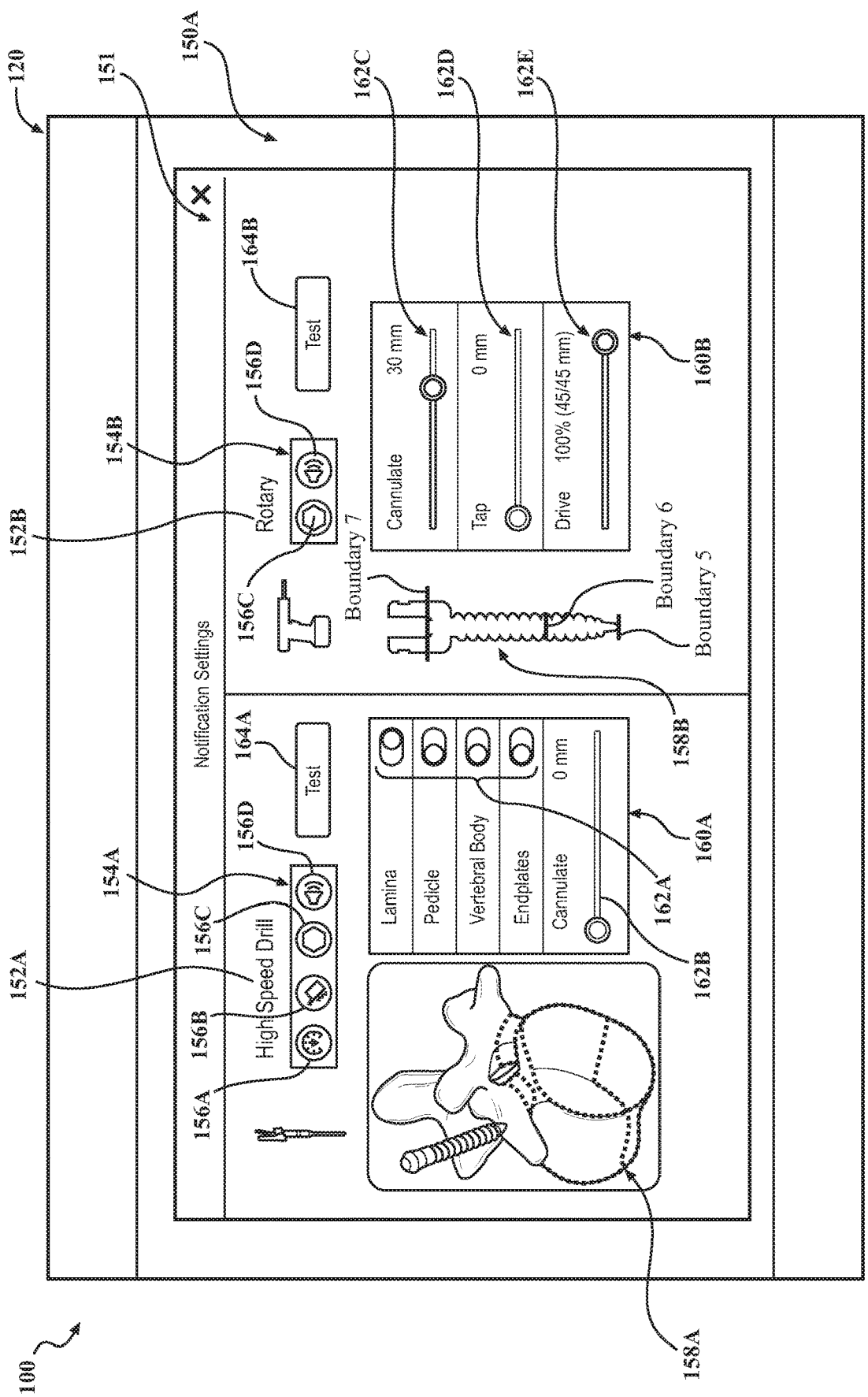
FIG. 8 is a schematic view of an exemplary graphical user interface (GUI) of a navigation system, the graphical user interface including user-selectable objects related to planning and/or execution of a surgical procedure.

Referring to FIG. 8, an exemplary configuration of the graphical user interface (GUI) 150 of the navigation system 100 is illustrated. The graphical user interface (GUI) 150 may configured as a touch screen on the display 120 of the navigation system 100. As illustrated in FIG. 8, the graphical user interface (GUI) 150 may comprise a plurality of buttons and/or prompts that are selectable and/or manipulatable by the surgeon. For example, the graphical user interface (GUI) 150 may comprise an exemplary alert interface 151 or window including a number of buttons that are selectable or manipulatable by the user to modify or adjust the various settings for the alerts to be provided during the execution of a medical procedure. The alert setup interface 151 may comprise a tool selection button 152A, 152B. The tool selection button 152A, 152B may allow the surgeon to select the surgical instrument assembly 200, 300, 400 from a populated list of surgical instruments, or may allow the surgeon to input a specific surgical instrument assembly 200, 300, 400 that will be utilized during exception of the surgical procedure. For example, the tool selection button 152A, 152B may allow the surgeon to select the second surgical instrument 320 including a high-speed cutting bur. This identifies the particular surgical instrument 320 to the navigation system 140, allowing the navigation system to populate the various virtual boundaries and/or alert zones that will be utilized for the identified instrument. The tool selection button 152A, 152B may also be configured to allow the surgeon to select the surgical instrument assembly 200, 300, 400, as well as one or more end-effectors 240, 340, 440 that may be coupled to the surgical instrument 220, 320, 420. For example, the surgeon may select the first surgical instrument 220, and further selected one or more of the end-effectors 240A, 240B, 240C that may be utilized during procedure to allow the navigation system to populate the various virtual boundaries and/or alert zones for each of the various end-effectors 240A, 240B, 240C.

The alert setup interface 151 may also include one or more alert buttons 156A, 156B, 156C, 156D. The alert buttons 152A, 152B, 156C, 156D may be utilized to manipulate the various alerts described above. For example, a first alert button 156A may be configured to allow the user to activate or deactivate an alert related to the rotational speed of the end-effector 240, 340, 440. For example, as described above, the navigation processor 140 and/or the instrument processor 215, 315, 415 may be configured to manipulate the rotational speed (RPM's) of the end-effector 240, 340, 440 based on the position of the end-effector 240, 340, 440 relative to one or more the virtual boundaries and/or alert zones.

A second alert button 156B may be configured to allow the user to activate or deactivate a tactile alert. For example, the user may manipulate the second alert button 156B to activate one of tactile alerts described above. This may include the navigation processor 140 being configured to send a signal to the surgical instrument assembly 200, 300, 400 to activate the alert device 255, 355, 455 configured to provide a tactile alert to the surgeon based on the position of the end-effector 240, 340, 440 relative to one or more the virtual boundaries and/or alert zones.

A third alert button 156C may be configured to allow the user to activate or deactivate a visual alert. For example, the user may manipulate the third alert button 156C to activate one of the visual alert. This may include the navigation processor 140 being configured to send a signal to the surgical instrument assembly 200, 300, 400 to activate the alert device 255, 355, 455 configured to provide a visual alert to the surgeon based on the position of the end-effector 240, 340, 440 relative to one or more the virtual boundaries and/or alert zones.

A fourth alert buttons 156D may be configured to allow the user to activate or deactivate one of the audible alerts described above. For example, the user may manipulate the fourth alert button 156D to activate the audible alert, such that the navigation processor 140 may send a signal to the surgical instrument assembly 200, 300, 400 to activate the alert device 255, 355, 455 configured to provide an audible alert to the surgeon based on the position of the end-effector 240, 340, 440 relative to one or more the virtual boundaries and/or alert zones.

The alert setup interface 151 of the graphical user interface (GUI) 150A may also one or more alert graphics 158A, 158. The alert graphic(s) 154A, 154B may be specific to the particular surgical instrument and/or end-effector and may be configured to provide a schematic and/or visual representation of the location of the various virtual boundaries and/or alert zones. The first alert graphic 158A may include a visual representation of the surgical region and any implants or devices to be inserted during the medical procedure to assist the surgeon in identifying the location of the procedure and with setting the various alerts. For example, as illustrated in FIG. 8, the first alert graphic includes a visual of the vertebral body with the region where the procedure will take place outlined in dotted lines. The first alert graphic may also include a visual of the pedicel screw to be inserted during the procedure.

The second alert graphic 158B may be configured to provide a visual representation of the implant or device to be inserted during the procedure along with markers indicating the various virtual boundaries (Boundary 5, 6, 7) relative to the implant or device to assist the surgeon in adjusting or modifying the location where the alerts assigned to each of the various virtual boundaries and/or alert zones should be triggered. For example, as illustrated in FIG. 8, the second alert graphic 158B includes a visual representation of the pedicle screw to be inserted and markers along the pedicle screw indicating the location of the various virtual boundaries (Boundary 1, 2, 3) relative to the pedicle screw that will trigger the various alerts during the procedure.

The alert setup interface 151 of the graphical user interface (GUI) 150A may also comprise a virtual boundary setup interface 160A, 160B. The boundary setup interface 160A, 160B may comprise one more prompts or buttons 162A, 162B, 162C, 162D, 162E for setting and/or manipulating when the virtual boundary will trigger one or more of the various alerts described above. A first boundary setup interface 160A may comprise a first button 162A may be configured to identify the implant(s) and/or device(s) to be inserted during the procedure. This allows the navigation system 100 to determine which and how many virtual boundaries and/or alert zones to provide. For example, if the surgeon manipulates the first button 162A to indicate a Laminotomy will be performed, the navigation system 100 will understand that this is a resection process and the navigation system 100 will know identify and provide the various alert zones around the critical structures of the verbal to assist the surgeon in executing the procedure. Attentively, if the surgeon manipulates the first button 162A to indicate a pedicle screw procedure will be executed, the navigation system 100 will know identify and provide the various virtual boundaries needed to assist the surgeon, in drilling, tapping, and placing the pedicle screw.

A second button 162B of the boundary setup interface 160A may be configured to comprise a depth button 162B. The depth button 162B may be configured to allow the surgeon to select the depth of the alert zone for a resection procedure, such as a Laminotomy. For example, the first boundary setup interface 160A illustrated in FIG. 8 indicates that the surgeon is setting alerts for a Laminotomy based on the manipulation of the first button 162A. Based on this selection by the surgeon, the second button 162B provides a manipulatable button configured to allow the surgeon to select the depth of the alert zone to be utilized by the navigation system 100 to trigger one or more of the various alerts.

The alert setup interface 151 may be configured such that the alert graphic 158A adjacent the boundary setup interface 160A may be manipulated or altered based on the manipulation of the buttons 12A, 162B of the boundary setup interface 160A.

A second boundary setup interface 160B of the alert setup interface 151 may comprise additional buttons button 162C, 162D, 162E related to the configuration of the various virtual boundaries and/or alert zones for triggering the alerts during the medical procedure. For example, as illustrated in FIG. 8, the second boundary setup interface 160B may be configured to provide buttons 162C, 162D, 162E for manipulating the setting of the alerts for the procedure of inserting a pedicle screw. A third button 162C of the second boundary setup interface 160B may be configured to set distance or depth for a reference location to position the virtual boundary, such as Boundary 5, along the target trajectory. For example, as indicated in FIG. 8, the third button 162C includes a toggle to allow the surgeon to set the depth for inserting the first end-effector, i.e. a drill, before the alert is triggered. In the example, the user has set the third button 162C to 30 mm, indicating the navigation system 100 should trigger the alert for the first end-effector when it has travel a distance of or reached a depth of 30 mm. The second boundary setup interface 160B may include additional button 162D, 162E for manipulation and/or adjustment of when the alerts should be triggered for the second end-effector, i.e. the tap, and/or the third end-effector, i.e. the driver for inserting the screw. As described above, the navigation system 100 may be configured such that the fourth and fifth buttons 162D, 162E for manipulating the alerts for the second and third end-effectors may manipulate the location of the virtual boundary for triggering the alert based on the virtual boundary for triggering the alert for the first end-effector. For example, as indicated by the fourth button 162D, the virtual boundary for triggering the alert for the second end effector, i.e. the tap, should be shifted zero millimeters (0-mm) relative to the virtual boundary for triggering the alert for the first end-effector. However, the fourth button 162D may be manipulated to shift the boundary for triggering the alert for the second end effector as needed. Similarly the fifth button 162E may be manipulated to modify or adjust the virtual boundary for triggering the alert for the third end-effector.

The alert setup interface 151 of the graphical user interface (GUI) 150A may also comprise an alert test button 164A, 164B. The alert test button 164A, 164B may be configured to test and/or confirm the selected alerts are active and working properly. For example, in operation, after the surgeon has selected and/or entered all of the various information related to the medical procedure into alert setup interface 151, the surgeon may select the alert test button 164A, 164B to confirm the selected alerts are active. For example, if the surgeon selected the first alert button 156A directed to the motor speed alert to be active, the surgeon my activate the surgical instrument 220, 320, 420 and press the alert test button 164A, 164B. Pressing the alert test button 164A, 164B instructs the navigation system to send a test signal to the instrument processor 215, 315, 415 activate the alert associated with the first alert button 156A, such as reducing the speed of the motor and by extension the speed of ration of the end-effector 240, 340, 440. Upon user selecting the alert test button 164A, 164B, each of the various alerts that have been activated based on the manipulation of an alert button 156A, 156B, 156C, 156D, 156E should be triggered. Any activated alerts that are not triggered upon selection of the alert test button 164A, 164B should be further evaluated by the surgeon to confirm they are in fact working properly prior to beginning the medical procedure.

Figure 9:
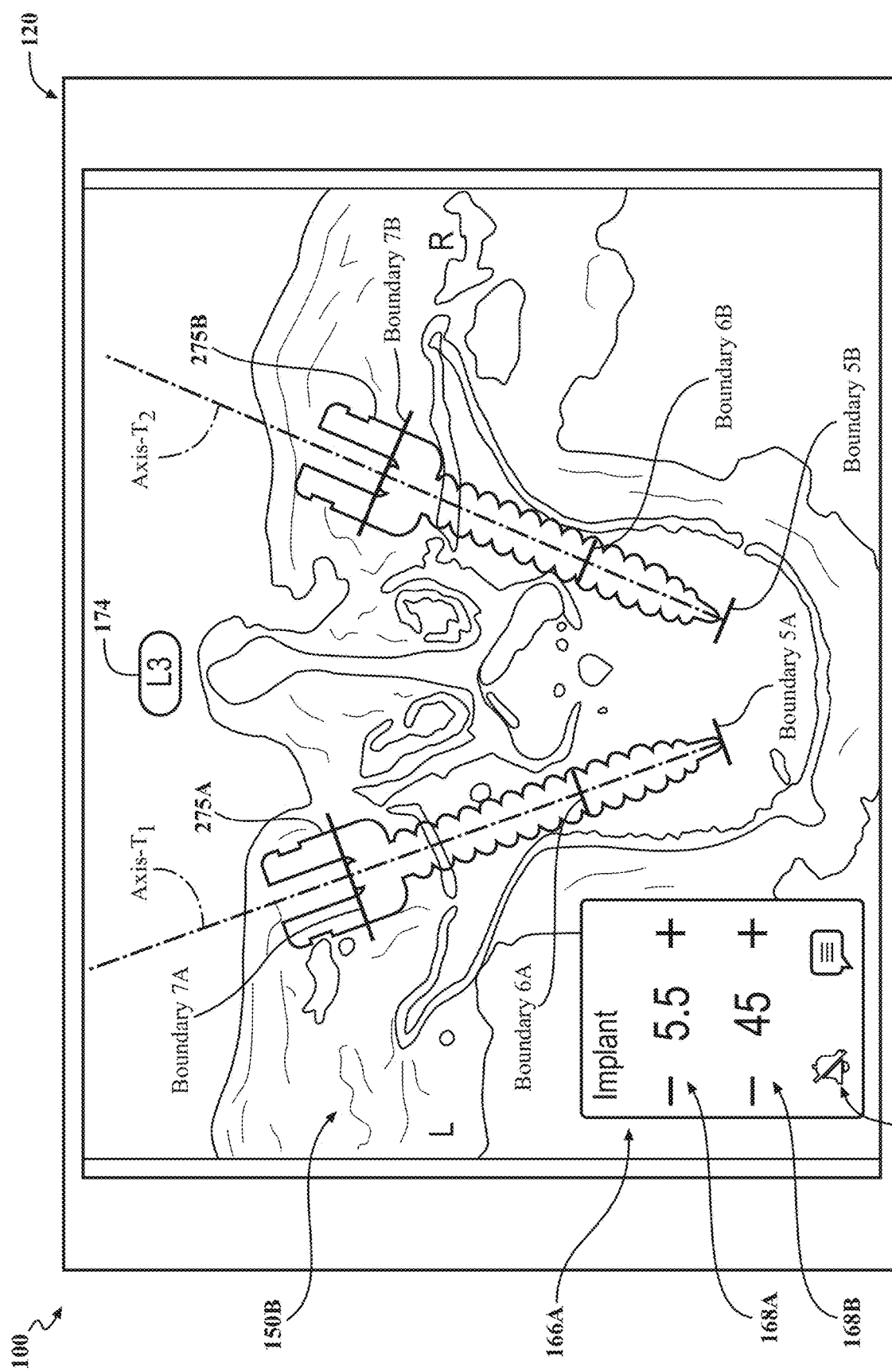
FIG. 9 is a schematic of an exemplary graphical user interface (GUI) of a navigation system, the graphical user interface displaying an image of the planned placement of a surgical implant and user-selectable objects related to the depth of the implant.

Referring to FIG. 9, an exemplary graphical user interface (GUI) 150B as shown on the display 120 of the navigation system 100 is illustrated. The graphical user interface (GUI) 150B may be configured to includes a visual representation of the surgical plan, including a planned pose of the implant 275A, 275B within the known coordinate system. The implant 275A, 275B may define the target axis Axis-$T_1$, Axis-$T_2$. The navigation system 100 may provide one or more virtual boundaries (Boundary 5, 6, 7), as described above, along the target axis Axis-$T_1$, Axis-$T_2$ representing target depths for each of the various end-effectors 240A, 240B, 240C utilized in execution of the procedure. For example, as illustrated in FIG. 9, a first boundary (Boundary 5A, 5B) is shown along the target axis Axis-$T_1$, Axis-$T_2$ for each of the implants 275A, 275B. The navigation system 140 may be configured to define the first boundary (Boundary 5A, 5B) based on the target depth for the tip of a first end-effector 240A, such as a drill for boring the hole for placement of a screw 275A, 275B. The navigation system 100 may be further configured to define the second boundary (Boundary 6A, 6B) based on the target depth for a second end-effector 240C, such as a tap for cutting threads in the hole. It is contemplated that the navigation system 100 may define the second boundary (Boundary 6A, 6B) relative to the first boundary (Boundary 5A, 5B) based, at least in part, on the selected implant 275A, 275B and its pose. For example, the navigation system 100 may define the first boundary (Boundary 5A, 5B) within a known coordinate system of the patient along the target axis Axis-$T_1$, Axis-$T_2$. Then based on the selected implant 275A, 275B, the navigation system 100 may be configured to define the second boundary (Boundary 6A, 6B) at distance from the first boundary (Boundary 5A, 5B) based on the selected implant 275A, 275B. The navigation system 140 may be further configured to define the third boundary (Boundary 7A, 7B) based on the target depth for a third end-effector 240C, such as a driver for placing the screw 275A, 275B in the hole. It is contemplated that the navigation system 100 may define the third boundary (Boundary 7A, 7B) relative to the first boundary (Boundary 5A, 5B) based, at least in part, on the selected implant 275A, 275B and its pose. For example, the navigation system 100 may define the first boundary (Boundary 5A, 5B) within a known coordinate system of the patient along the target axis Axis-$T_1$, Axis-$T_2$. Then based on the selected implant 275A, 275B, the navigation system may be configured to define the third boundary (Boundary 7A, 7B) at distance from the first boundary (Boundary 5A, 5B) based on the selected implant 275A, 275B. For example, the navigation system may be configured that based on the depth of the first boundary (Boundary 1A, 1B) and the known length of the selected implant 275A, 275B, the navigation system can determine that the third boundary (Boundary 7A, 7B) should be spaced thirty millimeters (30 mm) along the target axis Axis-$T_1$, Axis-$T_2$ from the first boundary (Boundary 5A, 5B). While only the first boundary (Boundary 5A, 5B), the second boundary (Boundary 6A, 6B), and the third boundary (Boundary 7A, 7B) are illustrated in FIG. 9, additional virtual boundaries are contemplated. The navigation system 140 may be configured define and assign a virtual boundary to each of the end-effectors 240A, 240B, 240C. The location of these virtual boundaries and or when they are configured to trigger one of the various alerts described above may be manipulated and/or adjusted in the manner described with regard to FIG. 8 with the alert setup interface 151.

The exemplary graphical user interface (GUI) 150B of FIG. 9 may also comprise a planning interface 166A including a plurality of planning buttons 168A, 168B manipulatable by the surgeon to modify or adapt the placement of the implant 275A, 275B. For example, planning interface 166A may comprises a diameter button manipulatable by the surgeon to modify the diameter of the planned screw. The planning interface 166A may also comprises a length button manipulatable by the surgeon to modify the length of the planned screw 275A, 275B. The planning interface 166A may also allow a user to reposition the planned screw 275A, 275B by changing its position and/or orientation relative to the patient model.

The planning interface 166A of the graphical user interface (GUI) 150B of FIG. 9 may also comprise an alert button 170. As described above, the alert button 170 may be configured to activate, modify, and/or disable one or more the various alerts described above. The graphical user interface (GUI) 150B may be configured such that selection of the alert button 170 by the surgeon may open a boundary setup interface 160C similar to the one described in FIG. 8. The boundary setup interface 160C may include additional buttons and/or prompts that are manipulatable by the surgeon to modify or adjust the virtual boundaries and/or alert zones configured to trigger one or more of the alerts.

Figure 10:
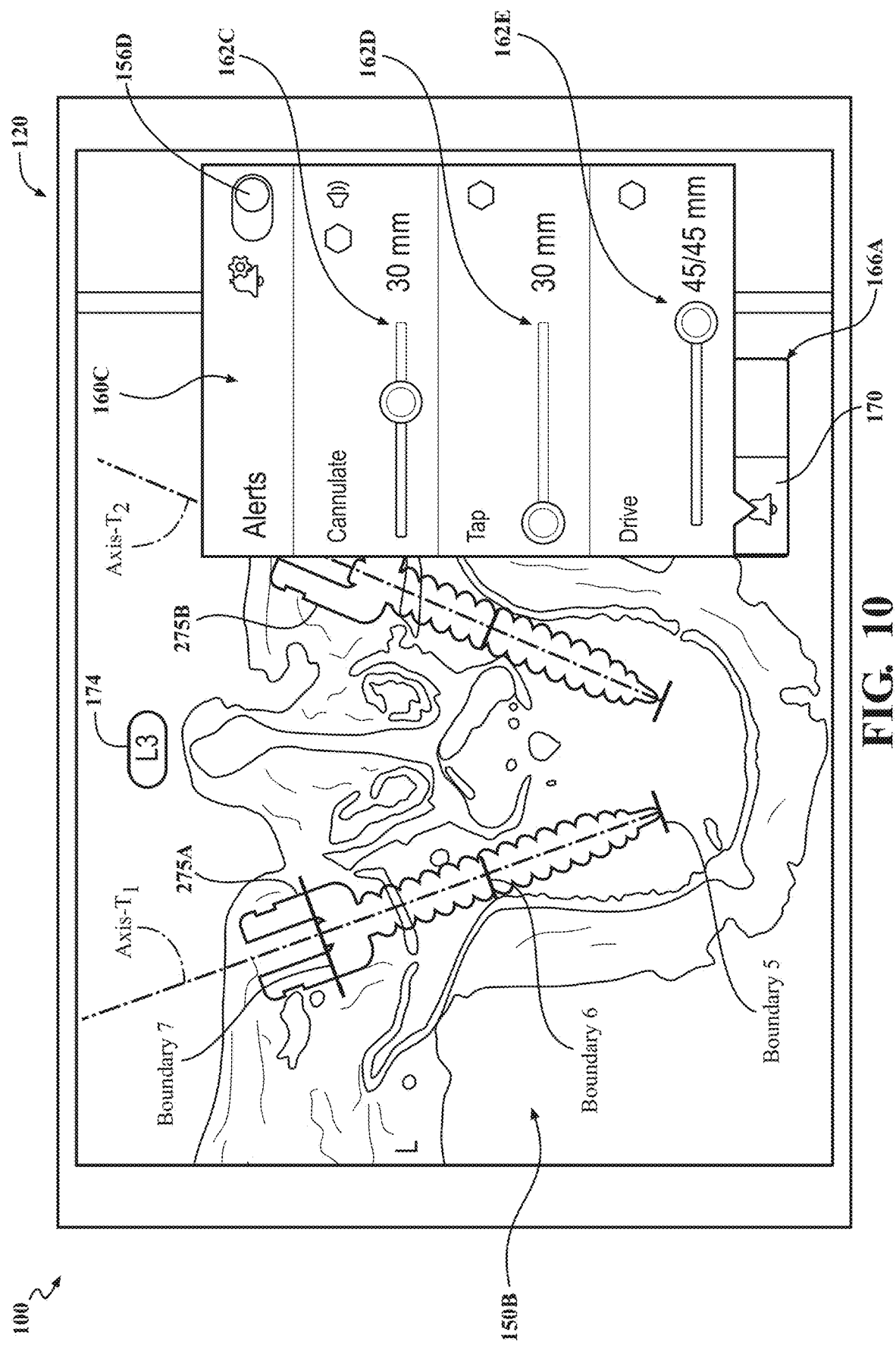
FIG. 10 is a schematic view of an exemplary graphical user interface (GUI) of a navigation system, the graphical user interface displaying an image of the planned placement of a surgical implant and user-selectable objects related to the settings for each of the various surgical instruments to be used in executing the surgical procedure.

Referring to FIG. 10, an exemplary boundary setup interface 160C that may be viewed by the surgeon upon selection of the alert button 170 is illustrated. For example, the user selecting the alert button 170 of the planning interface 166A from the graphical user interface (GUI) 150B from FIG. 9 may cause the graphical user interface (GUI) 150B to open the boundary setup interface 160C for viewing on the navigation display 120. The boundary setup interface 160C may comprise an alert button 156D configured to allow the surgeon to activate or deactivate the various alerts. The boundary setup interface 160C may also comprise one or more buttons 162C, 162D, 162E, similar to those described for boundary setup interface 160A, 160B of FIG. 8 described above. For example, the boundary setup interface 160C may comprise three boundary manipulation buttons 162C, 162D, 162E, one for each of the various end-effectors 240A, 240B, 240C. As described above, manipulation of the buttons 162C, 162D, 162E may modify or manipulate when the alert is triggered for each of the various end-effectors 240A, 240B, 240C. This allows the surgeon to create a custom surgical plan by modifying the navigation system 100. Based on the value input by the surgeon using the buttons 162C, 162D, 162E, the location of the various virtual boundaries will be updated within the surgical plan utilized to navigate system for triggering the alert(s) based on the position of the various end-effectors 240A, 240B, 240C relative to one or more virtual boundaries during the procedure.

The graphical user interface (GUI) 150B may even comprise a level label 174 that is displayed on the display 120 of the navigation system 100. The level label 174 may be configured to identify the anatomical feature or critical structure. For example, as illustrated in FIGS. 9 and 10, the level label 174 is configured to identify the third lumbar spine vertebra (L3). The level label 174 could be utilized to identify any number of anatomical structures and/or regions of the patient. Alternatively, the level label 174 could be utilized to identify a particular pose, orientation, or view of the anatomical structure that is being displayed. The level label 174 may be automatically assigned by the navigation system based on the patient data. Alternatively, the level label 174 may be selectable by the surgeon from a populated list. For example, the patient data may include an image or representation of the patient spine, and the surgeon may select the level label 174 assigned to each of the vertebrae. In yet another configuration, the navigation system 100 may be configured to allow the surgeon to enter the level label 174 using the user input device 130 or the graphical user interface (GUI) 150.

Figure 11A:
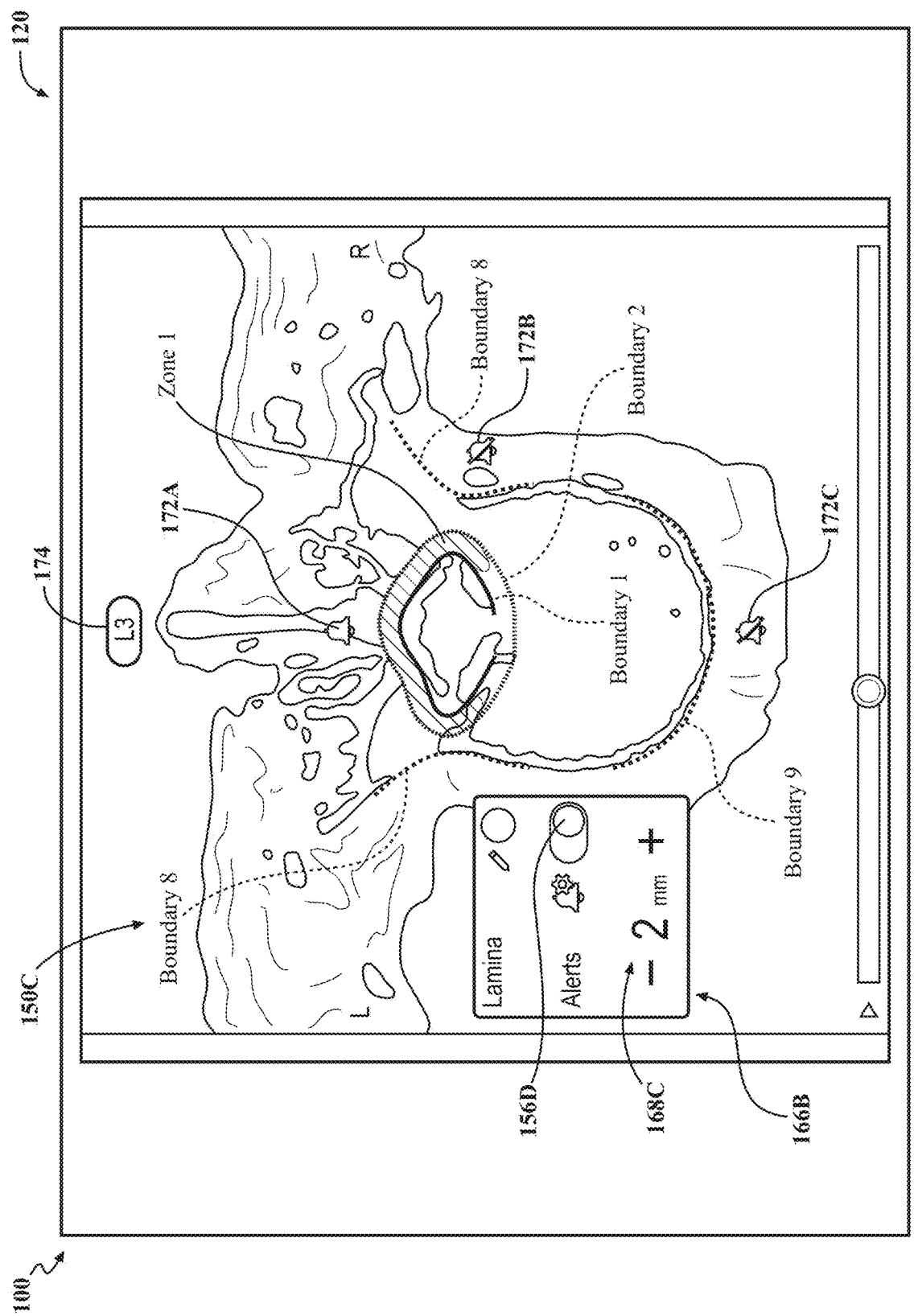
FIG. 11A is a schematic view of an exemplary graphical user interface (GUI) of a navigation system, the graphical user interface displaying user-selectable objects related to a volume defining an alert zone.
Figure 11B:
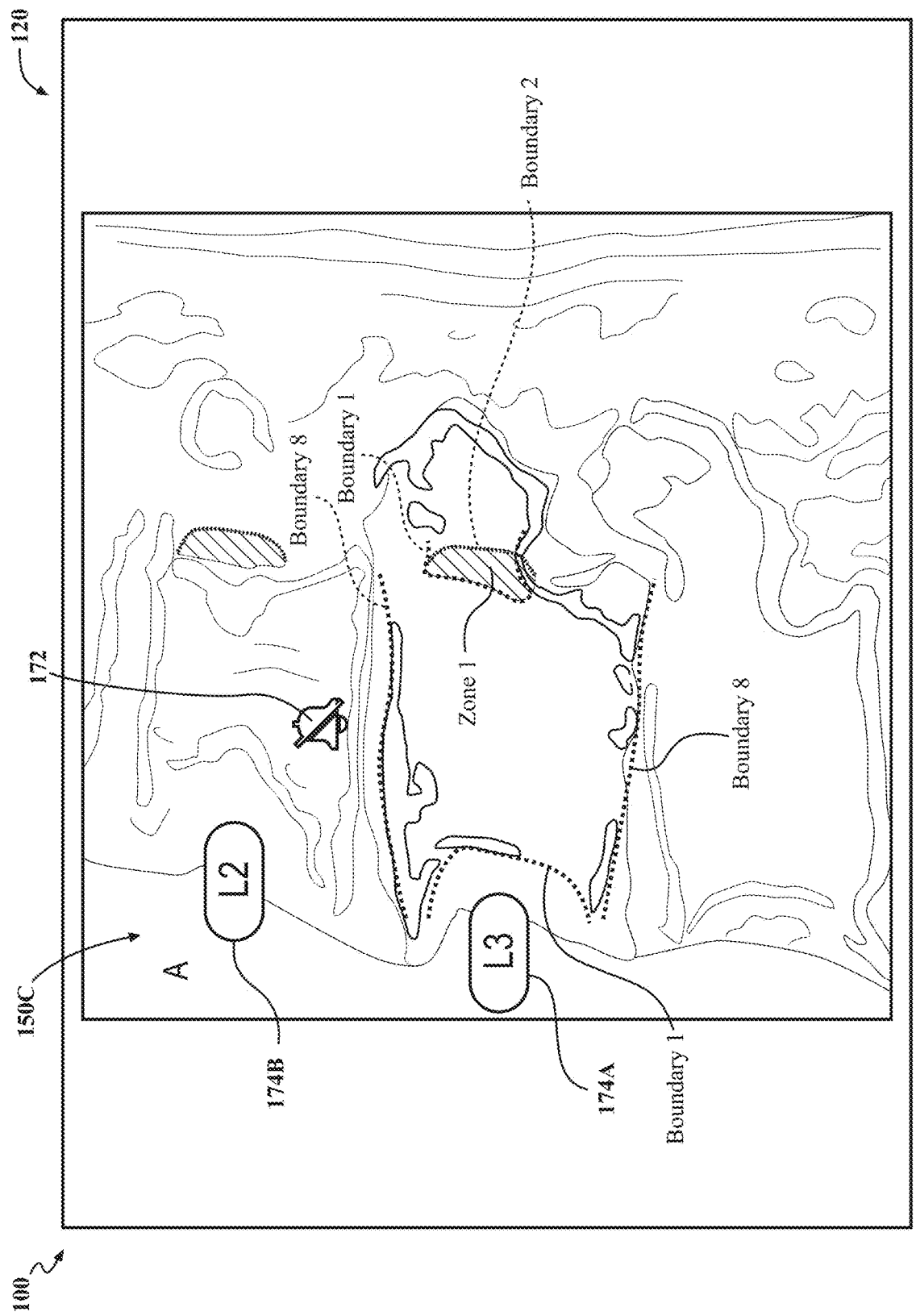
FIG. 11B is a schematic view of the exemplary graphical user interface (GUI) of FIG. 11A illustrating the volume defining the alert zones from a different perspective.
Figure 11C:
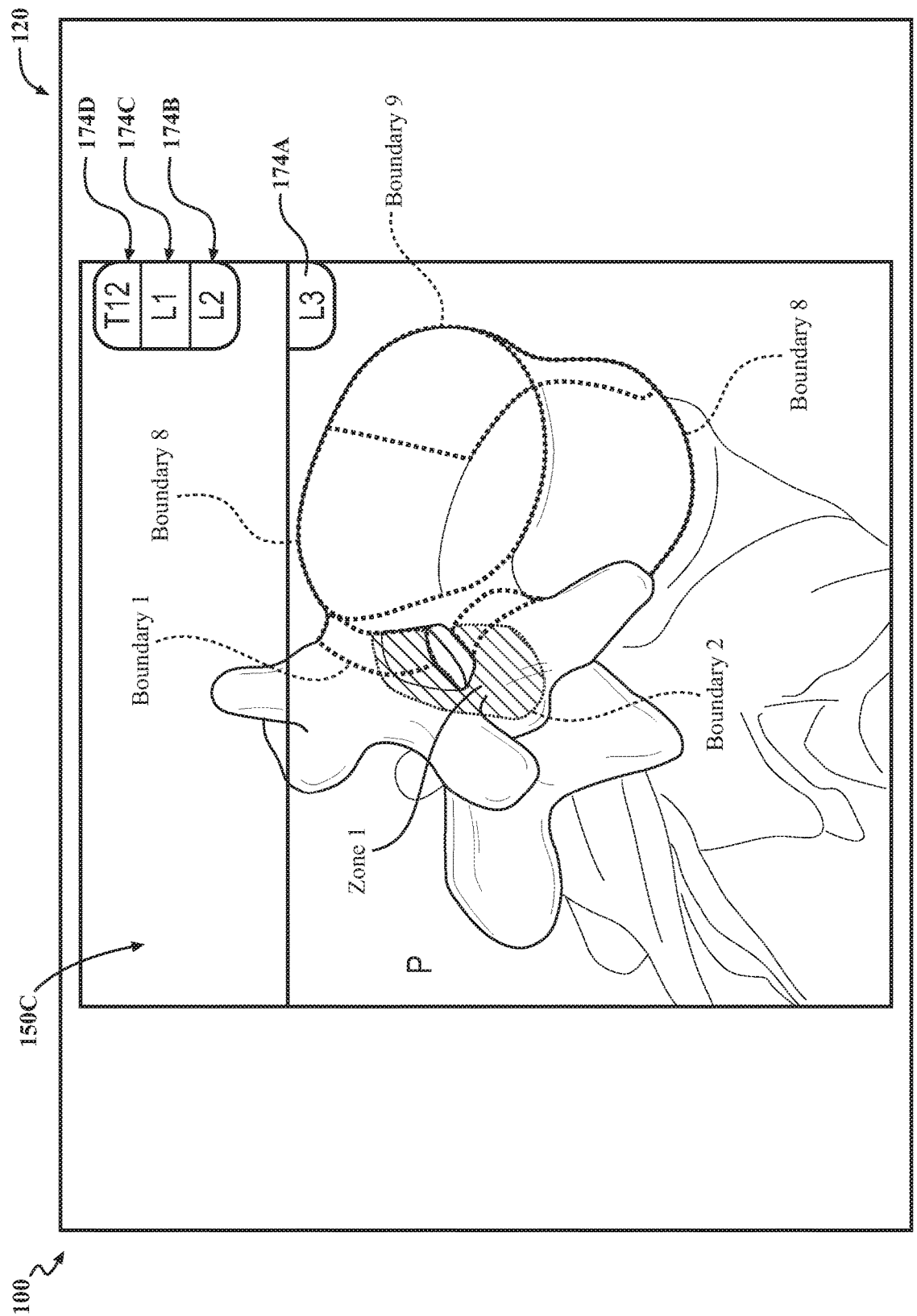
FIG. 11C is a schematic view of the exemplary graphical user interface (GUI) of FIG. 11A illustrating the volume defining the alert zones from a different perspective.

Referring to FIGS. 11A to 11C, an alternative exemplary graphical user interface (GUI) 150C as shown on the display 120 of the navigation system 100 is illustrated. The graphical user interface (GUI) 150C may be configured to display multiple views of the anatomical feature including the various virtual boundaries (Boundary 1, 2, 89) and/or alert zones (Zone 1) shown in the known coordinate system relative to the anatomical feature for resection procedure. Referring to FIG. 11A, a superior view of the vertebra is displayed in the graphical user interface (GUI) 150C, including the location of the various virtual boundaries (Boundary 1, 2, 8, 9) and/or the alert zones (Zone 1) relative to critical anatomical structures. Similar to the graphical user interfaces (GUI) 150 described above, the graphical user interface (GUI) 150C illustrated in FIG. 11A includes a planning interface 166B including one or more buttons, such as an alert button 156D configured to activate and/or deactivate one or more of the various alerts. The planning interface 166B may also comprise a planning buttons 168C configured to allow the surgeon to manipulate the various alerts and/or various virtual boundaries (Boundary 1, 2, 8, 9) configured to trigger one or more the various alerts. For example, The planning buttons 168C of the planning interface 166B may be configured to allow the user to increase or decrease the depth of one or more of the various alert zones by manipulating the distance between one or more of the virtual boundaries (Boundary 1, 2) that define at least a portion of the alert zone (Zone 1).

The graphical user interface (GUI) 150C may also comprise alert indicators 172 positioned within the display of anatomical feature relative to the various virtual boundaries (Boundary 1, 2, 8, 9) and/or the alert zone (Zone 1). The alert indicators 172 may be positioned proximate a specific virtual boundaries (Boundary 1, 2, 8, 9) and/or the alert zone (Zone 1) and be configured to identify to the surgeon whether the alert assigned to the (Boundary 1, 2, 8, 9) and/or the alert zone (Zone 1) proximate the alert button is activated, deactivated, and/or snoozed. For example, the alert indicators 172 proximate the fourth boundary, Boundary 4, shows a bell with a line through it. The navigation system 140 may be configured such that this symbol indicates the alert for the fourth boundary, Boundary 4, is deactivated. Alternatively, the alert indicators 172 proximate the first and second boundary (Boundary 1, 2) shows a bell without a line through it. The navigation system 140 may be configured such that alert indicators 172 indicates the alert for the first and second boundaries, Boundary 1,2, are activated. The alert indicators 172 may also selectable and/or manipulatable by the surgeon to activate or deactivate the alert assigned to the specific virtual boundaries (Boundary 1, 2, 8, 9) and/or the alert zone (Zone 1). For example, the alert indicators 172 proximate the fourth boundary, Boundary 4, may be configured such that manipulation of the alert indicators 172 by surgeon may cause the alert for the fourth boundary, Boundary 4, to be activated or deactivated.

Referring to FIG. 11B, a lateral view of the vertebra is displayed in the graphical user interface (GUI) 150C, including the location of the various virtual boundaries (Boundary 1, 2, 8, 9). While not shown in FIG. 11B, it is contemplated that the graphical user interfaces (GUI) 150 of FIG. 11B may also comprise a planning interface 166 including one or more buttons 168 configured to allow the surgeon to manipulate the various alerts and/or position of the various virtual boundaries (Boundary 1, 2, 8, 9) and/or the alert zone (Zone 1) that may be defined to trigger the various alerts. The graphical user interface (GUI) 150C may also comprise alert indicators 172 positioned within the display of anatomical feature relative to the various virtual boundaries (Boundary 1, 2, 8, 9) and/or the alert zone (Zone 1). The alert indicators 172 may be positioned proximate a specific virtual boundaries (Boundary 1, 2, 8, 9) and/or the alert zone (Zone 1) and be manipulatable by the surgeon to activate, deactivate, and/or snooze the alert assigned to the specific virtual boundaries (Boundary 1, 2, 8, 9) and/or the alert zone (Zone 1). For example, the alert button proximate the fourth boundary, Boundary 4, may be configured such that manipulation of the alert indicators 172 by surgeon may cause the alert for the fourth boundary, Boundary 4, to be activated or deactivated. As described above, the alert indicators 172 may also be configured to identify to the surgeon whether the alert assigned to the (Boundary 1, 2, 8, 9) and/or the alert zone (Zone 1) proximate the alert indicators 172 is activated or deactivated.

The graphical user interface (GUI) 150C may also comprise one or more labels 174A, 174B identifying the anatomical structure displayed on the graphical user interface (GUI) 150C. As illustrated in FIG. 11C, two labels 174A, 174B are shown on the graphical user interface (GUI) 150C, with a first label 174A identifying the primary anatomical structure and a second label 160B identifying an adjacent anatomical structure. The graphical user interface (GUI) 150C may be configured such that the user may manipulate the graphical user interface (GUI) 150C to navigate between the primary anatomical structure and an adjacent anatomical structure. For example, the surgeon may select the first label 174A identifying the anatomical structure proximate the first label 174A as the primary anatomical structure. The graphical user interface (GUI) 150C may be configured to display the primary anatomical structure in the center of the display 120. Alternatively, the surgeon may was to select the second label 174B, and the graphical user interface (GUI) 150C may be configured to identify the anatomical structure proximate the second label 174B as the primary anatomical structure, and position the anatomical structure proximate the second label 174B in the center of the display 120. While only two labels are shown in FIG. 11B, the graphical user interface (GUI) 150C may be configured to include any number of labels 174.

Referring to FIG. 11C, a perspective view of the vertebra is displayed in the graphical user interface (GUI) 150C, including the location of the various virtual boundaries (Boundary 1, 2, 8, 9) and/or the alert zone (Zone 1). While not shown in FIG. 11C, it is contemplated that the graphical user interfaces (GUI) 150 of FIG. 11C may also comprise a planning interface 166 including one or more buttons 168 configured to allow the surgeon to manipulate the various alerts and/or position of the various virtual boundaries (Boundary 1, 2, 8, 9) and/or the alert zone (Zone 1) that may be defined to trigger the various alerts. The graphical user interface (GUI) 150C may also comprise alert indicators 172 166 (not shown) positioned within the display of anatomical feature relative to the various virtual boundaries (Boundary 1, 2, 8, 9) and/or the alert zone (Zone 1). As described above, the graphical user interface (GUI) 150C may be configured to include any number of labels 174. FIG. 11C illustrates an exemplary configuration of the graphical user interface (GUI) 150C including a plurality of labels 174A, 174B, 174C. The graphical user interface (GUI) 150C may be configured to allow the surgeon to navigate between the various anatomical structures associated with each of the various labels 174A, 174B, 174C by selecting the label 174A, 174B, 174C of the anatomical structure the surgeons elects to view.

Figure 12A:
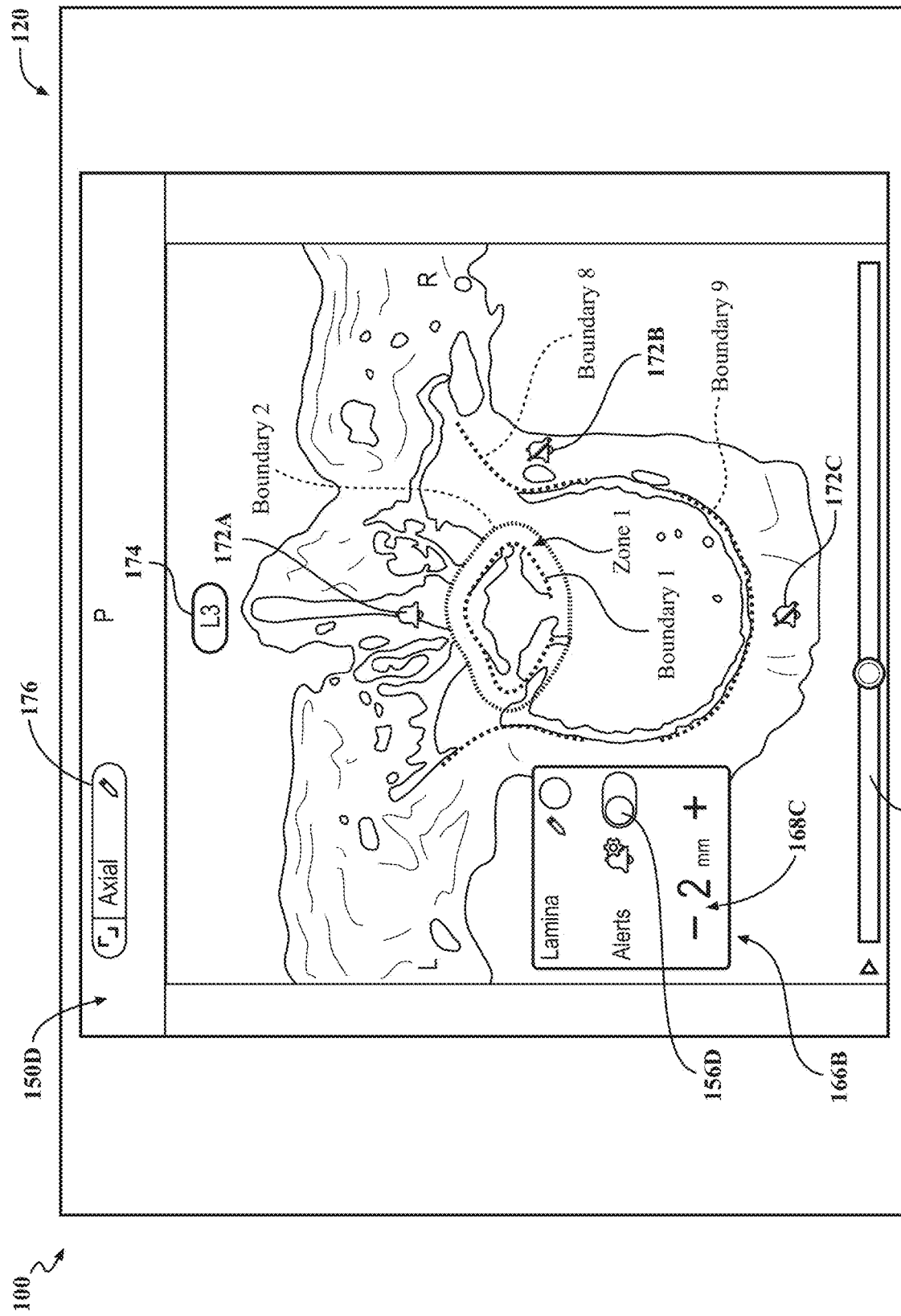
FIG. 12A is a schematic view of an exemplary graphical user interface (GUI) of a navigation system, the graphical user interface displaying user-selectable objects related to a boundary defining an alert zone.
Figure 12B:
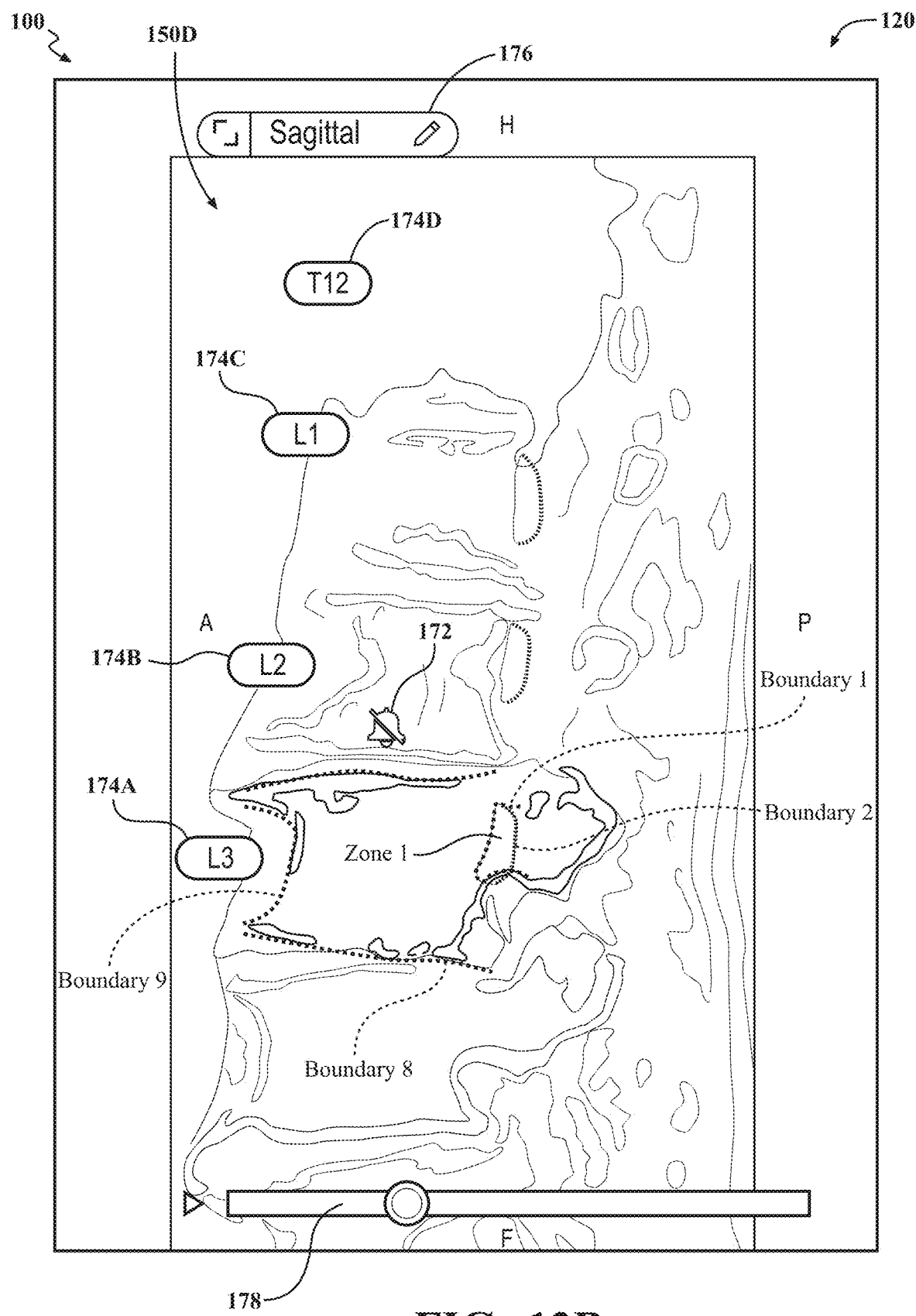
FIG. 12B is a schematic view of the exemplary graphical user interface (GUI) of FIG. 12A illustrating the boundary defining the alert zone from a different perspective.
Figure 12C:
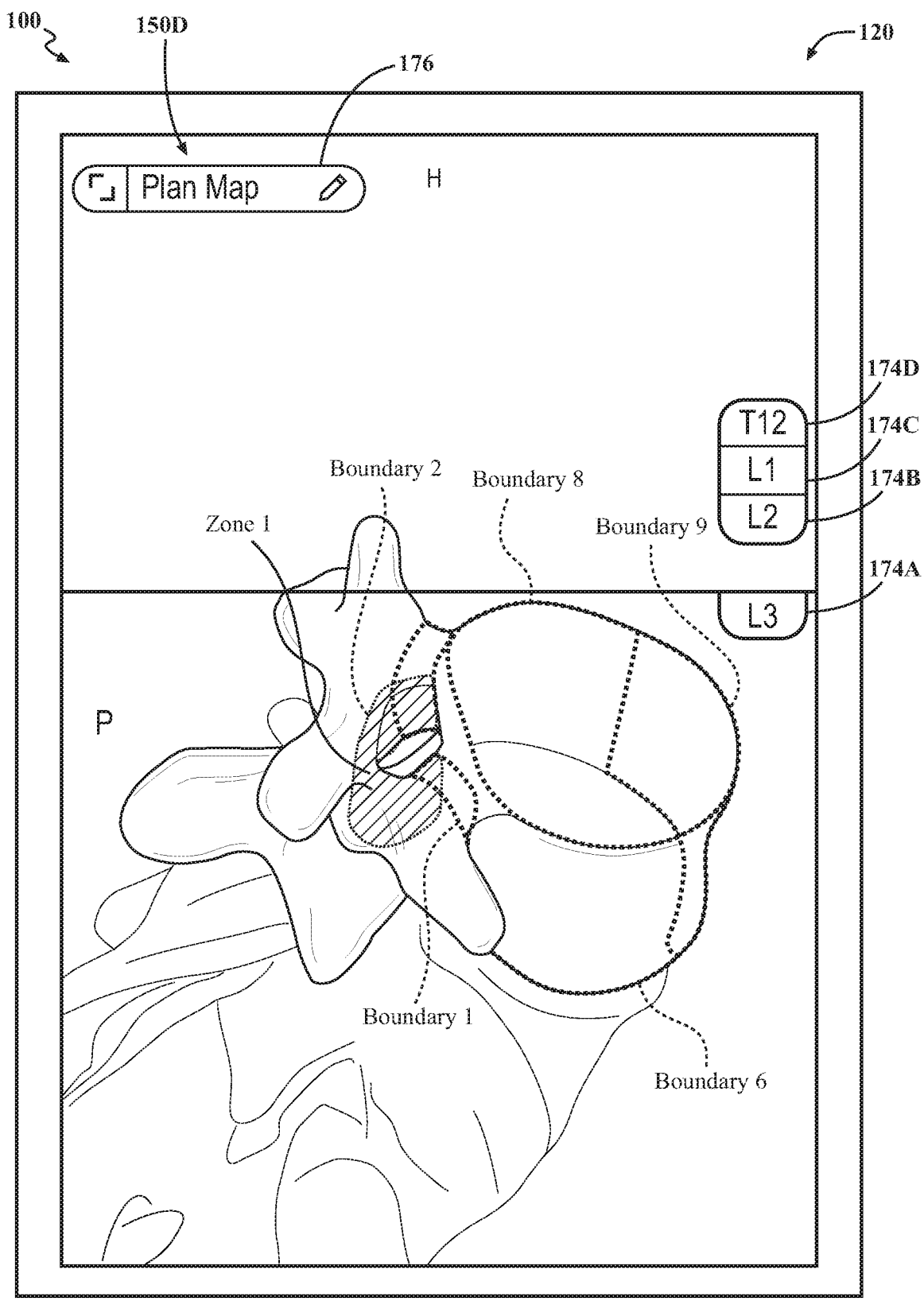
FIG. 12C is a schematic view of the exemplary graphical user interface (GUI) of FIG. 12A illustrating the boundary defining the alert zone from a different perspective.

Referring to FIGS. 12A to 12C, an alternative exemplary graphical user interface (GUI) 150D as shown on the display 120 of the navigation system 100 is illustrated. The graphical user interface (GUI) 150D may comprise any and/or all of the features, buttons and, or elements of the graphical user interface (GUI) 150C of FIGS. 11A to 11C described above. The graphical user interface (GUI) 150D may also function and/or operate in the same or similar to the graphical user interface (GUI) 150C of FIGS. 11A to 11C described above. The graphical user interface (GUI) 150D as illustrated in FIGS. 12A to 12C may further comprises a view button 176. The view button 176 may be manipulatable by the surgeon to switch and/or toggle between views of the anatomical feature including the various virtual boundaries (Boundary 1, 2, 8, 9) and/or alert zones (Zone 1). For example, in FIG. 12A, the view button 176 indicates the graphical user interface (GUI) 150D is displaying an axial view of the anatomical feature. Alternatively, the surgeon may use the view button 176 to have the graphical user interface (GUI) 150D display a different view of the anatomical feature and the related virtual boundaries (Boundary 1, 2, 8, 9) and/or alert zones (Zone 1). For example, referring to FIG. 12B, the view button 176 indicates the graphical user interface (GUI) 150D is displaying a sagittal view of the anatomical feature. Referring to FIG. 12C, the view button 176 indicates the graphical user interface (GUI) 150D is displaying a plan map view of the anatomical feature.

It is also contemplated that the graphical user interface (GUI) 150D may comprise a zoom button 178 configured to allow surgeon to manipulate the image on the display 120 of the navigation system 100 by zooming in and/or out. An exemplary configuration of a zoom button 178 of the graphical user interface (GUI) 150D is shown in FIGS. 12A and 12B. A zoom button 178 may be included in any of the graphical user interfaces (GUI) described herein.

Figure 13A:
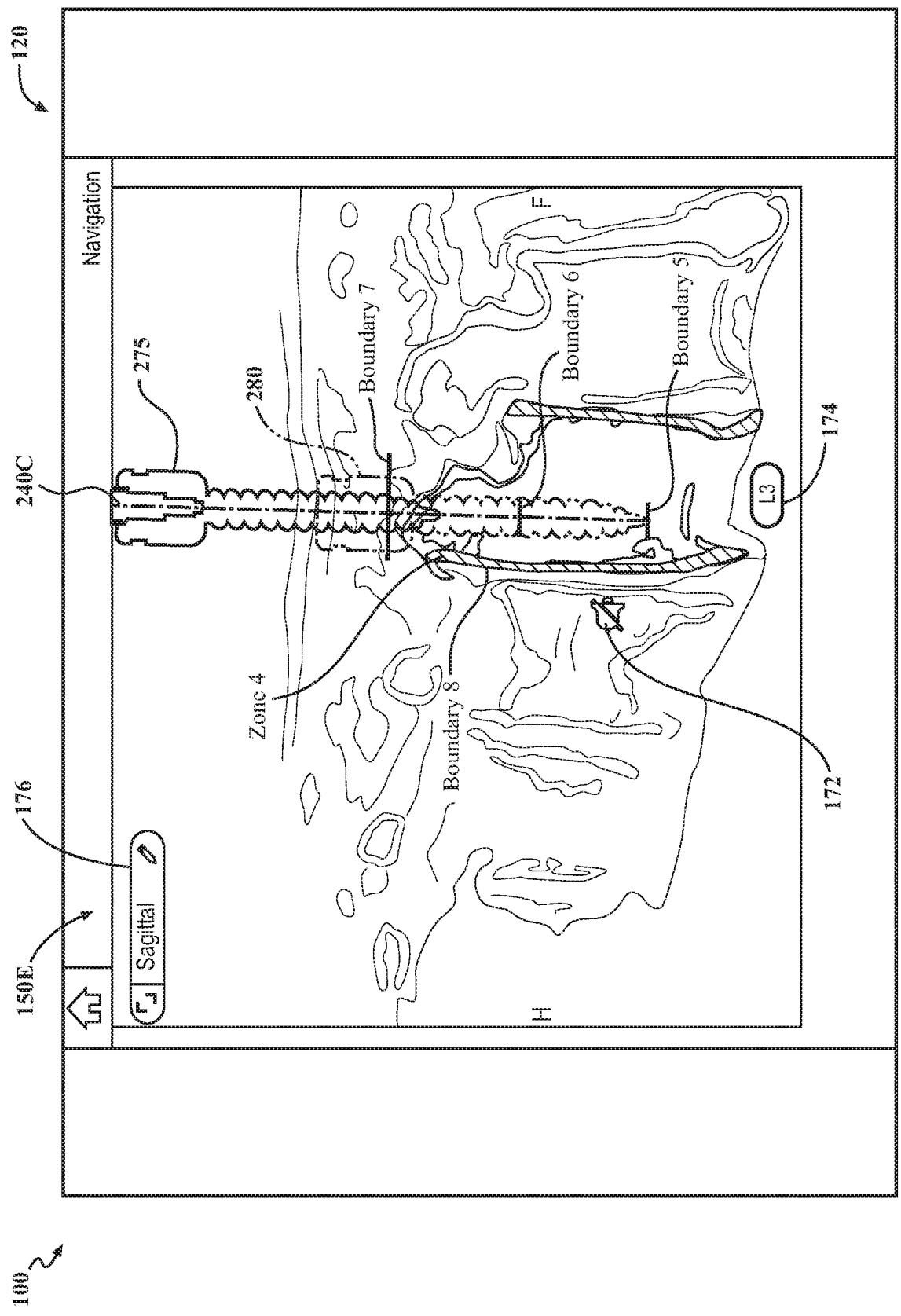
FIG. 13A is a schematic view of an exemplary graphical user interface (GUI) of a navigation system illustrating a sagittal view of the patient space during placement of a surgical implant.
Figure 13B:
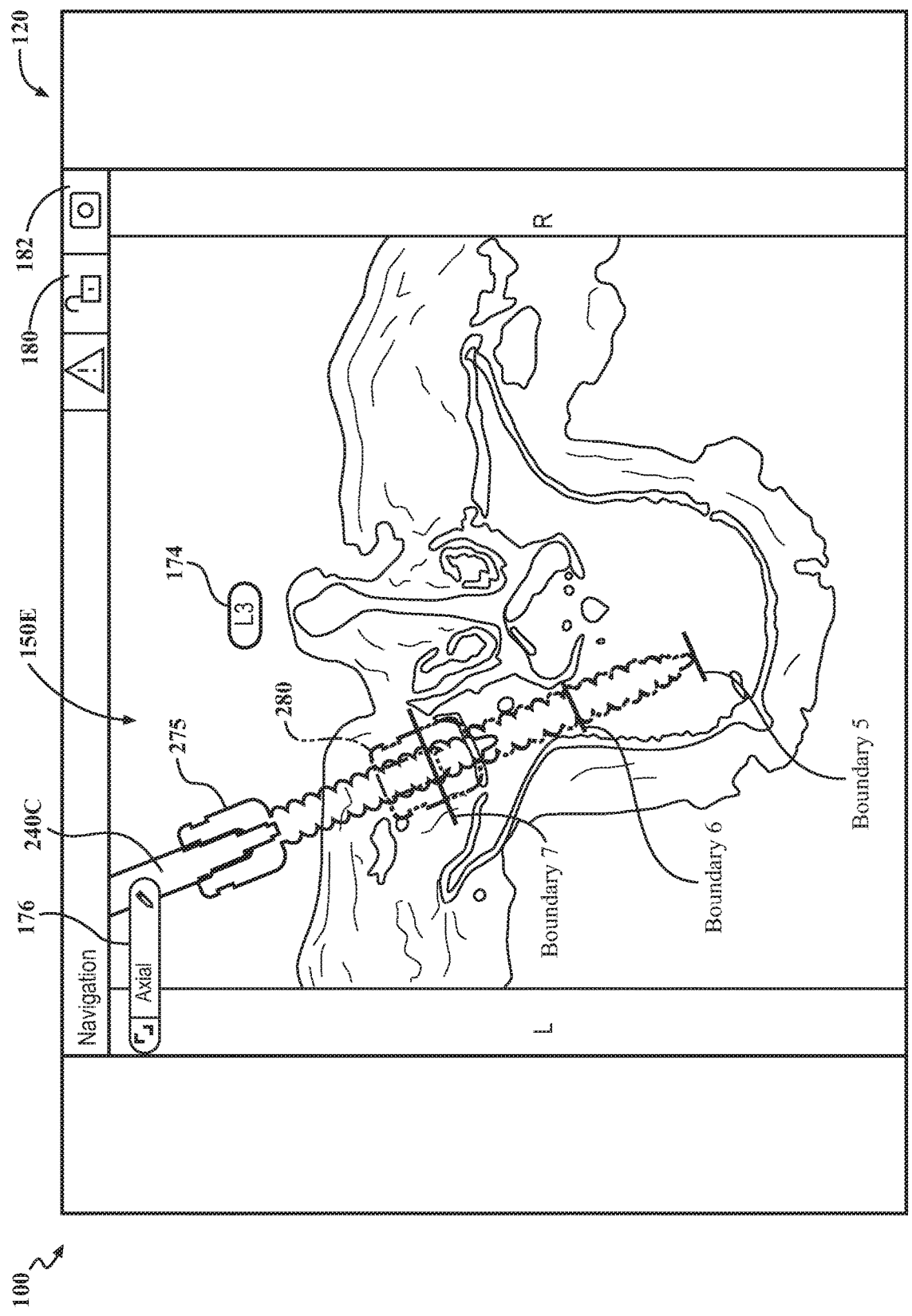
FIG. 13B is a schematic view of the exemplary graphical user interface (GUI) of FIG. 13A illustrating an axial view of the patient space during placement of a surgical implant.

Referring to FIGS. 13A and 13B, an exemplary graphical user interface (GUI) 150E as shown on the display 120 of the navigation system 100 during navigation of a surgical instrument 220, 320, 420 during placement of an implant 275 is illustrated. Similar to the graphical user interfaces (GUI) 150 described above, the graphical user interface (GUI) 150E includes a label 174 identifying the anatomical structure displayed on the graphical user interface (GUI) 150E. The graphical user interface (GUI) 150E also comprises a view button 176 configured to allow the surgeon to toggle between views. For example, the surgeon may use the view button 176 to have the graphical user interface (GUI) 150E display a sagittal view of the anatomical structure as is shown in FIG. 13A. Alternatively, the surgeon may use the view button 176 to have the graphical user interface (GUI) 150E display an axial view of the anatomical structure as is shown in FIG. 13B. While not illustrated in the figures, it is contemplated that the view button 176 may utilized to have the graphical user interface (GUI) 150E display additional views of the anatomical structure.

The graphical user interface (GUI) 150E may also be configured to display the virtual boundaries (Boundary 5, 6, 7, 8) and/or the alert zones defined using the navigation system 100. As is described above, the navigation system 100, during navigation of the surgical instrument 220, 320, 420, may be configured to send a signal or command to the instrument processor 215, 315, 415 to trigger one of the various alerts described above based on the position of the end-effector 240, 340, 440 relative to one of the virtual boundaries (Boundary 5, 6, 7, 8) and/or the alert zones. As illustrated in FIGS. 13A and 13B a number of virtual boundaries (Boundary 5, 6, 7, 8) and/or the alert zone (Zone 4) are illustrated with the known coordinate system based on the information selected and/or entered by the surgeon in the alert interface 151 described in FIG. 8. The virtual boundaries (Boundary 5, 6, 7, 8) and/or the alert zone (Zone 4) are configured to trigger an alert. As illustrated in FIGS. 13A and 13B, the virtual boundaries (Boundary 5, 6, 7) may correspond to a desired depth for insertion of an end-effector corresponding to each of the virtual boundaries (Boundary 5, 6, 7). The navigation system 100 may be configured to send the signal or command to the instrument processor 215, 315, 415 to trigger the alert based on the position of the end-effector 240, 340, 440 relative to the corresponding virtual boundary (Boundary 5, 6, 7) as part of assisting the surgeon in navigating the surgical instrument 220, 320, 420 to place the implant 275 or device.

The graphical user interface (GUI) 150E may also be configured to display to display the planned pose 280 of the implant 275 or device. For example, as illustrated in FIGS. 13A and 13B, graphical user interface (GUI) 150E may show and outline indicating the planned pose 280 of the implant within the known coordinate system to assist the surgeon in navigating the surgical instrument 220, 320, 420 to place the implant 275 or device. As can be seen in FIGS. 13A and 13B, the graphical user interface (GUI) 150E may show the end-effector 240C driving the implant 275 into place relative to the planned pose 280 and the virtual boundary (Boundary 5, 6, 7).

The graphical user interface (GUI) 150E may also comprise additional user interface buttons 180, 182. The user interface button 180 may be configured to lock or unlock the screen. For example, the surgeon may manipulate user interface button 180 to lock the screen preventing additional and/or unintentional touching of the graphical user interface (GUI) 150E from making changes. Alternatively, the user interface button 182 may be configured to take a screenshot and/or capture an image currently displayed on the graphical user interface (GUI) 150E. For example, the surgeon may manipulate user interface button 182 to capture an image displayed on the graphical user interface (GUI) 150E during navigation of the surgical instrument 220, 320, 420 during execution of the procedure. The user interface button 182 may also be configured to activate and/or deactivate video recording of the images displayed on the graphical user interface (GUI) 150E. For example, the surgeon may manipulate user interface button 182 to start and stop video recording of the images displayed on the graphical user interface (GUI) 150E during navigation of the surgical instrument 220, 320, 420 during execution of the procedure.

While not shown in the figures, during navigation of the surgical instrument 220, 320, 420, upon one of the various alerts being triggered based on the position of the end-effector 240, 340, 440 relative to one or more of the virtual boundaries and/or alert zones, the graphical user interface (GUI) 150 may be configured to provide or display a snooze button allowing the user to snooze and/or temporarily deactivate the alert that has been triggered. The graphical user interface (GUI) 150 may be configured such that manipulation of snooze button will temporarily disable one or more of the alerts as described above. For example, upon manipulation of the snooze button, the triggered alert may temporarily be deactivated for a defined period of time, such as two seconds. After the passage of the defined period of time the alerts may be reactivated and triggered if warranted based on the position of the end-effector 240, 340, 440 relative to one or more of the virtual boundaries and/or alert zones. As described above, it is also contemplated that manipulation of the snooze button may temporarily deactivate the triggered alert until the end-effector 240, 340, 440 has moved a defined distance farther relative to one or more of the virtual boundaries and/or alert zones. Upon the end-effector 240, 340, 440 moving the defined distance relative to one or more of the virtual boundaries and/or alert zones, the alerts may be reactivated. Depending on the direction movement of the handpiece 225, 325, 425 as determined by the navigation system 140, as well as position of the end-effector 240, 340, 440 relative to one or more of the virtual boundaries and/or alert zones, the alert may be triggered. The various scenarios to triggering, snoozing, and/or reactivating the various alerts are described in more detail above.

Below is an exemplary operation of said snooze function:

(Boundary 5, 6, 7) and/or alert zones, for example Zones 1, 2, 3, and 4, within pre-operative and/or intra-operative data of the patient 20 provided by an imaging system 500, as described above, or by other similar means of imaging the surgical site 30 of the patient 20. The method may further comprise identifying and/or registering the virtual boundary (Boundary 5, 6, 7) and/or alert zones (Zones 1, 2, 3, 4) to the patient. For example, this may be accomplished by using the user input 130 of the surgical navigation system 100 to identify and/or marking virtual boundary (Boundary 5, 6, 7) and/or the alert zones (Zones 1, 2, 3, 4) within the pre-operative and/or intra-operative data. Defining the virtual boundary (Boundary 5, 6, 7) and/or alert zones (Zones 1, 2, 3, 4) may include marking a border surrounding a critical anatomical structure, such as a nerve, that the surgeon wishes to avoid during execution of the medical procedure. It is also contemplated that various virtual boundary (Boundary 5, 6, 7) may be identified by the surgical navigation system using a segmentation algorithm and/or a boundary generator. The virtual boundary (Boundary 5, 6, 7) may be selectable and/or modified by the user. Multiple zones may be established, such as a first alert zone, Zone 1, to let the surgeon know they are approaching the critical anatomical structure. The first alert zone, Zone 1, may be at least partially defined by a first and second virtual boundary, Boundary 1, 2, wherein the first and second boundary are spaced apart a user selectable distance and/or depth with the volume defined between the first and second boundary representing the alert zone, zone 1. A second alert zone, Zone 2, may be defined within the first alert zone, Zone 1, where the second alert zone, Zone 2, is intended to let the surgeon know they are even closer to the critical anatomical structure. A third alert zone, Zone 3, may be defined within both the first alert zone, Zone 1, and the second alert zone, Zone 2, where the third alert zone, Zone 3, is the critical anatomical structure and is intended to let the surgeon know they are at the outer perimeter and about to breach the critical anatomical structure. A fourth alert zone, Zone 4, may be defined at the outer perimeter of the vertebra, opposite the surface of the vertebra where the end-effector 240, 340, 440 will initially enter the vertebra. Each of the various alerts zones may be at least partially defined as the area or volume defined between two or more virtual bound-

| Condition(?) # | | |
|---|---|---|
| 1 | IF | The end-effector is adjacent and/or distal to virtual boundary and/or within in an alert zone |
| 2 | OR | The end-effector has been adjacent and/or distal to and proximal to virtual boundary, or in and out of the alert zone for less than a defined period of time (For example: 5 Seconds) |
| 3 | AND | a manipulation of the trigger and/or footswitch between first and second positions is performed |
| 4 | Then | All alert devices are temporarily disabled |
| 5 | And | All alert devices remain disabled |
| 6 | Until | the end-effector has been proximal to virtual boundary and/or out of the alert zone for a defined period of time (For example: 7 Seconds) |
| 7 | Then | Alert devices are re-enabled and capable of being triggered once again |
| 8 | And | an audible "Alerts Enabled" tone sequence is sounded |
| 9 | True IF | Any alert devices have been re-enabled for the procedure, regardless of which alert devices |

Notes:
Enabled and Disabled alert devices may not be silenced -restricted volume range
Performing double tap of trigger or footswitch does affect operation of said surgicalinstrument unless conditions 1 or 2 above have been met Method of Navigating a Surgical Instrument:

A method of navigating a surgical instrument using a navigation system may comprise defining a virtual boundary ary's. The fourth alert zone, Zone 4, may notify the surgeon when the end-effector 240, 340, 440 is approaching the outer perimeter of the vertebra and in danger of potentially breaching the outer perimeter. This step may also include defining the planned surgical pathway, such as defining a target trajectory, Axis-T, and/or a target location T. The target trajectory, Axis T, may comprise the preferred trajectory and/or pose for aligning the surgical instrument 220, 320, 420 with in order to reach the target location T. The target trajectory, Axis T, may be established based on a combination of factors that may include, but is not limited to, avoiding critical anatomical structures, the type of medical procedure being performed, the type implant being inserted, as well as the desired placement and/or orientation of the implant. For example, the target axis, Axis T, may be established based on the preferred angle and/or location for inserting a pedicle screw to attach a support member to the spine.

The method may also comprise tracking the position of the surgical instrument 220, 320, 420 using the position and orientation of the instrument tracking device 230, 330, 430 relative to the patient 20 and/or the surgical site 30. This may be accomplished using the surgical navigation system 100. The instrument tracking device 230, 330, 430 of the surgical instrument 220, 320, 420 may be registered to the surgical navigation system 100. The surgical navigation system 100, using the tracking unit 110, may then track the position, orientation, and/or pose of the surgical instrument 220, 320, 420 during execution of the medical procedure.

The method may further comprise manipulating the speed of the variable speed motor 245, 345, 445 of the surgical instrument 220, 320, 420 between a maximum cutting speed and a minimum cutting speed based on the position of the surgical instrument 220, 320, 420 relative to the defined virtual boundaries (Boundary 4, 5, 6, 7) and/or alert zones, Zones 1, 2, 3. For example, the surgical navigation system 100 may be configured to communicate to the instrument processor 215, 315, 415 of the surgical instrument 220, 320, 420 that the surgical instrument 220, 320, 420 is adjacent and/or distal to the virtual boundaries (Boundary 1, 2, 3, 4, 5, 6, 7) and/or has entered the first alert zone, Zone 1, and instruct the instrument processor 215, 315, 415 to reduce the speed of the motor 245, 345, 445 from the maximum cutting speed to the minimum cutting speed in order to notify the surgeon that the surgical instrument 220, 320, 420 has entered the first alert zone, Zone 1. The surgical navigation system 100 may also be configured to communicate to the instrument processor 215, 315, 415 of the surgical instrument 220, 320, 420 that the end-effector 240, 340, 440 of the surgical instrument 220, 320, 420 is about to breach the third alert zone, Zone 3, and instruct the instrument processor 215, 315, 415 to reduce the speed of and/or disable the motor 245, 345, 445 to notify the surgeon that the surgical instrument 220, 320, 420 is about to breach the third alert zone, Zone 3, to prevent the surgical instrument 220, 320, 420 from contacting and/or damaging the critical anatomical structure. Decelerating the variable speed motor 245, 345, 445 from the maximum cutting speed to the minimum cutting speed when the surgical instrument 220, 320, 420 enters one of the alert zones (Zones 1, 2, 3) defined by the surgeon may generate an audibly perceptible change in the pitch produced by the variable speed motor 245, 345, 445 in order to notify the surgeon that the surgical instrument 220, 320, 420 is adjacent and/or distal to the virtual boundaries (Boundary 1, 2, 3, 4, 5, 6, 7) and/or has entered one of the alert zones (Zones 1, 2, 3) without compromising the ability of the surgical instrument 220, 320, 420 to continue to cut biological tissue. Maintaining a minimum cutting speed may prevent the end-effector 240, 340, 440 of the surgical instrument 220, 320, 420 from grabbing or biting and being thrown in an undesirable direction, possible damaging a critical anatomical structure within the patient 20.

The step of manipulating the speed of the variable speed motor 245, 345, 445 of the surgical instrument 220, 320, 420 between a maximum cutting speed and a minimum cutting speed based on the position of the surgical instrument 220, 320, 420 may also include manipulating the speed of the variable speed motor 245, 345, 445 of the surgical instrument 220, 320, 420 between a maximum cutting speed and a minimum cutting speed based on the position of the surgical instrument 220, 320, 420 relative to the defined target trajectory, Axis-T, and/or the target location T. For example, the surgical navigation system 100 may be configured to communicate to the instrument processor 215, 315, 415 of the surgical instrument 220, 320, 420 that the surgical instrument 220, 320, 420 is misaligned with the target trajectory, Axis-T, and instruct the instrument processor 215, 315, 415 to reduce the speed of the motor 245, 345, 445 from the maximum cutting speed to the minimum cutting speed in order to notify the surgeon that the surgical instrument 220, 320, 420 is misaligned. The surgical navigation system 100 may also be configured to communicate to the instrument processor 215, 315, 415 of the surgical instrument 220, 320, 420 that end-effector 240, 340, 440 of the surgical instrument 220, 320, 420 has reached the target location T and instruct the instrument processor 215, 315, 415 to reduce the speed of and/or disable the motor 245, 345, 415 in order to notify the surgeon that the surgical instrument 220, 320, 420 has reached the target location T.

The method may also comprise activating an alert device 255, 355, 455 to produce at least one of an audible, a haptic, or a visual notification based on the position of the surgical instrument 220, 320, 420 relative to the defined the virtual boundaries (Boundary 1, 2, 3, 4, 5, 6, 7) and/or alert zones (Zones 1, 2, 3). For example, the surgical navigation system 100 may be configured to communicate to the instrument processor 215, 315, 415 of the surgical instrument 220, 320, 420 that the surgical instrument 220, 320, 420 is adjacent and/or distal to the first virtual boundary (Boundary 1) and/or has entered the first alert zone, Zone 1, and instruct the instrument processor 215, 315, 415 to activate the alert device 255, 355, 455 to produce at least one of an audible, a haptic, or a visual notification to notify the surgeon that the surgical instrument 220, 320, 420 is adjacent and/or distal to the first virtual boundary (Boundary 1) and/or has entered the first alert zone, Zone 1. It is also contemplated that a combination of alert devices 255, 355, 455 and types of notifications may be utilized. For example, the surgical navigation system 100 may be configured to communicate to the instrument processor 215, 315, 415 of the surgical instrument 220, 320, 420 that the surgical instrument 220, 320, 420 is adjacent and/or distal to the first virtual boundary (Boundary 1) and/or has entered the first alert zone, Zone 1, and instruct the instrument processor 215, 315, 415 to activate the alert device 255, 355, 455 to produce an audible notification to notify the surgeon that the surgical instrument 220, 320, 420 is adjacent and/or distal to the first virtual boundary (Boundary 1) and/or has entered the first alert zone, Zone 1. The surgical navigation system 100 may then be configured to communicate to the instrument processor 215, 315, 415 of the surgical instrument 220, 320, 420 that the surgical instrument 220, 320, 420 is adjacent and/or distal to the second virtual boundary (Boundary 2) and/or has entered the second alert zone, Zone 2, and instruct the instrument processor 215, 315, 415 to activate the alert device 255, 355, 455 to produce a haptic notification to notify the surgeon that the surgical instrument 220, 320, 420 is adjacent and/or distal to the second virtual boundary (Boundary 2) and/or has entered the second alert zone, Zone 2. The surgical navigation system 100 may further be configured to communicate to the instrument processor 215, 315, 415 of surgical instrument 220, 320, 420 that end-effector 240, 340, 440 of the surgical instrument 220, 320, 420 is adjacent and/or distal to the third virtual boundary (Boundary 3) and/or is about to breach the third alert zone, Zone 3, and instruct the instrument processor 215, 315, 415 to reduce the speed of and/or disable the motor 245, 345, 445 to notify the surgeon that the surgical instrument 220, 320, 420 is adjacent and/or distal to the third virtual boundary (Boundary 3) and/or is about to breach the third alert zone, Zone 3, and to prevent the surgical instrument 220, 320, 420 from contacting and/or damaging the critical anatomical structure. This is only an exemplary configuration of the various combinations of alerts that may be produced by the surgical system 10 when performing a medical procedure. It is contemplated that any type and/or combination of alert(s) may be assigned to the various virtual boundaries (Boundary 1, 2, 3, 4, 5, 6, 7, 8, 9) and/or alert zones, target trajectory, and/or target location(s). The alerts are assignable by the surgeon at the time of defining the various alert zones, target trajectory, and/or target location(s) within the pre-operative and/or intra-operative data using the surgical navigation system 100.

An alternative method of navigating a surgical instrument 220, 320, 420 using a surgical navigation system 100 during a medical procedure on a patient may comprise a surgical instrument 220, 320, 420 including a handpiece 225, 325, 425, an end-effector 240, 340, 440 coupled to the handpiece 225, 325, 425. The surgical instrument 220, 320, 420 may comprise a variable speed motor 245, 345, 445 for selectively actuating the end-effector 240, 340, 440, and a processor 215, 315, 415 for controlling energization of said variable speed motor 245, 345, 445. The method may comprise selecting a medical implant 275, such as a pedicle screw. The method may also comprise identifying a location where the medical implant 275 is to be placed on the patient 20 within patient data stored on the surgical navigation system 100. For example, the medical professional may utilize the user input device 130, such a keyboard, touchscreen, or similar device, to select the location or portion of the patients 20, such as a vertebra, where the implant 275 is to be placed. The surgical navigation system 100 may then be configured to define various virtual boundaries (Boundary 1, 2, 3, 4, 5, 6, 7, 8, 9) based on the selected medical implant 275 and the identified location where the medical implant 275 is to be placed. Alternatively, it is also contemplated that the surgical navigation system 100 may be configured to identify the type of end-effector 240, 240, 440 coupled to the handpiece 225, 325, 425 of the surgical instrument 220, 320, 420 and define one more virtual boundaries (Boundary 1, 2, 3, 4, 5, 6, 7, 8, 9) based on the type end-effector 240, 340, 440, and/or the location of the procedure. For example, in a drilling procedure, the surgical navigation system may be configured to define a first boundary corresponding to a drill, a second boundary corresponding to a tap, and third boundary corresponding to a driver for placing the implant 275, each of the virtual boundaries defined along a target trajectory Axis-T based on the planned pose of the implant 275.

The method may further comprise the step of tracking the position of the surgical instrument 220, 320, 420 using the surgical navigation system 100. This may include the use of machine vision and/or the use of an instrument tracker 230, 330, 430 coupled to the surgical instrument 220, 320, 420.

Upon the surgical navigation system 100 determining the surgical instrument 220, 320, 420 has entered any of the defined virtual boundaries (Boundary 1, 2, 3, 4, 5, 6, 7, 8, 9) and/or alert zones, Zones 1-8B, the surgical navigation system 100 may be configured to signal the processor 215, 265, 315, 415 to deactivate the variable speed motor 245, 345, 445. For example, the surgical navigation system 100 may be configured to send a signal to the battery processor 265 of the first surgical instrument 220, wherein the battery processor 265 is in communication with the first instrument processor 215. The battery processor 265 and/or the instrument processor 215 may be configured to prevent flow of electrical current from the power source, such as a battery 260, to the variable speed motor 245. This may be accomplished using a wired or wireless form of communication between the surgical navigation system 100 and the surgical instrument 220, 320, 420.

The method may further comprise the step of manipulating the virtual boundaries (Boundary 1, 2, 3, 4, 5, 6, 7, 8, 9) and/or alert zone, Zone 1-8B, defined by the surgical navigation based on the medical professional's preference. For example, the medical professional may increase the size and/or thickness of the alert zone to provide an earlier warning of the surgical instrument 220, 320, 420 approaching a boundary or critical anatomical structure. The medical professional may also reposition the alert zone within the patient data. This may include modifying the size, shape, and/or number of alert zones defined within the patient data. The medical professional may similarly manipulate the axial position and/or depth of the virtual boundaries (Boundary 1, 2, 3, 4, 5, 6, 7, 8, 9) along a target trajectory Axis-T to provide an end-effector specific warning. The axial position and/or depth of the virtual boundaries (Boundary 1, 2, 3, 4, 5, 6, 7, 8, 9) along the target trajectory Axis-T may also be manipulated to provide an earlier warning of the surgical instrument 220, 320, 420 approaching a boundary or target depth based on the planned pose of the implant 275. The medical professional may also reposition the virtual boundaries (Boundary 1, 2, 3, 4, 5, 6, 7, 8, 9) within the patient data. This may include modifying the position, depth, shape, and/or number of virtual boundaries (Boundary 1, 2, 3, 4, 5, 6, 7, 8, 9) defined within the patient data.

Wherein the surgical instrument assembly 200, 300, 400, comprises a plurality of end-effectors 240, 340, 440 capable of being removably coupled the handpiece 225, 325, 425, the method may also comprise the step of coupling a first end-effector 240A, 340A to the handpiece 225, 325. The surgical navigation system 100 may be configured to identify the first end-effector 240A, 340A and define a first boundary and/or first alert zone based, at least in part, on the first end-effector. The first boundary may comprise a target depth for the first end-effector 240A, 340A. The method may further comprise the step of coupling a second end-effector 240B, 340B to the handpiece 225, 325. The surgical navigation system 100 may be configured to identify the second end-effector 240B, 340B and define a second boundary and/or second alert zone based, at least in part, on the second end-effector 240B, 340B. The second boundary may comprise a target depth for the second end-effector 240B, 340B, which may be different from the first boundary defined based on the first end-effector 240A, 340A.

The method may further comprise the step of activating an alert device 255, 355, 455 upon the surgical navigation system 100 determining the surgical instrument 220, 320, 420 has entered one of the defined alert zones. This may include activating an audible or tactile alert device. This may also include deactivating the variable speed more 245, 345, 445 of the surgical instrument 220, 320, 420. It may also include reducing the speed of the variable speed motor 245, 345, 445 from a maximum cutting speed to a minimum cutting speed. The change in speed may create a tactile and our audible alert that is perceivable by the medical professional.

The method may further comprise the step of assigning an alert type to each of the defined virtual boundaries and/or alert zones. The surgical navigation system 100 may be configured to automatically assign one or more of the various types of alerts to each of the defined virtual boundaries and/or alert zones based on previously saved profile or system configuration for the medical professional. Alternatively, the medical professional may assign one or more of the various alert types to each of the defined virtual boundaries and/or alert zones using the user input device 130.

The method may also comprise the step of identifying a first end-effector 240A, 340A coupled to the handpiece 225, 325, and the surgical navigation system 100 may be configured define a first boundary and/or first alert zone based, at least in part, on the first end-effector 240A, 340A. The method may then comprise decoupling the first end-effector 240A, 340A from the handpiece 225, 325 and coupling a second end-effector 240B, 340B to the handpiece 225, 325, and the surgical navigation system 100 may be configured to identify the second end-effector 240B, 340B and define a second boundary and/or second alert zone based, at least in part, on the second end-effector 240B, 340B.

The method may further comprise the step of identifying a first end-effector 240A, 340A coupled to the handpiece 225, 325, and the surgical navigation system 100 may be configured to define a first boundary and/or first alert zone based, at least in part, on the first end-effector 240A, 340A. The method may then comprise applying the first end-effector 240A, 340A to biological tissue at the location where the medical implant is to be placed. Upon the surgical navigation system 100 determining the surgical instrument 220, 320, 420 is adjacent and/or distal to the first boundary and/or has entered the first alert zone, the surgical navigation system 100 may be configured to send a signal to the processor 215, 265, 315, 415 to deactivate the variable speed motor 245, 345, 445. It is also contemplated that the surgical navigation system 100 may be configured to send a signal to activate one of the alert devices described above to produce one of the various types of alerts described above. The method may then comprise decoupling the first end-effector 240A, 340A from the handpiece 225, 325 and coupling a second end-effector 240B, 340B to the handpiece 225, 325, 425. The surgical navigation system 100 may be configured to identify the second end-effector 240B, 340B and define a second boundary and/or second alert zone based, at least in part, on the second end-effector 240B, 340B. The method may also comprise applying the second end-effector 240B, 340B to biological tissue at the location where the medical implant is to be placed. Upon the surgical navigation system 100 determining the surgical instrument 220, 320, 420 is adjacent and/or distal to the second boundary and/or has entered the second alert zone, the surgical navigation system 100 may be configured to send a signal to the processor to deactivate the variable speed motor. It is also contemplated that the surgical navigation system 100 may be configured to send a signal to activate one of the alert devices described above to produce one of the various types of alerts described above.

In another configuration, the navigation system is configured to communicate a first signal to the processor of the control console based on a position of the end-effector relative to the alert zone. The signal may cause the control console to compare a sensed speed to a desired speed of the handpiece based on a torque map. Using the torque map, the console may determine a calculated torque of the cutting tool based on a sensed speed of the cutting tool. Then, based on the calculated torque of the cutting tool and the sensed speed of the cutting tool, the console may determine a calculated power consumed by the cutting tool. The torque map also provides a desired power consumed by the cutting tool and a desired torque and a desired speed of the cutting tool at the desired power consumed. The navigation system may be configured to cause the console to adjust a torque map based on the end-effector entering the alert zone. More specifically, the control console may power the bur with reduced torque once the end-effector is adjacent and/or distal to the virtual boundary and/or enters the alert zone such that the end-effector cuts less effectively and/or aggressively when the end-effector is adjacent and/or distal to the virtual boundary and/or within the alert zone.

Clauses covering additional configurations of the system(s) described above:

I. A surgical instrument assembly for use with a navigation system configured to allow a medical professional to define an alert zone on the patient to assist the medical professional in performing spinal or cranial surgery on the patient, said surgical instrument assembly comprising:
   a control console comprising a control processor in communication with the navigation system;
   a high-speed surgical bur comprising a variable speed motor in communication with said control processor, said variable speed motor configured to rotate a bur at a first cutting speed of greater than 70,000 rotations per minute and a second cutting speed of below 70,000 rotations per minute and above 60,000 rotations per minute; and
   a footswitch for controlling operation of said variable speed motor of said high-speed surgical bur in communication with said control processor;
   wherein the navigation system is configured to actively determine a position of said high-speed surgical bur relative to the patient;
   wherein the navigation system is configured to send a signal to said control processor to manipulate said variable speed motor of said high-speed surgical bur to transition the rotation of said bur from said first cutting speed to said second cutting speed when the navigation system determines said high-speed surgical bur enters said alert zone; and
   wherein the transition of said bur from said first cutting speed to said second cutting speed creates an audibly perceptible change in the pitch produced by said high-speed surgical bur as it transitions from said first cutting speed to said second cutting speed to notify the medical professional that said high-speed surgical bur has entered said alert zone without compromising the ability of said bur to continue to cut biological tissue.

II. The surgical instrument assembly of clause I, wherein the transition of said bur from said first cutting speed to said second cutting speed creates a tactile perceptible change in said high-speed surgical bur as it transitions from said first cutting speed to said second cutting speed to notify the medical professional that said high-speed surgical bur has entered said alert zone without compromising the ability of said bur to continue to cut biological tissue.

III. The surgical instrument assembly of clause I, wherein said footswitch moveable between a first position and a second position; and
wherein said variable speed motor is configured to be deactivated when the footswitch is in said first position and said variable speed motor is configured to rotate a bur at a minimum of 60,000 rotations per minute when is said second position.

IV. The surgical instrument assembly of clause I, further comprising an audible alert device configured to emit an alert sound when said high-speed surgical bur enters said alert zone.

V. The surgical instrument assembly of clause I, further comprising a tactile alert device in contact with the medical professional, said tactile alert device configured to emit a physical alert that is capable of being perceived by the medical professional when said high-speed surgical bur enters said alert zone.

VI. The surgical instrument assembly of clause V, wherein said tactile alert device is coupled to said footswitch, such that said physical alert would be felt in the medical professional's appendage that is in contact with said footswitch for controlling operation of said variable speed motor of said high-speed surgical bur.

VII. The surgical instrument assembly of clause V, wherein said alert zone comprises a first zone and a second zone; and
wherein said tactile device is configured to produce a first notification when said high-speed surgical bur enters said first zone and to produce a second notification when said high-speed surgical bur enters said second zone.

VIII. The surgical instrument assembly of clause I, further comprising an audible alert device and a tactile alert device in contact with the medical professional, each of said audible alert device and said tactile alert device being capable of producing an alert that is perceived by the medical professional when said high-speed surgical bur enters said alert zone.

IX. The surgical instrument assembly of clause I, further comprising at least one of an audible alert device capable of producing a first notification and a tactile alert device capable of producing a second notification;
wherein said alert zone comprises a user-definable first zone and a user-definable second zone;
wherein the navigation system is configurable to allow the user to assign one of said first notification or said second notification to either of said first zone or said second zone; and
wherein the navigation system is configurable to manipulate one of said audible alert device and said tactile alert device based on the position of said high-speed surgical bur and said first notification or said second notification assigned to said one of said first zone or said second zone.

X. A surgical system for use by a medical professional in spinal or cranial surgery on a patient, said surgical system comprising:
a control console comprising a control processor;
a high-speed surgical bur comprising a variable speed motor in communication with said control processor, said variable speed motor configured to rotate a bur at a first cutting speed of greater than 70,000 rotations per minute and a second cutting speed of between 60,000 rotations per minute and 65,000 rotations per minute;
a footswitch for controlling operation of said variable speed motor of said high-speed surgical bur in communication with said control processor;
a navigation system in communication with said control console, said navigation system configured to allow the medical professional to define an alert zone on the patient and to actively determine a position of said high-speed surgical bur relative to the patient and communicate said position to said control processor; and
wherein said navigation system is configured to communicate a signal to the control processor to manipulate said variable speed motor of said high-speed surgical bur to transition the rotation of said bur from said first cutting speed to said second cutting speed upon said navigation system determining said bur of said high-speed surgical bur has entered said alert zone;
wherein the transition of said bur from said first cutting speed to said second cutting speed creates an audibly perceptible change in the pitch of said variable speed motor of said high-speed surgical bur to notify the medical professional that said high-speed surgical bur has entered said alert zone without compromising the ability of said bur to continue to cut biological tissue.

XI. The surgical system of clause X, wherein the transition of said bur from said first cutting speed to said second cutting speed creates a tactile perceptible change in said high-speed surgical bur as it transitions from said first cutting speed to said second cutting speed to notify the medical professional that said high-speed surgical bur has entered said alert zone without compromising the ability of said bur to continue to cut biological tissue.

XII. The surgical system of clause XI, said footswitch moveable between a first position and a second position; and
wherein said variable speed motor is configured to be deactivated when the footswitch is in said first position and said variable speed motor is configured to rotate a bur at a minimum of 60,000 rotations per minute when is said second position.

XIII. The surgical system of clause X, further comprising an audible alert device configured to emit an alert sound when said high-speed surgical bur enters said alert zone.

XIV. The surgical system of clause X, further comprising a tactile alert device in contact with the medical professional, said tactile alert device configured to emit a physical alert that is capable of being perceived by the medical professional when said high-speed surgical bur enters said alert zone.

XV. The surgical system of clause XIV, wherein said tactile alert device is coupled to said footswitch, such that said physical alert would be felt in the medical professional's appendage that is in contact with said footswitch for controlling operation of said variable speed motor of said high-speed surgical bur.

XVI. The surgical system of clause XIV, wherein said alert zone comprises a first zone and a second zone; and
wherein said tactile alert device is configured to produce a first notification when said high-speed surgical bur enters said first zone and to produce a second notification when said high-speed surgical bur enters said second zone.

XVII. The surgical system of clause X, further comprising an audible alert device and a tactile alert device in contact with the medical professional, each of said audible alert device and said tactile alert device being capable of producing an alert that is perceived by the medical professional when said high-speed surgical bur enters said alert zone.

XVIII. A surgical system for use with a surgical navigation system capable of defining an alert zone on a patient to assist a medical professional in performing spinal or cranial surgery on the patient, said surgical system comprising:
- a high-speed surgical bur comprising a variable speed motor configured to rotate a bur;
- a control console comprising a control processor, said control processor in communication with said variable speed motor of said high speed surgical bur and configured to receive data from the surgical navigation system related to the defined alert zones and the position of said high-speed surgical bur relative to the defined alert zones;
- a footswitch in communication with said control processor, said footswitch movable between a first position and a second position for controlling operation of said variable speed motor of said high-speed surgical bur;
- wherein when said footswitch is in said first position, said variable speed motor is deactivated and said bur is rotated at a rate of zero rotations per minute;
- wherein when said footswitch is in said second position, said variable speed motor is configured to rotate said bur at a maximum cutting rate;
- wherein when said footswitch is in an intermediate position between said first position and said second position, said variable speed motor is configured to rotate said bur at an intermediate rate between a minimum cutting rate and said maximum cutting rate; and
- wherein the navigation system is configured to send data to said control processor that said bur has entered the alert zone and to manipulate said variable speed motor of said high-speed surgical bur to reduce rotation of said bur to said minimum cutting rate when said footswitch is positioned in said intermediate position or said second position.

XIX. The surgical system of clause XVIII, further comprising a tactile alert device coupled to said footswitch and in communication with said control console; and
wherein said control console is configured to manipulate said tactile alert device to produce a physical notification perceivable by the medical professional when said bur enters said alert zone.

XX. A surgical instrument assembly for use with a navigation system capable of defining an alert zone on a patient to assist a medical professional in performing spinal or cranial surgery on the patient, said surgical instrument assembly comprising:
- a high-speed surgical bur comprising a variable speed motor configured to rotate a bur;
- a control console comprising a control processor, said control processor in communication with said variable speed motor of said high speed surgical bur and configured to receive data from the surgical navigation system; and
- a footswitch in communication with said control processor for controlling operation of said variable speed motor of said high-speed surgical bur, said footswitch comprising a tactile alert device;
- wherein the navigation system is configured to send data to said control processor that said bur has entered the defined alert zone and is configured to manipulate said tactile alert device of said footswitch to notify the medical professional when said bur enters said alert zone.

XXI. A method of navigating a medical instrument having a variable speed motor using a navigation system including an instrument tracker coupled to the medical instrument and a patient tracker coupled to a patient, said method comprising:
- defining alert zones within pre-operative data of the patient;
- registering the alert zones to the patient tracker;
- tracking the position of the medical instrument using the position and orientation of the instrument tracker relative to the patient tracker; and
- manipulating the speed of the variable speed motor of the medical instrument between a maximum cutting speed and a minimum cutting speed based on the position of the medical instrument relative to the defined alert zones.

XXII. The method of clause XXI, wherein manipulating the speed of the variable speed motor comprises decelerating the variable speed motor from the maximum cutting speed to the minimum cutting speed when the medical instrument enters the defined alert zones.

XIII The method of clause XXII, wherein decelerating the variable speed motor from the maximum cutting speed to the minimum cutting speed when the medical instrument enters the defined alert zones generates an audibly perceptible change in the pitch produced by the variable speed motor to notify a medical professional that the medical instrument has entered the defined alert zones without compromising the ability of the medical instrument to continue to cut biological tissue.

XXIV. The method of clause XXI, further comprising activating an alert device to produce at least one of an audible, a haptic, or, a visual notification based on the position of the medical instrument relative to the defined alert zones.

XXV. The method of clause XXIV, wherein the defined alert zones comprise a first zone and a second zone; and
wherein the step of activating the alert device comprises producing the haptic notification when the medical instrument enters the first zone and producing the audible notification when the medical instrument enters the second zone.

XXVI. A surgical system for use by a medical professional in spinal or cranial surgery on a patient, said surgical system comprising:
- a hand-held surgical instrument configured to drive an end-effector comprising:
  - a variable speed motor;
  - a trigger manipulatable by the medical professional between a first position and a second position;
  - a trigger sensor configured to detect said position of said trigger and output a first signal indicative of said position of said trigger; and
  - a handpiece processor in communication with said trigger sensor, said handpiece processor configured to control energization of said variable speed motor based, at least in part, on said first signal indicative of said position of said trigger;

a rechargeable battery module removably coupled to said hand-held surgical instrument, said battery module comprising:
   a transceiver configured to send and receive a signal;
   a battery processor in communication with said transceiver, said processor being configured to provide power to said hand-held surgical instrument;
   a navigation system in communication with said battery processor via said transceiver, said navigation system configured to actively determine a position of said surgical instrument relative to an alert zone defined on the patient;
   wherein said navigation system is configured to communicate a second signal to said battery processor to cut power to said hand-held surgical instrument upon said navigation system determining said position of said surgical instrument has entered said alert zone; and
   wherein upon said battery processor cutting power to said hand-held surgical instrument and said surgical instrument remains in said alert zone, said handpiece processor is configured to prevent energization of said variable speed motor until a subsequent said first signal is received from said trigger sensor is received indicating the medical professional has manipulated said position of said trigger.

XXVII. The surgical system of clause XXVI, wherein said rechargeable battery module further comprises:
   a cell for storing electric energy for powering said variable speed motor of said hand-held surgical instrument; and
   a switch in communication with said battery processor and configured to control the flow of electrical energy from said cell, said switch having an energized state configured to allow flow of electrical energy from said cell and a deenergized state configured to prevent flow of electrical energy from said cell.

XXVIII. A surgical system for use by a medical professional in surgery on a patient, said surgical system comprising:
   a hand-held surgical instrument configured to drive an end-effector comprising:
      a variable speed motor;
      a switch manipulatable by the medical professional between a first position and a second position;
      a switch sensor configured to detect said position of said switch and output a first signal indicative of said position of said switch; and
      a handpiece processor in communication with said switch sensor, said handpiece processor configured to control energization of said variable speed motor based, at least in part, on said first signal indicative of said position of said switch;
   a power source removably coupled to said hand-held surgical instrument and configured to provide power to said hand-held surgical instrument;
   a navigation system in communication with said handpiece processor, said navigation system configured to actively determine a position of said surgical instrument relative to an alert zone defined on the patient;
   wherein said navigation system is configured to communicate a second signal to said handpiece processor to deenergize said variable speed motor upon said navigation system determining said position of said surgical instrument has entered said alert zone; and
   wherein upon de-energization of said hand-held surgical instrument and while said surgical instrument remains in said alert zone, said handpiece processor is configured to prevent reenergization of said variable speed motor until a subsequent said first signal is received from said switch sensor is received indicating the medical professional has manipulated said position of said switch.

XXIX. The surgical system of clause XXVIII, further comprising rechargeable battery module removably coupled to said hand-held surgical instrument, said battery module comprising:
   a transceiver configured to send and receive a signal;
   a cell for storing electric energy for powering said variable speed motor of said hand-held surgical instrument; and
   a switch configured to control the flow of electrical energy from said cell, said switch having an energized state configured to allow flow of electrical energy from said cell and a deenergized state configured to prevent flow of electrical energy from said cell; and
   a battery processor in communication with said transceiver and said switch, said battery processor being configured to manipulate said switch between said energized state and said deenergized state to selectively provide power to said hand-held surgical instrument based, at least in part, on said signals received by said transceiver.

XXX. A surgical system for use by a medical professional in surgery on a patient, said surgical system comprising:
   a high-speed bur assembly comprising:
      a control console including a processor;
      a handpiece in communication with said processor of said control console, said handpiece comprising an end-effector and a variable speed motor for driving said end-effector;
      a footswitch manipulatable by the medical professional between a first position and a second position for controlling the energization of said variable speed motor;
      a switch sensor configured to detect the position of said foot switch and communicate a first signal to said processor indicative of said position of said foot switch;
   a navigation system in communication with said processor, said navigation system configured to actively determine a position of said handpiece relative to an alert zone defined on the patient;
   wherein said navigation system is configured to communicate a second signal to said processor to deenergize said variable speed motor upon said navigation system determining said position of said handpiece has entered said alert zone; and
   wherein upon de-energization of said handpiece and while said handpiece remains in said alert zone, said processor is configured to prevent reenergization of said variable speed motor until a subsequent said first signal is received from said switch sensor is received indicating the medical professional has manipulated said position of said foot switch.

XXXI. The surgical system of clause XXX, further comprising a tactile alert device in contact with the medical professional, said tactile alert device configured to emit a physical alert that is capable of being perceived by the medical professional when said high-speed surgical bur enters said alert zone.

XXXII. The surgical system of clause XXX, further comprising an audible alert device and a tactile alert device in contact with the medical professional, each of said audible alert device and said tactile alert device being capable of producing an alert that is perceived by the medical professional when said high-speed surgical bur enters said alert zone.

XXXIII. A surgical system for use by a medical professional in spinal or cranial surgery on a patient, said surgical system comprising:
- a hand-held surgical instrument configured to drive an end-effector comprising:
  - a variable speed motor;
  - a trigger manipulatable by the medical professional between a first position and a second position; and
  - a handpiece processor configured to control energization of said variable speed motor based, at least in part, on said position of said trigger;
- a rechargeable battery module removably coupled to said hand-held surgical instrument, said battery module comprising:
  - a transceiver configured to send and receive a signal;
  - a battery processor in communication with said transceiver, said processor being configured to energize and deenergize said hand-held surgical instrument;
- a navigation system in communication with said battery processor via said transceiver, said navigation system configured to actively determine a position of said hand-held surgical instrument relative to an alert zone defined on the patient;
- wherein said navigation system is configured to communicate a first signal to said battery processor to temporarily deenergize said hand-held surgical instrument upon said navigation system determining said position of said hand-held surgical instrument has entered said alert zone;
- while said hand-held surgical instrument remains in said alert zone and after said battery processor deenergizes said handheld surgical instrument; and
- said battery processor reenergizing said variable speed motor, said navigation system is configured to communicate a second signal to said battery processor to cause said battery processor to energize or deenergize said hand-held surgical instrument based on the motion of said hand-held surgical instrument being in a proximal or distal direction relative to a surgical site on the patient.

XXXIV. A surgical system for use by a medical professional to perform surgical procedure on a patient, said surgical system comprising:
- a hand-held surgical instrument configured to accept an end-effector, said hand-held surgical instrument comprising:
  - a variable speed motor configured to rotate said end-effector;
  - a trigger manipulatable by the medical professional between a first position and a second position;
  - a trigger sensor configured to detect said position of said trigger and output a first signal indicative of said position of said trigger; and
  - a handpiece processor configured to control energization of said variable speed motor based, at least in part, upon said first signal from said trigger sensor indicating said position of said trigger;
- a navigation system in communication with said processor, said navigation system configured to define an alert zone on the patient and to actively determine a position of said surgical instrument relative to said alert zone and communicate a second signal to said handpiece processor to deactivate said variable speed motor when said trigger sensor indicates said trigger is in said second position and said navigation system determines said hand-held surgical instrument has entered said alert zone; and
- while said hand-held surgical instrument remains in said alert zone, said handpiece processor is configured to reactivate said variable speed motor upon receiving a subsequent said first signal from said trigger sensor indicating the medical professional has manipulated said trigger to move said trigger from said second position to said first position and back to said second position.

XXXV. The surgical system of clause XXXIV, wherein upon reactivation of said variable speed motor while said hand-held surgical instrument remains in said alert zone, said navigation system is configured to communicate a third signal to said handpiece processor to deactivate said variable speed motor upon said navigation system determining said hand-held surgical instrument has moved a defined distance proximally toward a surgical site (said alert zone) on the patient.

XXXVI. The surgical system of clause XXXIV, wherein upon reactivation of said variable speed motor while said hand-held surgical instrument remains in said alert zone, said navigation system is configured to communicate a fourth signal to said handpiece processor to maintain activation of said variable speed motor upon said navigation system determining said hand-held surgical instrument is moving distal to a surgical site (said alert zone) on the patient.

XXXVII. A surgical system for use by a medical professional in spinal or cranial surgery on a patient, said surgical system comprising:
- a hand-held surgical instrument configured to accept an end-effector, said hand-held surgical instrument comprising:
  - a variable speed motor;
  - a trigger manipulatable by the medical professional between a first position and a second position to activate and deactivate said variable speed motor; and
  - a processor configured to control energization of said variable speed motor;
- a navigation system in communication with said processor, said navigation system configured to allow the medical professional to define a target axis on the patient and an instrument test distance threshold;
- wherein said navigation system is configured to determine an actual axis of said hand-held surgical instrument relative to said target axis and determine a position of said hand-held surgical instrument relative to a target depth and compare the result to an instrument test distance threshold; and
- when said navigation system determines that said position of said hand-held surgical instrument is closer to said target depth than said instrument test distance threshold and said actual axis of said hand-held surgical instrument is misaligned with said target axis, said navigation system is configured communicate a first signal to said processor to prevent energization of said variable speed motor;

when said navigation system determines that said position of said hand-held surgical instrument is farther from said target depth than said instrument test distance threshold, said navigation system does not cause said processor to prevent energization of said variable speed motor irrespective of whether said actual axis of said hand-held surgical instrument is misaligned with said target axis.

XXXVIII. The surgical system of clause XXXVII, while said trigger is in said second position to activate said variable speed motor, said navigation system is configured to communicate a fifth signal to said processor to deactivate said variable speed motor upon said navigation system determining said hand-held surgical instrument is positioned on said target axis and has reached said target depth.

XXXIX. A surgical system for use by a medical professional in spinal or cranial surgery on a patient, said surgical system comprising:
a hand-held surgical instrument configured to accept an end-effector, said hand-held surgical instrument comprising:
a handpiece;
a variable speed motor disposed within said handpiece;
a trigger manipulatable by the medical professional to activate and deactivate said variable speed motor;
a switch manipulatable by the medical professional between a first position and a second position for controlling a speed of said variable speed motor;
a processor configured to control energization of said variable speed motor;
a navigation system in communication with said processor, said navigation system configured to determine whether said switch is in said first position or said second position; and
wherein said navigation system is configured to communicate a signal to said processor to control energization of said variable speed motor based on said switch being in appropriate said position and based on a type of said end-effector coupled to said hand-held surgical instrument.

XL. The surgical system of clause XXXIX, wherein said navigation system is configured to communicate said signal to said processor to deactivate said variable speed motor upon said navigation system identifying said switch is in incorrect said position for said type of said end-effector that is coupled to said hand-held surgical instrument; and
wherein said navigation system is configured to communicate said signal to said processor to activate said variable speed motor upon said navigation system identifying said switch is in correct said position for said type of said end-effector that is coupled to said surgical instrument.

XLI. The surgical system of clause XXXIX or XL, wherein said hand-held surgical instrument further comprises a tracker coupled to said switch; and
Wherein said navigation system is configured to determine whether said switch is in said first position or said second position based on said position of said tracker.

XLII. The surgical system of any of clauses XXXIX-XLI, wherein said hand-held surgical instrument further comprises a battery module; and
wherein said processor is disposed within said battery module.

XLIII. A surgical system for use by a medical professional in spinal or cranial surgery on a patient, said surgical system comprising:
a hand-held surgical instrument assembly comprising:
a handpiece;
one of a first end-effector or a second end-effector, each of said first end-effector and said second end-effector removably couplable to said handpiece;
a variable speed motor disposed within said handpiece;
an optional feedback device that vibrates; and
a processor configured to control energization of said variable speed motor and/or vibration of said feedback device;
a navigation system in communication with said processor, said navigation system configured to define a first alert zone on the patient based, at least in part, on said first end-effector and to define a second alert zone on the patient based, at least in part, on said second end-effector; and
when said first end-effector is coupled to said handpiece, said navigation system is configured to communicate a first signal to said processor to control energization of said variable speed motor or to vibrate said feedback device based, at least in part, on position of said first end-effector relative to said first alert zone;
when said second end-effector is coupled to said handpiece, said navigation system is configured to communicate a signal to said processor to control energization of said variable speed motor or to vibrate said feedback device based, at least in part, on position of said second end-effector relative to said second alert zone.

XLIV. The surgical system of clause XLIII, wherein said navigation system is configured to actively determine a position of said hand-held surgical instrument relative to said alert zone and communicate said position to said processor.

XLV. The surgical system of clause XLIII, wherein said navigation system is configured to communicate a signal to said processor to deactivate said variable speed motor upon said navigation system determining said first end-effector has entered said first alert zone or said second end-effector has entered said second alert zone.

XLVI. The surgical system of clause XLIII, wherein said hand-held surgical instrument further comprises:
a footswitch in electrical communication with said processor; and
a feedback device is coupled to said footswitch.

XLVII. The surgical system of clause XLIII, wherein said navigation system is configured to allow said medical professional to input the type of said first end-effector or said second end-effector that is coupled to said hand-held surgical instrument.

XLVIII. The surgical system of clause of any of clauses XLIII-XLVII, hand-held surgical instrument assembly comprises a battery module; and
wherein said optional feedback device is disposed within said battery module.

XLIX. A surgical system for use by a medical professional in spinal or cranial surgery on a patient, said surgical system comprising:
- a high-speed bur assembly comprising:
  - a control console comprising a processor;
  - a handpiece a handpiece in communication with said processor of said control console;
  - one of a first end-effector or a second end-effector, each of said first end-effector and said second end-effector removably couplable to said handpiece;
  - a variable speed motor disposed within said handpiece;
  - an optional feedback device; and
  - wherein said processor is configured to control energization of said variable speed motor and/or vibration of said feedback device;
- a navigation system in communication with said processor, said navigation system configured to define a first alert zone on the patient based, at least in part, on said first end-effector and to define a second alert zone on the patient based, at least in part, on said second end-effector; and
- when said first end-effector is coupled to said handpiece, said navigation system is configured to communicate a first signal to said processor to control energization of said variable speed motor or to activate said feedback device based, at least in part, on position of said first end-effector relative to said first alert zone;
- when said second end-effector is coupled to said handpiece, said navigation system is configured to communicate a signal to said processor to control energization of said variable speed motor or to activate said feedback device based, at least in part, on position of said second end-effector relative to said second alert zone.

L. The surgical system of clause XLIX, wherein said optional feedback device comprises a tactile alert device in contact with the medical professional, said tactile alert device configured to emit a physical alert that is capable of being perceived by the medical professional when said high-speed surgical bur enters said alert zone.

LI. The surgical system of clause XLIX, wherein said optional feedback device comprises an audible alert device and a tactile alert device in contact with the medical professional, each of said audible alert device and said tactile alert device being capable of producing an alert that is perceived by the medical professional when said high-speed surgical bur enters said alert zone.

LII. The surgical system of clause XLIX or L, wherein said high-speed bur assembly further comprises a footswitch coupled to said control console, said footswitch moveable between a first position and a second position to control energization of said variable speed motor; wherein said medical professional may deactivate said optional feedback device by manipulating said foot switch in a defined pattern within a define time frame.

LIII. Method of navigating a surgical instrument using a surgical navigation system during a medical procedure on a patient, the surgical instrument including a handpiece, an end-effector coupled to the handpiece, variable speed motor for selectively actuating the end-effector, and a processor for controlling energization of said variable speed motor, said method comprising:
- selecting a medical implant;
- identifying location where the medical implant is to be placed on the patient within patient data stored on the surgical navigation system, wherein the surgical navigation system is configured to define an alert zone based on the selected medical implant and the identified location where the medical implant is to be placed;
- tracking the position of the surgical instrument using the surgical navigation system;
- upon the navigation system determining the surgical instrument has entered the defined alert zone, the surgical navigation system signaling to the processor to deactivate the variable speed motor.

LIV. The method of clause LIII, wherein the method further comprises the step of manipulating the alert zone define by the surgical navigation based on the medical professional's preference.

LV. The method of clause LIII or LIV, wherein the method further comprises the step of coupling a first end-effector to the handpiece, the surgical navigation system configured to identify the first end-effector and define a first alert zone based, at least in part, on the first end-effector.

LVI. The method of any of clauses LIIILV, wherein the method further comprises the step of coupling a second end-effector to the handpiece, the surgical navigation system configured to identify the second end-effector and define a second alert zone based, at least in part, on the second end-effector.

LVII. The method of any of clauses LIII-LVI, wherein said method further comprises the step of activating an alert device upon the surgical navigation system determining the surgical instrument has entered the defined alert zone.

LVIII. The method of any of clauses LIII-LVII, wherein said method further comprises the step of assigning an alert type to each of the defined alert zones.

LIX. The method of clause LIII, wherein said method further comprises the step of identifying a first end-effector coupled to the handpiece, the surgical navigation system configured define a first alert zone based, at least in part, on the first end-effector;
- decoupling the first end-effector from the handpiece;
- coupling a second end-effector to the handpiece, the surgical navigation system configured to identify the second end-effector and define a second alert zone based, at least in part, on the second end-effector.

LX. The method of clause LIII, wherein said method further comprises the step of identifying a first end-effector coupled to the handpiece, the surgical navigation system configured define a first alert zone based, at least in part, on the first end-effector;
- applying the first end effector to biological tissue location where the medical implant is to be placed;
- upon the navigation system determining the surgical instrument has entered the first alert zone, the surgical navigation system signaling to the processor to deactivate the variable speed motor;
- decoupling the first end-effector from the handpiece;
- coupling a second end-effector to the handpiece, the surgical navigation system configured to identify the second end-effector and define a second alert zone based, at least in part, on the second end-effector;

applying the second end effector to biological tissue location where the medical implant is to be placed; and upon the navigation system determining the surgical instrument has entered the second alert zone, the surgical navigation system signaling to the processor to deactivate the variable speed motor.

LXI. A surgical system for use by a medical professional in surgery on a patient, said surgical system comprising:
- a high-speed bur assembly comprising:
  - a control console including a processor;
  - a handpiece in communication with said processor of said control console, said handpiece comprising an end-effector and a variable speed motor for driving said end-effector;
  - a footswitch manipulatable by the medical professional between a first position and a second position for controlling the energization of said variable speed motor;
- a navigation system in communication with said processor, said navigation system configured to actively determine a position of said handpiece relative to an alert zone defined on the patient;
- wherein said navigation system is configured to communicate a first signal to said processor to temporarily deenergize said handpiece upon said navigation system determining said position of said handpiece has entered said alert zone;
- wherein upon said processor temporarily deenergizing said handpiece, said handpiece remains in said alert zone; and
- wherein upon reenergizing said variable speed motor, said navigation system is configured to communicate a second signal to said processor to cause said processor to energize or deenergize said handpiece based on the motion of said handpiece being in a proximal or distal direction relative to a surgical site on the patient.

LXII. A surgical instrument assembly for use with a navigation system configured to allow a medical professional to define an alert zone on the patient to assist the medical professional in performing surgery on the patient, said surgical instrument assembly comprising:
- a control console comprising a control processor in communication with the navigation system;
- a high-speed surgical bur assembly comprising a variable speed motor in communication with said control processor, said variable speed motor configured to rotate a bur;
- a footswitch moveable between a first position and a second position for energizing said variable speed motor of said high-speed surgical bur
- a footswitch sensor in communication with said control processor, said footswitch configured to detect said position of said footswitch and communicate a first signal to said control processor indicative of said position of said footswitch; and
- a tactile alert device coupled to said footswitch and in communication with said control processor, said tactile alert device position on said footswitch so that said tactile alert device is in contact with the medical professional when the medical professional compresses said footswitch to operate said high-speed surgical bur;
- wherein the navigation system is configured to actively determine a position of said high-speed surgical bur relative to the patient;
- wherein the navigation system is configured to send a second signal to said control processor to activate said tactile alert device to emit a physical alert that is capable of being perceived by the medical professional when said high-speed surgical bur enters the alert zone; and
- wherein, while said high-speed surgical bur is still within the alert zone, said processor is configured deactivate said alert device upon receiving a subsequent said first signal from said footswitch sensor indicating the medical professional moved said footswitch between said first position and said second position a defined number of strokes within a defined period of time.

LXIII A surgical system for use by a medical professional in surgery on a patient, said surgical system comprising:
- a high-speed bur assembly comprising:
  - a control console including a processor;
  - a handpiece in communication with said processor of said control console, said handpiece comprising an end-effector and a variable speed motor for driving said end-effector;
  - a footswitch manipulatable by the medical professional between a first position and a second position for controlling the energization of said variable speed motor;
- a navigation system in communication with said processor, said navigation system configured to actively determine a position of said handpiece relative to an alert zone defined on the patient;
- wherein said navigation system is configured to communicate a first signal to said processor to cause said processor to adjust a torque map by which the handpiece is powered in response to the end effector entering the alert zone.

LXIV. A surgical system for use by a medical professional in spinal or cranial surgery on a patient, said surgical system comprising:
- a hand-held surgical instrument configured to accept an end-effector, said hand-held surgical instrument comprising:
  - a handpiece;
  - a variable speed motor disposed within said handpiece;
  - a trigger manipulatable by the medical professional to activate and deactivate said variable speed motor;
  - a switch manipulatable by the medical professional between a first position and a second position for controlling a speed of said variable speed motor;
  - a processor configured to control energization of said variable speed motor;
- a navigation system in communication with said processor, said navigation system configured to determine whether said switch is in said first position or said second position with machine vision; and
- wherein said navigation system is configured to communicate a signal to said processor to control energization of said variable speed motor based on said switch being in appropriate said position and based on a type of said end-effector coupled to said hand-held surgical instrument.

LXV. The surgical system of clause LXIV, wherein said hand-held surgical instrument further comprises a tracker coupled to said switch; and
   wherein said navigation system is configured to determine whether said switch is in said first position or said second position based on said position of said tracker.

LXVI. The surgical system of clause LXIV or LXV, wherein said hand-held surgical instrument further comprises a battery module; and
   wherein said processor is disposed within said battery module.

LXVII. A surgical navigation system for use in guiding a surgical instrument to execute a medical procedure, said surgical navigation system substantially as described in any of the preceding clauses.

Several embodiments have been discussed in the foregoing description. However, the embodiments discussed herein are not intended to be exhaustive or limit the invention to any particular form. The terminology which has been used is intended to be in the nature of words of description rather than of limitation. Many modifications and variations are possible in light of the above teachings and the invention may be practiced otherwise than as specifically described.

What is claimed is:

1. A surgical system configured to allow a medical professional to define an alert zone relative to a critical structure on a patient in a known coordinate system to assist the medical professional in performing surgery on a patient, the surgical system comprising:
   a navigation system;
   a control console comprising a control processor in communication with the navigation system;
   a high-speed surgical instrument including a bur, the high-speed surgical instrument comprising a variable speed motor in communication with the control processor, the variable speed motor configured to rotate the bur at a first cutting speed of greater than 70,000 rotations per minute and a second cutting speed of below 70,000 rotations per minute and above 60,000 rotations per minute; and
   a footswitch for controlling operation of the variable speed motor of the high-speed surgical instrument in communication with the control processor;
   wherein the navigation system is configured to actively determine a position of the bur relative to the alert zone in the known coordinate system;
   wherein the navigation system is configured to send a signal to the control processor to manipulate the variable speed motor of the high-speed surgical instrument to transition the rotation of the bur from the first cutting speed to the second cutting speed when the navigation system determines the bur enters the alert zone; and
   wherein the transition of the bur from the first cutting speed to the second cutting speed creates a perceptible change as the bur transitions from the first cutting speed to the second cutting speed to notify the medical professional that the bur has entered the alert zone.

2. The surgical system of claim 1, wherein the footswitch is moveable between a first position and a second position, and
   wherein the variable speed motor is configured to be deactivated when the footswitch is in the first position and the variable speed motor is configured to rotate a bur at a minimum of 60,000 rotations per minute when not in the first position.

3. The surgical system of claim 1, wherein after receiving the signal from the navigation system to manipulate the variable speed motor from the first cutting speed to the second cutting speed upon the bur entering the alert zone, the control processor is configured to manipulate the variable speed motor of the high-speed surgical instrument to return the rotation of the bur to the first cutting speed upon a user moving the footswitch.

4. The surgical system of claim 3, wherein the footswitch is moveable between a first position and a second position,
   wherein the variable speed motor is configured to be deactivated when the footswitch is in the first position and the variable speed motor is configured to rotate a bur at a minimum of 60,000 rotations per minute when not in the first position, and
   wherein the moving the footswitch is defined as moving the footswitch to the first position and repositioning the footswitch such that it is not in the first position.

5. The surgical system of claim 1, further comprising a tactile alert device in contact with the medical professional, the tactile alert device configured to emit a tactile alert that is capable of being perceived by the medical professional when the bur enters the alert zone.

6. The surgical system of claim 5, wherein the tactile alert device is coupled to the footswitch, the tactile alert device comprising a motor that vibrates when activated such that the vibration of the motor provides a physical alert capable of being felt in a user's foot that is in contact with the footswitch for controlling operation of the variable speed motor of the high-speed surgical instrument.

7. The surgical system of claim 1, wherein the alert zone comprises a user-selectable first boundary and a user-selectable depth relative to the first boundary.

8. The surgical system of claim 1, further comprising at least one of an audible alert device and a tactile alert device in contact with the medical professional, each of the audible alert device and the tactile alert device being capable of producing an alert that is perceived by the medical professional when the bur enters the alert zone,
   wherein the alert zone comprises a first alert zone and a second alert zone, and the navigation system is configured to allow a user to assign one of a first notification type or a second notification type to the first alert zone, the second alert zone, or a combination thereof, and
   wherein the navigation system is configured to manipulate one of the audible alert device and the tactile alert device based on the position of the bur, the first alert zone, the second alert zone, and the first notification type or the second notification type assigned to the one of the first alert zone or the alert zone.

9. The surgical system of claim 8, wherein the navigation system comprises a graphical user interface (GUI) including graphics directed to the alert zone, the alert zone being selectable by manipulation of the graphical user interface (GUI),
   wherein the graphical user interface (GUI) is configured to provide a user-selectable icon configured to disable at least one of the audible alert device and the tactile alert device after the bur enters the alert zone, and
   wherein the control processor is configured to reactivate the disabled at least one of the audible alert device and the tactile alert device based on the position of the bur being outside the alert zone for a predetermined period of time, and subsequently returning to the alert zone.

10. The surgical system of claim 1, further comprising at least one of an audible alert device capable of producing a first notification and a tactile alert device capable of producing a second notification,
   wherein the alert zone comprises a user-selectable first boundary and a user-selectable second boundary,
   wherein the navigation system is configured to allow a user to assign one of the first notification or the second notification to either of the first boundary or the second boundary, and
   wherein the navigation system is configured to manipulate one of the audible alert device and the tactile alert device to produce one of the first notification or the second notification based on the position of the bur relative to the first boundary or the second boundary.

11. The surgical system of claim 1, wherein the navigation system is configured to define a boundary based, at least in part, on a segmentation algorithm, the boundary at least partially defining the alert zone.

12. The surgical system of claim 11, wherein the navigation system is further configured to provide a user-selectable object configured to allow a user to manipulate the boundary provided by the segmentation algorithm.

13. The surgical system of claim 1, wherein the navigation system is configured to define a first boundary relative to a critical structure on the patient and to project a second boundary that is spaced a first distance from the first boundary, the first boundary and the second boundary defining a volume representing the alert zone, and
   wherein the navigation system is configured to send a signal to the control processor to manipulate the variable speed motor of the high-speed surgical instrument to transition the rotation of the bur from the first cutting speed to the second cutting speed upon the bur entering the volume representing the alert zone.

14. The surgical system of claim 13, wherein the second boundary is projected at a user selectable distance from the first boundary.

15. The surgical system of claim 13, wherein the second boundary is projected at the first distance relative to the first boundary based on a user-selectable depth.

16. The surgical system of claim 13, wherein the navigation system is configured to define the first boundary based on a planned pose of an implant selected to be inserted in the patient, and the second boundary at the first distance from the first boundary along the axis of the implant.

17. The surgical system of claim 1, wherein upon the navigation system being unable to determine a position of the bur relative to the patient for a defined period of time, the navigation system is further configured to send a second signal to the control processor to cause deactivation of the variable speed motor of the high-speed surgical instrument until the navigation system is subsequently able to determine a position of the bur relative to the patient.

18. A surgical system configured to allow a medical professional to define an alert zone relative to a critical structure on a patient in a known coordinate system to assist the medical professional in performing surgery on a patient, the surgical system comprising:
   a navigation system;
   a control console comprising a control processor in communication with the navigation system;
   a high-speed surgical instrument including a bur, the high-speed surgical instrument comprising a variable speed motor in communication with the control processor;
   a footswitch for controlling operation of the variable speed motor of the high-speed surgical instrument in communication with the control processor;
   a tactile alert device coupled to the footswitch, the tactile alert device comprising a motor that vibrates when activated such that the vibration of the motor provides a physical alert capable of being felt in a user's foot that is in contact with the footswitch for controlling operation of the variable speed motor of the high-speed surgical instrument;
   wherein the navigation system is configured to actively determine a position of the bur relative to the alert zone in the known coordinate system;
   wherein the navigation system is configured to send a signal to the control processor to manipulate the variable speed motor of the high-speed surgical instrument to transition the rotation of the bur from a first cutting speed to a second cutting speed when the navigation system determines the bur enters the alert zone, the transition of the bur from the first cutting speed to the second cutting speed creating a perceptible change as the bur transitions from the first cutting speed to the second cutting speed to notify the medical professional that the bur has entered the alert zone; and
   wherein the navigation system is configured to trigger the tactile alert device to vibrate when the navigation system determines the bur enters the alert zone.

19. A surgical system configured to allow a medical professional to define an alert zone relative to a critical structure on a patient in a known coordinate system to assist the medical professional in performing surgery on a patient, the surgical system comprising:
   a navigation system;
   a control console comprising a control processor in communication with the navigation system;
   a high-speed surgical instrument including a bur, the high-speed surgical instrument comprising a variable speed motor in communication with the control processor; and
   at least one of an audible alert device capable of producing a first notification and a tactile alert device capable of producing a second notification;
   wherein the navigation system is configured to actively determine a position of the bur relative to the alert zone in the known coordinate system;
   wherein the navigation system is configured to send a signal to the control processor to manipulate the variable speed motor of the high-speed surgical instrument to transition the rotation of the bur from a first cutting speed to a second cutting speed when the navigation system determines the bur enters the alert zone, the transition of the bur from the first cutting speed to the second cutting speed creating a perceptible change as the bur transitions from the first cutting speed to the second cutting speed to notify the medical professional that the bur has entered the alert zone;
   wherein the alert zone comprises a user-selectable first boundary and a user-selectable second boundary;
   wherein the navigation system is configured to allow a user to assign one of the first notification or the second notification to either of the first boundary or the second boundary; and
   wherein the navigation system is configured to manipulate one of the audible alert device and the tactile alert device to produce one of the first notification or the second notification based on the position of the bur relative to the first boundary or the second boundary.

* * * * *